US009364531B2

(12) United States Patent
Schrier et al.

(10) Patent No.: US 9,364,531 B2
(45) Date of Patent: *Jun. 14, 2016

(54) IMMUNOSTIMULATORY OLIGODEOXYNUCLEOTIDES

(75) Inventors: Carla Christina Schrier, Boxmeer (NL); Thomas Simon Ilg, Nieder-Olm (DE)

(73) Assignee: Intervet Inc., Madison, NJ (US)

(*) Notice: Subject to any disclaimer, the term of this patent is extended or adjusted under 35 U.S.C. 154(b) by 115 days.

This patent is subject to a terminal disclaimer.

(21) Appl. No.: 13/976,121

(22) PCT Filed: Dec. 29, 2011

(86) PCT No.: PCT/EP2011/074211
§ 371 (c)(1),
(2), (4) Date: Jun. 26, 2013

(87) PCT Pub. No.: WO2012/089800
PCT Pub. Date: Jul. 5, 2012

(65) Prior Publication Data
US 2014/0205633 A1  Jul. 24, 2014

Related U.S. Application Data

(60) Provisional application No. 61/430,301, filed on Jan. 6, 2011.

(30) Foreign Application Priority Data

Dec. 30, 2010 (EP) .................................. 10197435

(51) Int. Cl.
*A61K 39/17* (2006.01)
*A61K 39/12* (2006.01)
*C12N 15/117* (2010.01)
*A61K 39/39* (2006.01)
*A61K 39/00* (2006.01)

(52) U.S. Cl.
CPC ............... *A61K 39/17* (2013.01); *A61K 39/12* (2013.01); *A61K 39/39* (2013.01); *C12N 15/117* (2013.01); *A61K 2039/552* (2013.01); *A61K 2039/55561* (2013.01); *A61K 2039/55566* (2013.01); *C12N 2310/17* (2013.01); *C12N 2310/315* (2013.01); *C12N 2310/341* (2013.01); *C12N 2310/345* (2013.01); *C12N 2760/18134* (2013.01); *C12N 2760/18334* (2013.01); *C12N 2770/20034* (2013.01)

(58) Field of Classification Search
None
See application file for complete search history.

(56) References Cited

U.S. PATENT DOCUMENTS

| 7,749,979 B2 | 7/2010 | Chaung et al. |
| 2003/0212028 A1 | 11/2003 | Raz et al. |
| 2004/0229835 A1 | 11/2004 | Krieg et al. |
| 2004/0235774 A1 | 11/2004 | Bratzler et al. |
| 2009/0123467 A1* | 5/2009 | Bedi et al. .................. 424/134.1 |
| 2009/0155303 A1 | 6/2009 | Wang et al. |
| 2009/0253134 A1 | 10/2009 | Brunner et al. |
| 2010/0003288 A1 | 1/2010 | Chaung et al. |
| 2014/0193457 A1 | 7/2014 | Schrier et al. |
| 2014/0205633 A1* | 7/2014 | Schrier et al. .............. 424/214.1 |

FOREIGN PATENT DOCUMENTS

| DE | 102006031483 B4 | 12/2009 |
| JP | 2005517632 | 6/2005 |
| JP | 2009542236 | 12/2009 |
| JP | 2010535248 | 11/2010 |
| WO | WO9818810 | 5/1998 |
| WO | 03/015711 A2 | 2/2003 |
| WO | 2004005476 A2 | 1/2004 |
| WO | WO2004016805 A2 | 2/2004 |
| WO | 2004/058179 A2 | 7/2004 |
| WO | 2006079291 A1 | 8/2006 |
| WO | 2007020017 A1 | 2/2007 |
| WO | 2008/142509 A2 | 11/2008 |
| WO | 2009059050 A2 | 5/2009 |
| WO | 2010021289 A1 | 2/2010 |
| WO | 2010067286 A2 | 6/2010 |
| WO | 2010/125480 A1 | 11/2010 |
| WO | 2012089800 A1 | 7/2012 |

OTHER PUBLICATIONS

Sequence alignment of instant SEQ ID No. 1 with SEQ ID No. 1 in 14119492 filed Nov. 22, 2013.*
Weiner et al. (PNAS. 1997; 94: 10833-10837).*
Sequence alignment of instant SEQ ID No. 1 with SEQ ID No. 1 in 14119514 filed Nov. 22, 2013.*
Kojima et al. (Vaccine. 2002; 20: 2857-2865).*
Brownlie et al., "Chicken TLR21 acts as a functional homologue to mammalian TLR9 in the recognition of CpG oligodeoxynucleotides", Molecular Immunology, 2009, pp. 3163-3170, vol. 46.
Ciraci et al., "Avian-specific TLRs and downstream effector responses to CpG-induction in chicken macrophages", Developmental and Comparative Immunology, 2011, pp. 392-398, vol. 35.
Dar et al., "Immunotherapeutic Potential of CpG Oligonucleotides in Chickens", Japan Poultry Science Association, 2009, pp. 69-80, vol. 46.
Han et al., "Involvement of TLR21 in baculovirus-induced interleukin-12 gene expression in avian macrophage-like cell line HD11", Veterinary Microbiology, 2010, pp. 75-81, vol. 144.

(Continued)

*Primary Examiner* — Shanon A Foley

(57) ABSTRACT

The present invention relates to immunostimulatory oligodeoxynucleotides, vectors and vaccines comprising such oligodeoxynucleotides, to their use as a medicament, to their use in preventing or combating infectious disease, to methods for the detection of such oligodeoxynucleotides and to cells to be used in these method.

19 Claims, 32 Drawing Sheets

(56) References Cited

OTHER PUBLICATIONS

Figure 1:
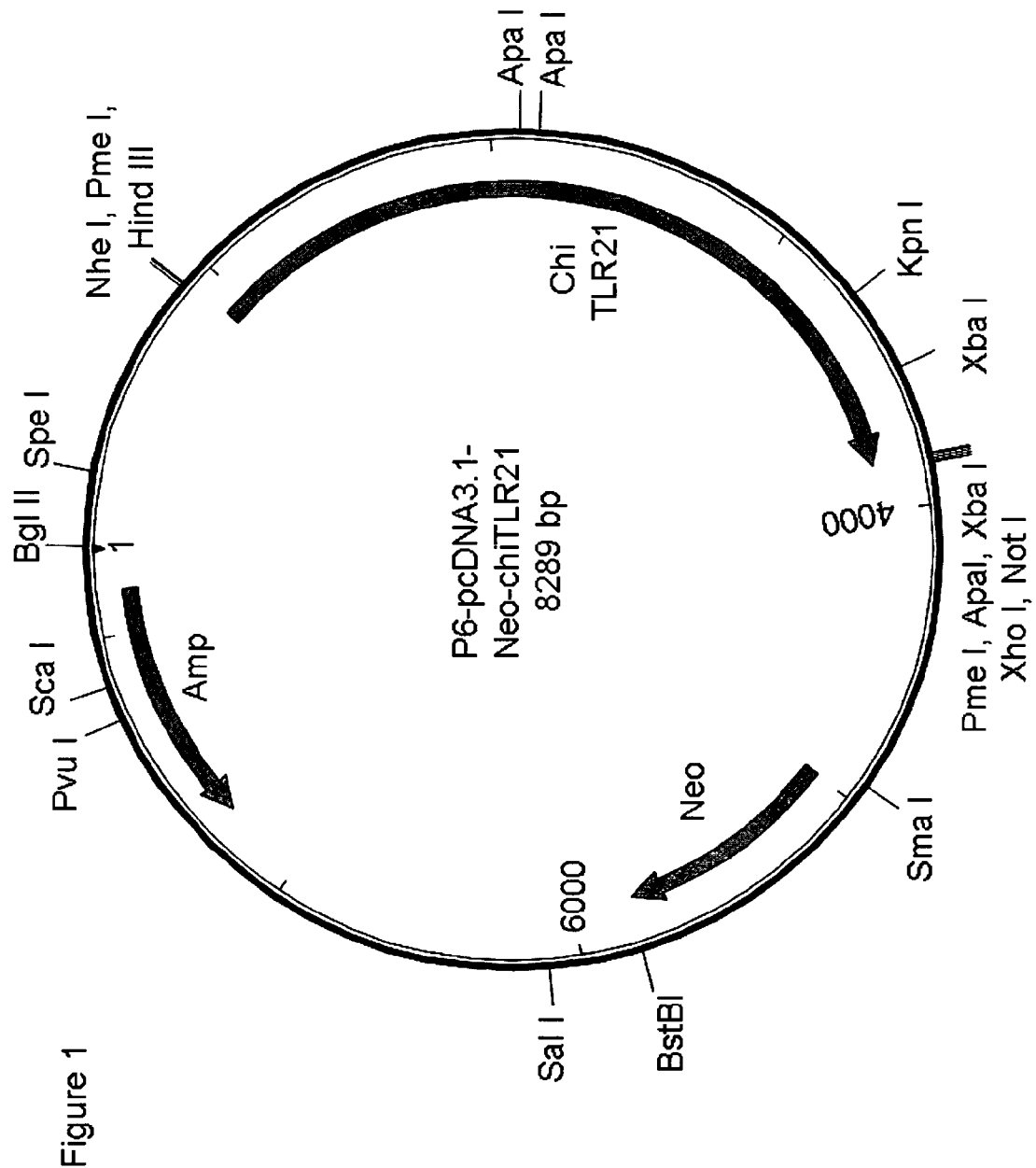
Figure 2:
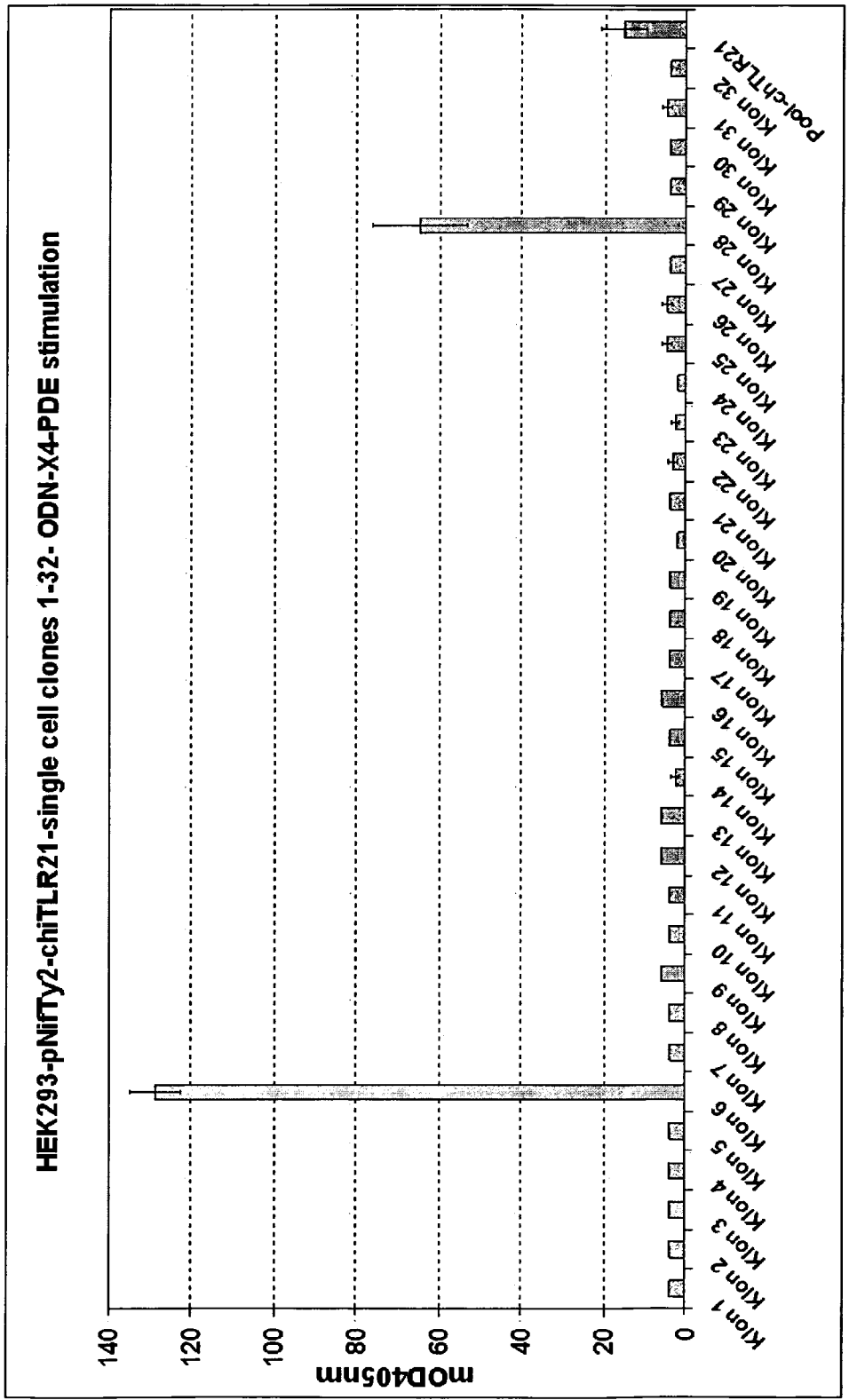
Figure 3:
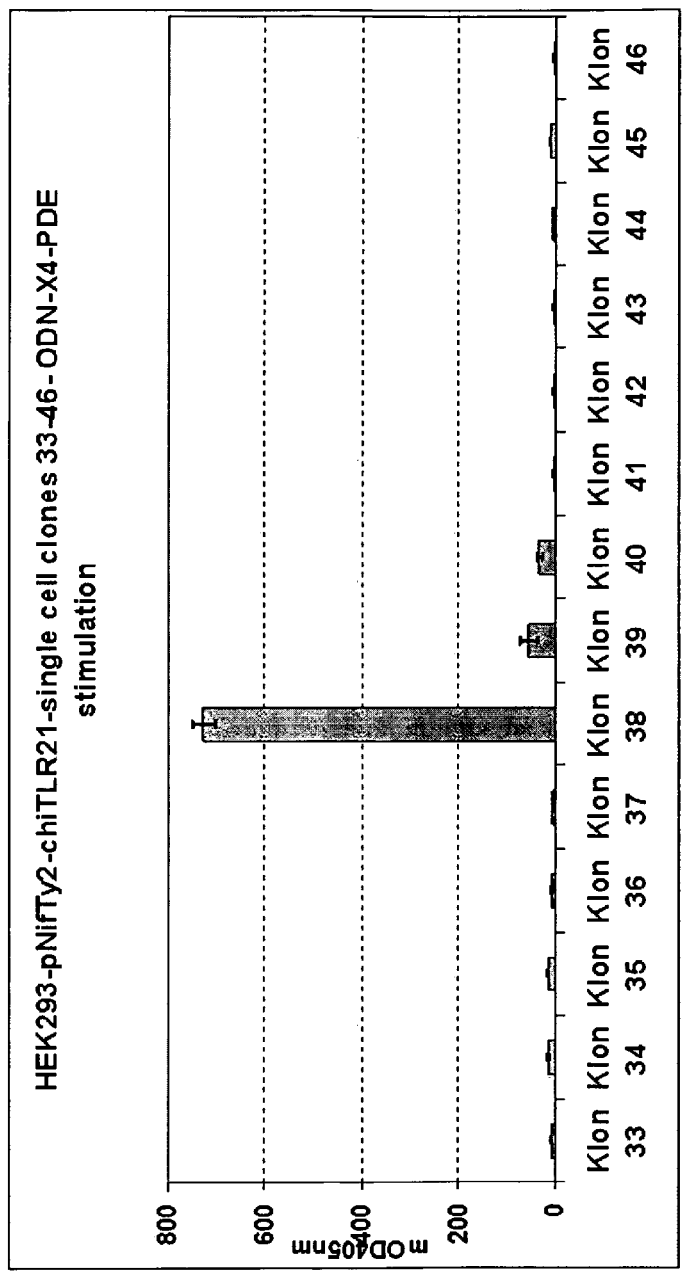
Figure 4:
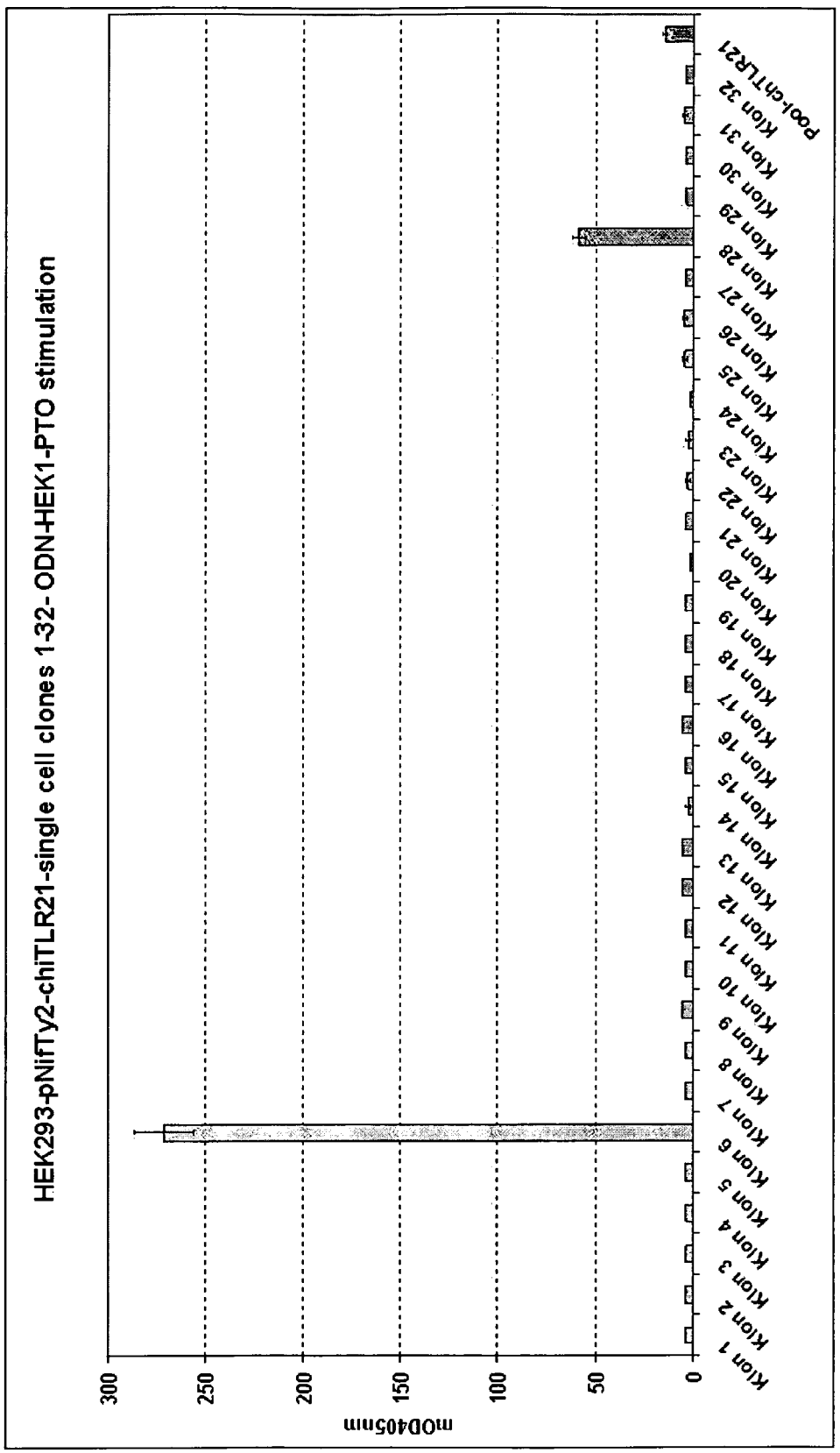
Figure 5:
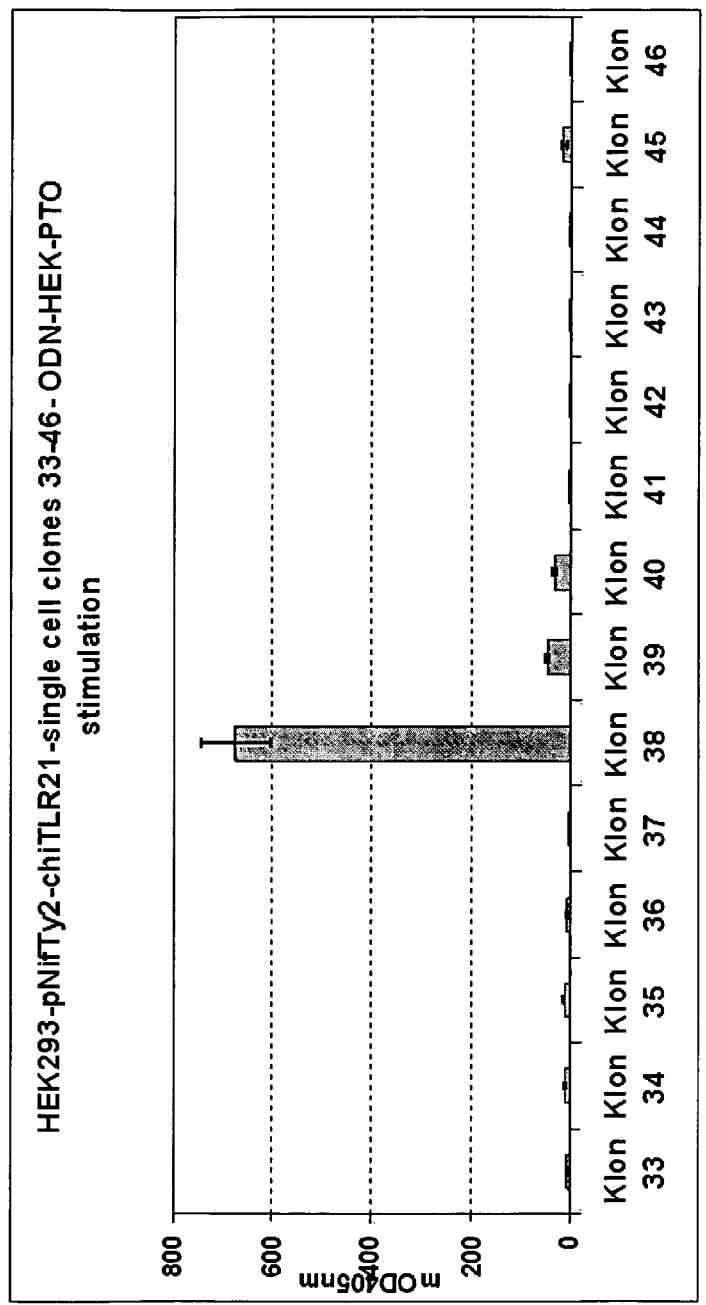

Iwasaki et al., "Regulation of Adaptive Immunity by the innate Immune System", Science, 2010, pp. 291-295, vol. 327.
Keestra et al., "Chicken TLR21 Is an Innate CpG DNA Receptor Distinct from Mammalian TLR9", The Journal of Immunology, 2010, pp. 460-467, vol. 185(1).
Licchesi et al., "Transcriptional regulation of Wnt inhibitory factor-1 by Miz-1/c-Myc", Oncogene, 2010, pp. 5923-5934, vol. 29(44).
Licchesi et al., Supplementary Table 1: Primer Sequences, XP-002664075, Retrieved from http://www.nature.com/onc/journal/v29/n44//extref/onc2010322x4.xls on Nov. 22, 2011.
Linghua et al., "Vaccination with Newcastle disease vaccine and CpG oligodeoxynucleotides induces specific immunity and protection against Newcastle disease virus in SPF chicken", Veterinary Immunology and Immunopathology, 2007, pp. 216-222, vol. 115.
Medzhitov, Ruslan, "Approaching the Asymptote: 20 Years Later", Immunity, 2009, pp. 766-775, vol. 30.
Menard et al., "Characterization of Immunostimulatory CpG-Rich Sequences from Different Bifidobacterium Species", Applied and environmental Microbiology, 2010, pp. 2816-2855, vol. 70(9).
European Search Report for EP Application No. EP 10 19 7435, dated Jun. 11, 2012.
International Search Report for corresponding PCT/EP2011/074211, mailed on Apr. 10, 2012.
Rankin, et al., "CpG Motif Identification for Veterinary and Laboratory Species Demonstrates that Sequence Recognition Is Highly Conserve"d, Antisense & Nucleic Acid Drug Development, 2001, pp. 333-340, vol. 11.
Burger-Kentischer, A. et al., A new cell-based innate immune receptor assay for the examination of receptor activity, ligand specificity, signalling pathways and the detection of pyrogens, Journal of Immunological Methods, Jun. 1, 2010, pp. 93-103, vol. 358, No. 1-2.
Dalpke, A. et al, Activation of toll-like receptor 9 by DNA from different bacterial species, Infection and Immunity, Feb. 2006, pp. 940-946, Vo.. 74, No. 2.
Domeika, et al., Characteristics of oligodeoxyribonucleotides that induce interferon (IFN)-alpha in the pig and the phenotype of the IFN_alpha producing cells, Veterinary Immunology and Immunopathology, 2004, pp. 87-102, vol. 101.
Iliev, I.D. et al., Immunostimulatory oligodeoxynucleotide containing TTTCGTTT motif from Lactobacillus rhamnosus GG DNA potentially suppresses OVA-specific IgE production in mice, Scandinavian Journal of Immunology, Apr. 1, 2008, pp. 370-376, vol. 67, No. 4.
Lee, K.W. et al., Immunostimulatory oligodeoxynucleotide isolated from genome wide screening of Mycobacterium bovis chromosomal DNA, Molecular Immunology, May 1, 2006, pp. 2107-2118, vol. 43, No. 13.
Loots, K. et al., CpG motifs as adjuvant in DNA vaccination against Chlamydophila psittaci in turkeys, Vaccine, May 22, 2006, pp. 4598-4601, vol. 24, No. 21.
Pontarollo, R.A. et al., Monocytes are required for optimum in vitro stimulation of bovine peripheral blood mononuclear cells by non-methylated CpG motifs, Veterinary Immunology and Immunopathology, Jan. 1, 2002, pp. 43-59, vol. 84, No. 1-2.
Hartmann, G. et al, Delineation of a CpG Phosphorothioate Oligodeoxynucleotide for activating primate immune responses in vitro and in vivo, The Journal of Immunology, 2000, pp. 1617-1624, vol. 164.
Kandimalla, E.R. et al, Toll-like receptor 9: modulation of recognition and cytokine induction by novel synthetic CpG DNAs, Biochemical Society Transactions, 2003, pp. 654-658, vol. 31, Part 3.
Vleugels, B. et al, Stimulatory effect of CpG sequences on humoral response in chickens, Poultry Science, 2002, pp. 1317-1321, vol. 81.

* cited by examiner

SEQUENCE LISTING

<160> NUMBER OF SEQ ID NOS: 138

<210> SEQ ID NO 1
<211> LENGTH: 33
<212> TYPE: DNA
<213> ORGANISM: Artificial sequence
<220> FEATURE:
<223> OTHER INFORMATION: Synthetic DNA

<400> SEQUENCE: 1
gaagcttacc atgatggaga cagcggagaa ggc    33

<210> SEQ ID NO 2
<211> LENGTH: 33
<212> TYPE: DNA
<213> ORGANISM: Artificial sequence
<220> FEATURE:
<223> OTHER INFORMATION: Synthetic DNA

<400> SEQUENCE: 2
ggcggccgct acatctgttt gtctccttcc ctg    33

<210> SEQ ID NO 3

<211> LENGTH: 2935
<212> TYPE: DNA
<213> ORGANISM: Artificial sequence
<220> FEATURE:
<223> OTHER INFORMATION: Synthetic DNA

<400> SEQUENCE: 3

| | | | | | |
|---|---|---|---|---|---|
| aagcttacca | tgatggagac | agcggagaag | gcatggccca | gcaccaggat | gtgcccctcc | 60 |
| cactgctgtc | cactctggct | gctgctgctg | gtgacagtga | cactgatgcc | gatggtgcac | 120 |
| ccgtatggct | ttcgcaactg | cattgaggat | gtcaaggcac | ctttgtactt | ccgctgcatc | 180 |
| cagcgcttcc | tgcagtcgcc | ggccctggca | gtgtctgacc | tgccaccaca | tgccatcgcg | 240 |
| ctcaatctgt | catacaacaa | aatgcgctgc | ctgcagccct | ctgcctttgc | ccacctgaca | 300 |
| cagctgcata | ccctggacct | gacctacaac | ctcctggaga | ccctctcccc | tggtgccttc | 360 |
| aatgggctgg | gtgtgctggt | ggtgctggac | ctgtctcaca | caagctgac | cacacttgct | 420 |
| gaaggggtgt | caacagcttg | ggcaacctg | tcctcgctgc | aggtacaaca | taaccccctc | 480 |
| agcacggtgt | caccaagtgc | tctgctaccc | ctggtcaacc | tgcgccgcct | gtctctacgg | 540 |
| ggcgggcggc | tgaatgggtt | gggggcagtg | gcagtggcag | tgcagggctt | ggcacagctg | 600 |
| gagctgttgg | acctatgtga | aaacaacctg | acaacgctgg | ggccaggccc | accgctaccc | 660 |
| gcctcgctgc | tcaccctgca | gctgtgcaac | aactcgctga | gggagttagc | gggggggcagc | 720 |
| ccggagatgc | tatggcacgt | gaagatactc | gacctctcct | acaacagtat | ctcacaggcg | 780 |
| gaggtcttca | cccagctcca | cctgcgcaac | atcagcctgc | tccacctgat | cggcaacccc | 840 |
| ttggatgtct | tccacctgtt | ggacatctct | gacatccaac | ctcgcagcct | ggatttctct | 900 |
| gggttggtgc | tggggggctca | ggggctggat | aaggtgtgcc | tgaggctgca | gggtccccag | 960 |
| gccttgcggg | gctgcagct | acaacgcaac | gggctgaagg | tgctgcattg | taatgcactg | 1020 |
| cagttgtgtc | ctgtgctgag | agagctggac | ctgtcctgga | accggctaca | gcacgtgggc | 1080 |
| tgtgccggcc | ggctgctggg | caagaagcag | cgggagaagc | tggaagtgct | gacagtggaa | 1140 |
| cacaacctgc | tgaagaaact | gccgtcttgc | ctgggggccc | aggtgctgcc | tcggctgtac | 1200 |
| aacatttcct | tccgctttaa | ccgcatcctg | actgttgggc | cccaagcctt | tgcctacgcc | 1260 |
| ccggccctgc | aggtgttgtg | gctcaatatt | aacagcctgg | tgtggctgga | caggcaggca | 1320 |
| ctgtggaggc | tgcacaacct | gacagagctg | cgcctggaca | caacctgct | gaccgacctc | 1380 |
| tatcacaact | ccttcattga | cctccacaga | ctgcgcaccc | tcaacctgcg | caacaaccgt | 1440 |
| gtctccgtcc | tcttctctgg | tgtcttccag | gggctggctg | agctgcagac | gctggattta | 1500 |
| gggggcaaca | acttgcgcca | cctgactgca | cagtcactgc | agggctgcc | caaactgcgc | 1560 |
| aggctgtacc | tggaccgcaa | cagattgctg | gaggtgagca | gcactgtgtt | cgccccagtg | 1620 |
| caggctaccc | tgggggtgct | ggacctgcgg | gccaacaacc | tgcagtacat | ctcacagtgg | 1680 |
| ctgcgcaagc | cgccaccctt | ccgcaacctg | agcagcctgt | acgacctgaa | gctgcaggcg | 1740 |
| cagcagccct | atggactgaa | gatgctgcct | cactacttct | tccagggctt | ggtgaggctg | 1800 |
| cagcagctgt | cgctgtcaca | gaacatgctg | cggtccatcc | caccggatgt | cttcgaggac | 1860 |
| ttgggccagc | tgcgctccct | ggcattggct | gacagcagca | atgggctgca | tgacctgcct | 1920 |
| gacggcatct | tcagaaacct | gggcaacctg | cggttcctgg | acctggagaa | tgcagggctg | 1980 |
| cactcgctca | ctctggaagt | cttcggcaat | ctcagccggc | tgcaggtgct | gcacttggcc | 2040 |
| agaaacgagc | tgaagacctt | caatgacagc | gttgccagcc | ggctgtcctc | cttgcgctac | 2100 |
| ctggacctgc | gcaagtgtcc | gctcagctgc | acctgtgaca | acatgtggct | gcagggctgg | 2160 |

```
ctgaacaaca gccgtgtgca ggttgtctac ccctacaact acacctgtgg ctcacagcac      2220
aatgcctaca tccacagctt tgacacacac gtctgcttcc tggacctggg gctctatctc      2280
tttgctggga ctgcaccggc agtgctgctg ctgctggtgg tgccggtggt gtaccaccgc      2340
gcctactgga ggctgaagta ccactggtac cttctgcggt gctgggtcaa ccagcggtgg      2400
cggcgggagg aaaagtgcta cctctatgac agctttgtgt cctacaattc agctgatgaa      2460
agttgggtgt tgcagaagct ggtgcctgag ctggagcacg gtgccttccg cctctgcttg      2520
caccaccgcg acttccagcc gggccgcagc atcattgaca acattgtgga tgctgtctac      2580
aacagccgga gacggtgtg cgtggtgagc cgcagctacc tgcgcagcga gtggtgctct      2640
ctagaggtgc agttggccag ctaccggctg ttggatgagc ggcgtgacat cctggtactg      2700
gtgctgctgg aggacgtggg tgatgctgag ctgtctgcct accaccgcat gcggcgggtg      2760
ctgctgcggc gcacctacct gcgctggcct cttgaccccg cagctcagcc gctcttttgg      2820
gcacggctga agagggcact gaggtgggga gaggaggag aggaggagga agaagaaggt      2880
ttgggtggag ggacgggaag gcccagggaa ggagacaaac agatgtagcg gccgc          2935
```

<210> SEQ ID NO 4
<211> LENGTH: 29
<212> TYPE: DNA
<213> ORGANISM: Artificial sequence
<220> FEATURE:
<223> OTHER INFORMATION: Synthetic DNA

<400> SEQUENCE: 4
gggggggacg tcgacgtcga cgtcggggg                                          29

<210> SEQ ID NO 5
<211> LENGTH: 29
<212> TYPE: DNA
<213> ORGANISM: Artificial sequence
<220> FEATURE:
<223> OTHER INFORMATION: Synthetic DNA

<400> SEQUENCE: 5 ggggggtcg ttgtcgttgt cgttggggg                                           29

<210> SEQ ID NO 6
<211> LENGTH: 29
<212> TYPE: DNA
<213> ORGANISM: Artificial sequence
<220> FEATURE:
<223> OTHER INFORMATION: Synthetic DNA

<400> SEQUENCE: 6 gggggaacg ttaacgttaa cgttggggg                                           29

<210> SEQ ID NO 7
<211> LENGTH: 29
<212> TYPE: DNA
<213> ORGANISM: Artificial sequence
<220> FEATURE:
<223> OTHER INFORMATION: Synthetic DNA

<400> SEQUENCE: 7 gggggttcg ttttcgtttt cgttggggg                                           29

<210> SEQ ID NO 8
<211> LENGTH: 29
<212> TYPE: DNA

```
<213> ORGANISM: Artificial sequence
<220> FEATURE:
<223> OTHER INFORMATION: Synthetic DNA

<400> SEQUENCE: 8 gggggggaacg aaaacgaaaa cgaagggggg                              29

<210> SEQ ID NO 9
<211> LENGTH: 29
<212> TYPE: DNA
<213> ORGANISM: Artificial sequence
<220> FEATURE:
<223> OTHER INFORMATION: Synthetic DNA

<400> SEQUENCE: 9 gggggggcgcg cgcgcgcgcg cgcgggggg                               29

<210> SEQ ID NO 10
<211> LENGTH: 29
<212> TYPE: DNA
<213> ORGANISM: Artificial sequence
<220> FEATURE:
<223> OTHER INFORMATION: Synthetic DNA

<400> SEQUENCE: 10
ggggggttcg aattcgaatt cgaagggggg                               29

<210> SEQ ID NO 11
<211> LENGTH: 29
<212> TYPE: DNA
<213> ORGANISM: Artificial sequence
<220> FEATURE:
<223> OTHER INFORMATION: Synthetic DNA

<400> SEQUENCE: 11 gggggggtgcg gttgcggttg cggtgggggg                              29

<210> SEQ ID NO 12
<211> LENGTH: 29
<212> TYPE: DNA
<213> ORGANISM: Artificial sequence
<220> FEATURE:
<223> OTHER INFORMATION: Synthetic DNA

<400> SEQUENCE: 12 gggggggtacg gttacggtta cggtgggggg                              29

<210> SEQ ID NO 13
<211> LENGTH: 29
<212> TYPE: DNA
<213> ORGANISM: Artificial sequence
<220> FEATURE:
<223> OTHER INFORMATION: Synthetic DNA

<400> SEQUENCE: 13 gggggggttcg gtttcggttt cggtgggggg                              29

<210> SEQ ID NO 14
<211> LENGTH: 29
<212> TYPE: DNA
<213> ORGANISM: Artificial sequence
<220> FEATURE:
<223> OTHER INFORMATION: Synthetic DNA

<400> SEQUENCE: 14 gggggggtccg gttccggttc cggtgggggg                              29
```

<210> SEQ ID NO 15
<211> LENGTH: 29
<212> TYPE: DNA
<213> ORGANISM: Artificial sequence
<220> FEATURE:
<223> OTHER INFORMATION: Synthetic DNA

<400> SEQUENCE: 15 gggggggtgcg attgcgattg cgatgggggg                                29

<210> SEQ ID NO 16
<211> LENGTH: 29
<212> TYPE: DNA
<213> ORGANISM: Artificial sequence
<220> FEATURE:
<223> OTHER INFORMATION: Synthetic DNA

<400> SEQUENCE: 16 gggggggtacg attacgatta cgatgggggg                                29

<210> SEQ ID NO 17
<211> LENGTH: 29
<212> TYPE: DNA
<213> ORGANISM: Artificial sequence
<220> FEATURE:
<223> OTHER INFORMATION: Synthetic DNA

<400> SEQUENCE: 17
ggggggttcg atttcgattt cgatgggggg                                 29

<210> SEQ ID NO 18
<211> LENGTH: 29
<212> TYPE: DNA
<213> ORGANISM: Artificial sequence
<220> FEATURE:
<223> OTHER INFORMATION: Synthetic DNA

<400> SEQUENCE: 18 gggggggtccg attccgattc cgatgggggg                                29

<210> SEQ ID NO 19
<211> LENGTH: 29
<212> TYPE: DNA
<213> ORGANISM: Artificial sequence
<220> FEATURE:
<223> OTHER INFORMATION: Synthetic DNA

<400> SEQUENCE: 19 gggggggtgcg tttgcgtttg cgttgggggg                                29

<210> SEQ ID NO 20
<211> LENGTH: 29
<212> TYPE: DNA
<213> ORGANISM: Artificial sequence
<220> FEATURE:
<223> OTHER INFORMATION: Synthetic DNA

<400> SEQUENCE: 20 gggggggtacg tttacgttta cgttgggggg                                29

<210> SEQ ID NO 21
<211> LENGTH: 29
<212> TYPE: DNA
<213> ORGANISM: Artificial sequence
<220> FEATURE:

<223> OTHER INFORMATION: Synthetic DNA

<400> SEQUENCE: 21 gggggggttcg ttttcgtttt cgttgggggg                29

<210> SEQ ID NO 22
<211> LENGTH: 29
<212> TYPE: DNA
<213> ORGANISM: Artificial sequence
<220> FEATURE:
<223> OTHER INFORMATION: Synthetic DNA

<400> SEQUENCE: 22
ggggggtccg tttccgtttc cgttgggggg                29

<210> SEQ ID NO 23
<211> LENGTH: 29
<212> TYPE: DNA
<213> ORGANISM: Artificial sequence
<220> FEATURE:
<223> OTHER INFORMATION: Synthetic DNA

<400> SEQUENCE: 23
ggggggtgcg cttgcgcttg cgctgggggg                29

<210> SEQ ID NO 24
<211> LENGTH: 29
<212> TYPE: DNA
<213> ORGANISM: Artificial sequence
<220> FEATURE:
<223> OTHER INFORMATION: Synthetic DNA

<400> SEQUENCE: 24
ggggggtacg cttacgctta cgctgggggg                29

<210> SEQ ID NO 25
<211> LENGTH: 29
<212> TYPE: DNA
<213> ORGANISM: Artificial sequence
<220> FEATURE:
<223> OTHER INFORMATION: Synthetic DNA

<400> SEQUENCE: 25 gggggggttcg ctttcgcttt cgctgggggg                29

<210> SEQ ID NO 26
<211> LENGTH: 29
<212> TYPE: DNA
<213> ORGANISM: Artificial sequence
<220> FEATURE:
<223> OTHER INFORMATION: Synthetic DNA

<400> SEQUENCE: 26
ggggggtccg cttccgcttc cgctgggggg                29

<210> SEQ ID NO 27
<211> LENGTH: 29
<212> TYPE: DNA
<213> ORGANISM: Artificial sequence
<220> FEATURE:
<223> OTHER INFORMATION: Synthetic DNA

<400> SEQUENCE: 27 gggggggttcg ttttcgtttt cgttgggggg                29

```
<210> SEQ ID NO 28
<211> LENGTH: 29
<212> TYPE: DNA
<213> ORGANISM: Artificial sequence
<220> FEATURE:
<223> OTHER INFORMATION: Synthetic DNA

<400> SEQUENCE: 28 gggggggttcg tgttcgtgtt cgtgggggg                                   29

<210> SEQ ID NO 29
<211> LENGTH: 29
<212> TYPE: DNA
<213> ORGANISM: Artificial sequence
<220> FEATURE:
<223> OTHER INFORMATION: Synthetic DNA

<400> SEQUENCE: 29 gggggggttcg tattcgtatt cgtaggggg                                   29

<210> SEQ ID NO 30
<211> LENGTH: 29
<212> TYPE: DNA
<213> ORGANISM: Artificial sequence
<220> FEATURE:
<223> OTHER INFORMATION: Synthetic DNA

<400> SEQUENCE: 30 gggggggttcg tcttcgtctt cgtcggggg                                   29

<210> SEQ ID NO 31
<211> LENGTH: 29
<212> TYPE: DNA
<213> ORGANISM: Artificial sequence
<220> FEATURE:
<223> OTHER INFORMATION: Synthetic DNA

<400> SEQUENCE: 31 ggggggggtcg ttgtcgttgt cgttggggg                                   29

<210> SEQ ID NO 32
<211> LENGTH: 29
<212> TYPE: DNA
<213> ORGANISM: Artificial sequence
<220> FEATURE:
<223> OTHER INFORMATION: Synthetic DNA

<400> SEQUENCE: 32 gggggggatcg ttatcgttat cgttggggg                                   29

<210> SEQ ID NO 33
<211> LENGTH: 29
<212> TYPE: DNA
<213> ORGANISM: Artificial sequence
<220> FEATURE:
<223> OTHER INFORMATION: Synthetic DNA

<400> SEQUENCE: 33 gggggggctcg ttctcgttct cgttggggg                                   29

<210> SEQ ID NO 34
<211> LENGTH: 29
<212> TYPE: DNA
<213> ORGANISM: Artificial sequence
<220> FEATURE:
<223> OTHER INFORMATION: Synthetic DNA
```

```
<400> SEQUENCE: 34 gggggttcg ttttcgtttt cgttggggg                                          29

<210> SEQ ID NO 35
<211> LENGTH: 29
<212> TYPE: DNA
<213> ORGANISM: Artificial sequence
<220> FEATURE:
<223> OTHER INFORMATION: Synthetic DNA

<400> SEQUENCE: 35 gggggttcg ttttcgtttt cgttggggg                                          29

<210> SEQ ID NO 36
<211> LENGTH: 28
<212> TYPE: DNA
<213> ORGANISM: Artificial sequence
<220> FEATURE:
<223> OTHER INFORMATION: Synthetic DNA

<400> SEQUENCE: 36 ggggttcgt tttcgttttc gttggggg                                           28

<210> SEQ ID NO 37
<211> LENGTH: 27
<212> TYPE: DNA
<213> ORGANISM: Artificial sequence
<220> FEATURE:
<223> OTHER INFORMATION: Synthetic DNA

<400> SEQUENCE: 37
ggggttcgtt ttcgttttcg ttggggg                                           27

<210> SEQ ID NO 38
<211> LENGTH: 26
<212> TYPE: DNA
<213> ORGANISM: Artificial sequence
<220> FEATURE:
<223> OTHER INFORMATION: Synthetic DNA

<400> SEQUENCE: 38
gggttcgttt tcgttttcgt tggggg                                            26

<210> SEQ ID NO 39
<211> LENGTH: 25
<212> TYPE: DNA
<213> ORGANISM: Artificial sequence
<220> FEATURE:
<223> OTHER INFORMATION: Synthetic DNA

<400> SEQUENCE: 39
ggttcgtttt cgttttcgtt ggggg                                             25

<210> SEQ ID NO 40
<211> LENGTH: 24
<212> TYPE: DNA
<213> ORGANISM: Artificial sequence
<220> FEATURE:
<223> OTHER INFORMATION: Synthetic DNA

<400> SEQUENCE: 40
gttcgttttc gttttcgttg gggg                                              24

<210> SEQ ID NO 41
<211> LENGTH: 23
```

<212> TYPE: DNA
<213> ORGANISM: Artificial sequence
<220> FEATURE:
<223> OTHER INFORMATION: Synthetic DNA

<400> SEQUENCE: 41
ttcgttttcg ttttcgttgg ggg                                    23

<210> SEQ ID NO 42
<211> LENGTH: 29
<212> TYPE: DNA
<213> ORGANISM: Artificial sequence
<220> FEATURE:
<223> OTHER INFORMATION: Synthetic DNA

<400> SEQUENCE: 42 gggggggttcg ttttcgtttt cgttggggg                             29

<210> SEQ ID NO 43
<211> LENGTH: 28
<212> TYPE: DNA
<213> ORGANISM: Artificial sequence
<220> FEATURE:
<223> OTHER INFORMATION: Synthetic DNA

<400> SEQUENCE: 43 gggggggttcg ttttcgtttt cgttgggg                              28

<210> SEQ ID NO 44
<211> LENGTH: 27
<212> TYPE: DNA
<213> ORGANISM: Artificial sequence
<220> FEATURE:
<223> OTHER INFORMATION: Synthetic DNA

<400> SEQUENCE: 44 gggggggttcg ttttcgtttt cgttggg                               27

<210> SEQ ID NO 45
<211> LENGTH: 26
<212> TYPE: DNA
<213> ORGANISM: Artificial sequence
<220> FEATURE:
<223> OTHER INFORMATION: Synthetic DNA

<400> SEQUENCE: 45 gggggggttcg ttttcgtttt cgttgg                                26

<210> SEQ ID NO 46
<211> LENGTH: 25
<212> TYPE: DNA
<213> ORGANISM: Artificial sequence
<220> FEATURE:
<223> OTHER INFORMATION: Synthetic DNA

<400> SEQUENCE: 46 gggggggttcg ttttcgtttt cgttg                                 25

<210> SEQ ID NO 47
<211> LENGTH: 24
<212> TYPE: DNA
<213> ORGANISM: Artificial sequence
<220> FEATURE:
<223> OTHER INFORMATION: Synthetic DNA

<400> SEQUENCE: 47

```
gggggggttcg ttttcgtttt cgtt                                      24
```

```
<210> SEQ ID NO 48
<211> LENGTH: 29
<212> TYPE: DNA
<213> ORGANISM: Artificial sequence
<220> FEATURE:
<223> OTHER INFORMATION: Synthetic DNA

<400> SEQUENCE: 48
ggggggttcg ttttcgtttt cgttggggg                                  29
```

```
<210> SEQ ID NO 49
<211> LENGTH: 31
<212> TYPE: DNA
<213> ORGANISM: Artificial sequence
<220> FEATURE:
<223> OTHER INFORMATION: Synthetic DNA

<400> SEQUENCE: 49
gggggggttc gttttcgttt tcgttggggg g                               31
```

```
<210> SEQ ID NO 50
<211> LENGTH: 33
<212> TYPE: DNA
<213> ORGANISM: Artificial sequence
<220> FEATURE:
<223> OTHER INFORMATION: Synthetic DNA

<400> SEQUENCE: 50
ggggggggtt cgttttcgtt ttcgttgggg ggg                             33
```

```
<210> SEQ ID NO 51
<211> LENGTH: 17
<212> TYPE: DNA
<213> ORGANISM: Artificial sequence
<220> FEATURE:
<223> OTHER INFORMATION: Synthetic DNA

<400> SEQUENCE: 51 gggggttcg ttgggggg                                               17
```

```
<210> SEQ ID NO 52
<211> LENGTH: 23
<212> TYPE: DNA
<213> ORGANISM: Artificial sequence
<220> FEATURE:
<223> OTHER INFORMATION: Synthetic DNA

<400> SEQUENCE: 52 gggggttcg ttttcgttgg ggg                                         23
```

```
<210> SEQ ID NO 53
<211> LENGTH: 29
<212> TYPE: DNA
<213> ORGANISM: Artificial sequence
<220> FEATURE:
<223> OTHER INFORMATION: Synthetic DNA

<400> SEQUENCE: 53
ggggggttcg ttttcgtttt cgttggggg                                  29
```

```
<210> SEQ ID NO 54
<211> LENGTH: 35
<212> TYPE: DNA
<213> ORGANISM: Artificial sequence
```

```
<220> FEATURE:
<223> OTHER INFORMATION: Synthetic DNA

<400> SEQUENCE: 54 gggggggttcg ttttcgtttt cgttttcgtt ggggg                                35

<210> SEQ ID NO 55
<211> LENGTH: 41
<212> TYPE: DNA
<213> ORGANISM: Artificial sequence
<220> FEATURE:
<223> OTHER INFORMATION: Synthetic DNA

<400> SEQUENCE: 55 gggggggttcg ttttcgtttt cgttttcgtt ttcgttgggg g                         41

<210> SEQ ID NO 56
<211> LENGTH: 47
<212> TYPE: DNA
<213> ORGANISM: Artificial sequence
<220> FEATURE:
<223> OTHER INFORMATION: Synthetic DNA

<400> SEQUENCE: 56 gggggggttcg ttttcgtttt cgttttcgtt ttcgttttcg ttggggg                   47

<210> SEQ ID NO 57
<211> LENGTH: 23
<212> TYPE: DNA
<213> ORGANISM: Artificial sequence
<220> FEATURE:
<223> OTHER INFORMATION: Synthetic DNA

<400> SEQUENCE: 57 gggggggttcg tcgtcgttgg ggg                                             23

<210> SEQ ID NO 58
<211> LENGTH: 25
<212> TYPE: DNA
<213> ORGANISM: Artificial sequence
<220> FEATURE:
<223> OTHER INFORMATION: Synthetic DNA

<400> SEQUENCE: 58 gggggggttcg ttcgttcgtt ggggg                                           25

<210> SEQ ID NO 59
<211> LENGTH: 27
<212> TYPE: DNA
<213> ORGANISM: Artificial sequence
<220> FEATURE:
<223> OTHER INFORMATION: Synthetic DNA

<400> SEQUENCE: 59 gggggggttcg tttcgtttcg ttgggggg                                        27

<210> SEQ ID NO 60
<211> LENGTH: 29
<212> TYPE: DNA
<213> ORGANISM: Artificial sequence
<220> FEATURE:
<223> OTHER INFORMATION: Synthetic DNA

<400> SEQUENCE: 60 gggggggttcg ttttcgtttt cgttgggggg                                      29
```

<210> SEQ ID NO 61
<211> LENGTH: 31
<212> TYPE: DNA
<213> ORGANISM: Artificial sequence
<220> FEATURE:
<223> OTHER INFORMATION: Synthetic DNA

<400> SEQUENCE: 61 gggggggttcg tttttcgttt tcgttggggg g                                    31

<210> SEQ ID NO 62
<211> LENGTH: 33
<212> TYPE: DNA
<213> ORGANISM: Artificial sequence
<220> FEATURE:
<223> OTHER INFORMATION: Synthetic DNA

<400> SEQUENCE: 62 gggggggttcg tttttttcgtt ttttcgttgg ggg                                 33

<210> SEQ ID NO 63
<211> LENGTH: 27
<212> TYPE: DNA
<213> ORGANISM: Artificial sequence
<220> FEATURE:
<223> OTHER INFORMATION: Synthetic DNA

<400> SEQUENCE: 63
ggggggtcgt tttcgttttc gtggggg                                          27

<210> SEQ ID NO 64
<211> LENGTH: 29
<212> TYPE: DNA
<213> ORGANISM: Artificial sequence
<220> FEATURE:
<223> OTHER INFORMATION: Synthetic DNA

<400> SEQUENCE: 64 gggggggttcg ttttcgtttt cgttggggg                                       29

<210> SEQ ID NO 65
<211> LENGTH: 31
<212> TYPE: DNA
<213> ORGANISM: Artificial sequence
<220> FEATURE:
<223> OTHER INFORMATION: Synthetic DNA

<400> SEQUENCE: 65
ggggggtttc gttttcgttt tcgtttgggg g                                     31

<210> SEQ ID NO 66
<211> LENGTH: 33
<212> TYPE: DNA
<213> ORGANISM: Artificial sequence
<220> FEATURE:
<223> OTHER INFORMATION: Synthetic DNA

<400> SEQUENCE: 66
ggggggtttt cgttttcgtt ttcgttttgg ggg                                   33

<210> SEQ ID NO 67
<211> LENGTH: 27
<212> TYPE: DNA
<213> ORGANISM: Artificial sequence
<220> FEATURE:
<223> OTHER INFORMATION: Synthetic DNA

<400> SEQUENCE: 67 gggggggtcgt tttcgttttc gtggggg                          27

<210> SEQ ID NO 68
<211> LENGTH: 29
<212> TYPE: DNA
<213> ORGANISM: Artificial sequence
<220> FEATURE:
<223> OTHER INFORMATION: Synthetic DNA

<400> SEQUENCE: 68
ggggggttcg ttttcgtttt cgttggggg                         29

<210> SEQ ID NO 69
<211> LENGTH: 31
<212> TYPE: DNA
<213> ORGANISM: Artificial sequence
<220> FEATURE:
<223> OTHER INFORMATION: Synthetic DNA

<400> SEQUENCE: 69
ggggggtttc gttttcgttt cgtttgggg g                       31

<210> SEQ ID NO 70
<211> LENGTH: 33
<212> TYPE: DNA
<213> ORGANISM: Artificial sequence
<220> FEATURE:
<223> OTHER INFORMATION: Synthetic DNA

<400> SEQUENCE: 70
ggggggtttt cgttttcgtt ttcgttttgg ggg                    33

<210> SEQ ID NO 71
<211> LENGTH: 35
<212> TYPE: DNA
<213> ORGANISM: Artificial sequence
<220> FEATURE:
<223> OTHER INFORMATION: Synthetic DNA

<400> SEQUENCE: 71
ggggggtttt tcgttttcgt ttcgttttt ggggg                   35

<210> SEQ ID NO 72
<211> LENGTH: 37
<212> TYPE: DNA
<213> ORGANISM: Artificial sequence
<220> FEATURE:
<223> OTHER INFORMATION: Synthetic DNA

<400> SEQUENCE: 72
ggggggtttt ttcgttttcg ttttcgtttt ttggggg                37

<210> SEQ ID NO 73
<211> LENGTH: 39
<212> TYPE: DNA
<213> ORGANISM: Artificial sequence
<220> FEATURE:
<223> OTHER INFORMATION: Synthetic DNA

<400> SEQUENCE: 73
ggggggtttt tttcgttttc gtttcgttt ttttggggg               39

<210> SEQ ID NO 74

```
<211> LENGTH: 41
<212> TYPE: DNA
<213> ORGANISM: Artificial sequence
<220> FEATURE:
<223> OTHER INFORMATION: Synthetic DNA

<400> SEQUENCE: 74 gggggggtttt ttttcgtttt cgttttcgtt ttttttgggg g                    41

<210> SEQ ID NO 75
<211> LENGTH: 43
<212> TYPE: DNA
<213> ORGANISM: Artificial sequence
<220> FEATURE:
<223> OTHER INFORMATION: Synthetic DNA

<400> SEQUENCE: 75 gggggggtttt ttttttcgttt tcgttttcgt tttttttttgg ggg                43

<210> SEQ ID NO 76
<211> LENGTH: 45
<212> TYPE: DNA
<213> ORGANISM: Artificial sequence
<220> FEATURE:
<223> OTHER INFORMATION: Synthetic DNA

<400> SEQUENCE: 76 gggggggtttt tttttcgtt ttcgttttcg tttttttttt ggggg                 45

<210> SEQ ID NO 77
<211> LENGTH: 23
<212> TYPE: DNA
<213> ORGANISM: Artificial sequence
<220> FEATURE:
<223> OTHER INFORMATION: Synthetic DNA

<400> SEQUENCE: 77
ggggggttcg tcgtcgttgg ggg                                         23

<210> SEQ ID NO 78
<211> LENGTH: 25
<212> TYPE: DNA
<213> ORGANISM: Artificial sequence
<220> FEATURE:
<223> OTHER INFORMATION: Synthetic DNA

<400> SEQUENCE: 78
ggggggttcg ttcgttcgtt ggggg                                       25

<210> SEQ ID NO 79
<211> LENGTH: 27
<212> TYPE: DNA
<213> ORGANISM: Artificial sequence
<220> FEATURE:
<223> OTHER INFORMATION: Synthetic DNA

<400> SEQUENCE: 79
ggggggttcg tttcgtttcg ttgggggg                                    27

<210> SEQ ID NO 80
<211> LENGTH: 29
<212> TYPE: DNA
<213> ORGANISM: Artificial sequence
<220> FEATURE:
<223> OTHER INFORMATION: Synthetic DNA

<400> SEQUENCE: 80
``` gggggggttcg ttttcgtttt cgttggggg                                        29

<210> SEQ ID NO 81
<211> LENGTH: 31
<212> TYPE: DNA
<213> ORGANISM: Artificial sequence
<220> FEATURE:
<223> OTHER INFORMATION: Synthetic DNA

<400> SEQUENCE: 81
ggggggttcg ttttcgttt ttcgttgggg g                                       31

<210> SEQ ID NO 82
<211> LENGTH: 33
<212> TYPE: DNA
<213> ORGANISM: Artificial sequence
<220> FEATURE:
<223> OTHER INFORMATION: Synthetic DNA

<400> SEQUENCE: 82
ggggggttcg tttttcgtt tttcgttgg ggg                                      33

<210> SEQ ID NO 83
<211> LENGTH: 35
<212> TYPE: DNA
<213> ORGANISM: Artificial sequence
<220> FEATURE:
<223> OTHER INFORMATION: Synthetic DNA

<400> SEQUENCE: 83 gggggttcg tttttttcgt tttttcgtt ggggg                                    35

<210> SEQ ID NO 84
<211> LENGTH: 37
<212> TYPE: DNA
<213> ORGANISM: Artificial sequence
<220> FEATURE:
<223> OTHER INFORMATION: Synthetic DNA

<400> SEQUENCE: 84 gggggttcg ttttttttcg ttttttttcg ttggggg                                 37

<210> SEQ ID NO 85
<211> LENGTH: 39
<212> TYPE: DNA
<213> ORGANISM: Artificial sequence
<220> FEATURE:
<223> OTHER INFORMATION: Synthetic DNA

<400> SEQUENCE: 85 gggggttcg ttttttttc gttttttttt cgttggggg                                39

<210> SEQ ID NO 86
<211> LENGTH: 41
<212> TYPE: DNA
<213> ORGANISM: Artificial sequence
<220> FEATURE:
<223> OTHER INFORMATION: Synthetic DNA

<400> SEQUENCE: 86 gggggttcg tttttttttt cgttttttttt ttcgttgggg g                           41

<210> SEQ ID NO 87
<211> LENGTH: 17
<212> TYPE: DNA

```
<213> ORGANISM: Artificial sequence
<220> FEATURE:
<223> OTHER INFORMATION: Synthetic DNA

<400> SEQUENCE: 87 gggggggttcg ttgggg                                                      17

<210> SEQ ID NO 88
<211> LENGTH: 23
<212> TYPE: DNA
<213> ORGANISM: Artificial sequence
<220> FEATURE:
<223> OTHER INFORMATION: Synthetic DNA

<400> SEQUENCE: 88 gggggggttcg ttttcgttgg ggg                                              23

<210> SEQ ID NO 89
<211> LENGTH: 29
<212> TYPE: DNA
<213> ORGANISM: Artificial sequence
<220> FEATURE:
<223> OTHER INFORMATION: Synthetic DNA

<400> SEQUENCE: 89 gggggggttcg ttttcgtttt cgttggggg                                        29

<210> SEQ ID NO 90
<211> LENGTH: 35
<212> TYPE: DNA
<213> ORGANISM: Artificial sequence
<220> FEATURE:
<223> OTHER INFORMATION: Synthetic DNA

<400> SEQUENCE: 90 gggggggttcg ttttcgtttt cgttttcgtt ggggg                                 35

<210> SEQ ID NO 91
<211> LENGTH: 41
<212> TYPE: DNA
<213> ORGANISM: Artificial sequence
<220> FEATURE:
<223> OTHER INFORMATION: Synthetic DNA

<400> SEQUENCE: 91 gggggggttcg ttttcgtttt cgttttcgtt ttcgttgggg g                          41

<210> SEQ ID NO 92
<211> LENGTH: 47
<212> TYPE: DNA
<213> ORGANISM: Artificial sequence
<220> FEATURE:
<223> OTHER INFORMATION: Synthetic DNA

<400> SEQUENCE: 92 gggggggttcg ttttcgtttt cgttttcgtt ttcgttttcg ttggggg                    47

<210> SEQ ID NO 93
<211> LENGTH: 53
<212> TYPE: DNA
<213> ORGANISM: Artificial sequence
<220> FEATURE:
<223> OTHER INFORMATION: Synthetic DNA

<400> SEQUENCE: 93 gggggggttcg ttttcgtttt cgttttcgtt ttcgttttcg ttttcgttgg ggg             53
```

<210> SEQ ID NO 94
<211> LENGTH: 59
<212> TYPE: DNA
<213> ORGANISM: Artificial sequence
<220> FEATURE:
<223> OTHER INFORMATION: Synthetic DNA

<400> SEQUENCE: 94 gggggggttcg ttttcgtttt cgttttcgtt ttcgttttcg ttttcgtttt cgttggggg            59

<210> SEQ ID NO 95
<211> LENGTH: 65
<212> TYPE: DNA
<213> ORGANISM: Artificial sequence
<220> FEATURE:
<223> OTHER INFORMATION: Synthetic DNA

<400> SEQUENCE: 95 gggggggttcg ttttcgtttt cgttttcgtt ttcgttttcg ttttcgtttt cgttttcgtt            60
ggggg                                                                         65

<210> SEQ ID NO 96
<211> LENGTH: 71
<212> TYPE: DNA
<213> ORGANISM: Artificial sequence
<220> FEATURE:
<223> OTHER INFORMATION: Synthetic DNA

<400> SEQUENCE: 96 gggggggttcg ttttcgtttt cgttttcgtt ttcgttttcg ttttcgtttt cgttttcgtt            60
ttcgttgggg g                                                                  71

<210> SEQ ID NO 97
<211> LENGTH: 29
<212> TYPE: DNA
<213> ORGANISM: Artificial sequence
<220> FEATURE:
<223> OTHER INFORMATION: Synthetic DNA

<400> SEQUENCE: 97 gggggggttcg ttttcgtttt cgttggggg                                              29

<210> SEQ ID NO 98
<211> LENGTH: 35
<212> TYPE: DNA
<213> ORGANISM: Artificial sequence
<220> FEATURE:
<223> OTHER INFORMATION: Synthetic DNA

<400> SEQUENCE: 98 gggggggtttc gttttttcgt ttttcgttt ggggg                                        35

<210> SEQ ID NO 99
<211> LENGTH: 41
<212> TYPE: DNA
<213> ORGANISM: Artificial sequence
<220> FEATURE:
<223> OTHER INFORMATION: Synthetic DNA

<400> SEQUENCE: 99 gggggggtttt cgttttttttt cgttttttttt cgttttgggg g                              41

<210> SEQ ID NO 100

```
<211> LENGTH: 47
<212> TYPE: DNA
<213> ORGANISM: Artificial sequence
<220> FEATURE:
<223> OTHER INFORMATION: Synthetic DNA

<400> SEQUENCE: 100 gggggtttt tcgttttttt tttcgttttt tttttcgttt ttggggg                    47

<210> SEQ ID NO 101
<211> LENGTH: 19
<212> TYPE: DNA
<213> ORGANISM: Artificial sequence
<220> FEATURE:
<223> OTHER INFORMATION: Synthetic DNA

<400> SEQUENCE: 101 gggggtttc gtttggggg                                                   19

<210> SEQ ID NO 102
<211> LENGTH: 27
<212> TYPE: DNA
<213> ORGANISM: Artificial sequence
<220> FEATURE:
<223> OTHER INFORMATION: Synthetic DNA

<400> SEQUENCE: 102 gggggtttc gttttttcgt ttggggg                                          27

<210> SEQ ID NO 103
<211> LENGTH: 35
<212> TYPE: DNA
<213> ORGANISM: Artificial sequence
<220> FEATURE:
<223> OTHER INFORMATION: Synthetic DNA

<400> SEQUENCE: 103 gggggtttc gttttttcgt tttttcgttt ggggg                                 35

<210> SEQ ID NO 104
<211> LENGTH: 43
<212> TYPE: DNA
<213> ORGANISM: Artificial sequence
<220> FEATURE:
<223> OTHER INFORMATION: Synthetic DNA

<400> SEQUENCE: 104 gggggtttc gttttttcgt tttttcgttt ttcgtttgg ggg                         43

<210> SEQ ID NO 105
<211> LENGTH: 51
<212> TYPE: DNA
<213> ORGANISM: Artificial sequence
<220> FEATURE:
<223> OTHER INFORMATION: Synthetic DNA

<400> SEQUENCE: 105 gggggtttc gttttttcgt tttttcgttt ttcgttttt tcgtttgggg g                51

<210> SEQ ID NO 106
<211> LENGTH: 59
<212> TYPE: DNA
<213> ORGANISM: Artificial sequence
<220> FEATURE:
<223> OTHER INFORMATION: Synthetic DNA

<400> SEQUENCE: 106
```

```
gggggggtttc gttttttcgt tttttcgttt tttcgttttt tcgttttttc gtttggggg       59
```

<210> SEQ ID NO 107
<211> LENGTH: 29
<212> TYPE: DNA
<213> ORGANISM: Artificial sequence
<220> FEATURE:
<223> OTHER INFORMATION: Synthetic DNA

<400> SEQUENCE: 107

```
gggggggttcg ttttgctttt gcttggggg                                         29
```

<210> SEQ ID NO 108
<211> LENGTH: 29
<212> TYPE: DNA
<213> ORGANISM: Artificial sequence
<220> FEATURE:
<223> OTHER INFORMATION: Synthetic DNA

<400> SEQUENCE: 108

```
gggggggttcg tgttgctgtt gctggggggg                                        29
```

<210> SEQ ID NO 109
<211> LENGTH: 29
<212> TYPE: DNA
<213> ORGANISM: Artificial sequence
<220> FEATURE:
<223> OTHER INFORMATION: Synthetic DNA

<400> SEQUENCE: 109

```
gggggggttcg tattgctatt gctaggggg                                         29
```

<210> SEQ ID NO 110
<211> LENGTH: 29
<212> TYPE: DNA
<213> ORGANISM: Artificial sequence
<220> FEATURE:
<223> OTHER INFORMATION: Synthetic DNA

<400> SEQUENCE: 110

```
gggggggttcg tcttgctctt gctcggggg                                         29
```

<210> SEQ ID NO 111
<211> LENGTH: 29
<212> TYPE: DNA
<213> ORGANISM: Artificial sequence
<220> FEATURE:
<223> OTHER INFORMATION: Synthetic DNA

<400> SEQUENCE: 111

```
gggggggtcg ttgtcgttgt cgttggggg                                          29
```

<210> SEQ ID NO 112
<211> LENGTH: 29
<212> TYPE: DNA
<213> ORGANISM: Artificial sequence
<220> FEATURE:
<223> OTHER INFORMATION: Synthetic DNA

<400> SEQUENCE: 112

```
ggggggggtcg tggtcgtggt cgtggggggg                                        29
```

<210> SEQ ID NO 113
<211> LENGTH: 29
<212> TYPE: DNA

<213> ORGANISM: Artificial sequence
<220> FEATURE:
<223> OTHER INFORMATION: Synthetic DNA

<400> SEQUENCE: 113
gggggggtcg tagtcgtagt cgtaggggg                                29

<210> SEQ ID NO 114
<211> LENGTH: 29
<212> TYPE: DNA
<213> ORGANISM: Artificial sequence
<220> FEATURE:
<223> OTHER INFORMATION: Synthetic DNA

<400> SEQUENCE: 114
gggggggtcg tcgtcgtcgt cgtcggggg                                29

<210> SEQ ID NO 115
<211> LENGTH: 29
<212> TYPE: DNA
<213> ORGANISM: Artificial sequence
<220> FEATURE:
<223> OTHER INFORMATION: Synthetic DNA

<400> SEQUENCE: 115 gggggatcg ttatcgttat cgttggggg                                 29

<210> SEQ ID NO 116
<211> LENGTH: 29
<212> TYPE: DNA
<213> ORGANISM: Artificial sequence
<220> FEATURE:
<223> OTHER INFORMATION: Synthetic DNA

<400> SEQUENCE: 116 gggggctcg ttctcgttct cgttggggg                                 29

<210> SEQ ID NO 117
<211> LENGTH: 29
<212> TYPE: DNA
<213> ORGANISM: Artificial sequence
<220> FEATURE:
<223> OTHER INFORMATION: Synthetic DNA

<400> SEQUENCE: 117 gggggttcg ttttcgtttt cgttggggg                                 29

<210> SEQ ID NO 118
<211> LENGTH: 17
<212> TYPE: DNA
<213> ORGANISM: Artificial sequence
<220> FEATURE:
<223> OTHER INFORMATION: Synthetic DNA

<400> SEQUENCE: 118 gggggttcg taggggg                                              17

<210> SEQ ID NO 119
<211> LENGTH: 23
<212> TYPE: DNA
<213> ORGANISM: Artificial sequence
<220> FEATURE:
<223> OTHER INFORMATION: Synthetic DNA

<400> SEQUENCE: 119 gggggttcg tattcgtagg ggg                                       23

<210> SEQ ID NO 120
<211> LENGTH: 29
<212> TYPE: DNA
<213> ORGANISM: Artificial sequence
<220> FEATURE:
<223> OTHER INFORMATION: Synthetic DNA

<400> SEQUENCE: 120 gggggggttcg tattcgtatt cgtaggggg                              29

<210> SEQ ID NO 121
<211> LENGTH: 35
<212> TYPE: DNA
<213> ORGANISM: Artificial sequence
<220> FEATURE:
<223> OTHER INFORMATION: Synthetic DNA

<400> SEQUENCE: 121 gggggggttcg tattcgtatt cgtattcgta ggggg                       35

<210> SEQ ID NO 122
<211> LENGTH: 41
<212> TYPE: DNA
<213> ORGANISM: Artificial sequence
<220> FEATURE:
<223> OTHER INFORMATION: Synthetic DNA

<400> SEQUENCE: 122 gggggggttcg tattcgtatt cgtattcgta ttcgtagggg g                41

<210> SEQ ID NO 123
<211> LENGTH: 47
<212> TYPE: DNA
<213> ORGANISM: Artificial sequence
<220> FEATURE:
<223> OTHER INFORMATION: Synthetic DNA

<400> SEQUENCE: 123 gggggggttcg tattcgtatt cgtattcgta ttcgtattcg taggggg          47

<210> SEQ ID NO 124
<211> LENGTH: 17
<212> TYPE: DNA
<213> ORGANISM: Artificial sequence
<220> FEATURE:
<223> OTHER INFORMATION: Synthetic DNA

<400> SEQUENCE: 124 gggggggttcg tcggggg                                           17

<210> SEQ ID NO 125
<211> LENGTH: 23
<212> TYPE: DNA
<213> ORGANISM: Artificial sequence
<220> FEATURE:
<223> OTHER INFORMATION: Synthetic DNA

<400> SEQUENCE: 125 gggggggttcg tcttcgtcgg ggg                                    23

<210> SEQ ID NO 126
<211> LENGTH: 29
<212> TYPE: DNA
<213> ORGANISM: Artificial sequence
<220> FEATURE:

<223> OTHER INFORMATION: Synthetic DNA

<400> SEQUENCE: 126 gggggggttcg tcttcgtctt cgtcggggg                                          29

<210> SEQ ID NO 127
<211> LENGTH: 35
<212> TYPE: DNA
<213> ORGANISM: Artificial sequence
<220> FEATURE:
<223> OTHER INFORMATION: Synthetic DNA

<400> SEQUENCE: 127 gggggggttcg tcttcgtctt cgtcttcgtc ggggg                                   35

<210> SEQ ID NO 128
<211> LENGTH: 41
<212> TYPE: DNA
<213> ORGANISM: Artificial sequence
<220> FEATURE:
<223> OTHER INFORMATION: Synthetic DNA

<400> SEQUENCE: 128 gggggggttcg tcttcgtctt cgtcttcgtc ttcgtcgggg g                            41

<210> SEQ ID NO 129
<211> LENGTH: 47
<212> TYPE: DNA
<213> ORGANISM: Artificial sequence
<220> FEATURE:
<223> OTHER INFORMATION: Synthetic DNA

<400> SEQUENCE: 129 gggggggttcg tcttcgtctt cgtcttcgtc ttcgtcttcg tcggggg                      47

<210> SEQ ID NO 130
<211> LENGTH: 29
<212> TYPE: DNA
<213> ORGANISM: Artificial sequence
<220> FEATURE:
<223> OTHER INFORMATION: Synthetic DNA

<400> SEQUENCE: 130 gggggggttcg ttttcgtttt cgttggggg                                          29

<210> SEQ ID NO 131
<211> LENGTH: 29
<212> TYPE: DNA
<213> ORGANISM: Artificial sequence
<220> FEATURE:
<223> OTHER INFORMATION: Synthetic DNA

<400> SEQUENCE: 131 gggggggggcg ttggcgttgg cgttggggg                                          29

<210> SEQ ID NO 132
<211> LENGTH: 29
<212> TYPE: DNA
<213> ORGANISM: Artificial sequence
<220> FEATURE:
<223> OTHER INFORMATION: Synthetic DNA

<400> SEQUENCE: 132 gggggggaacg ttaacgttaa cgttgggggg 29

<210> SEQ ID NO 133
<211> LENGTH: 29
<212> TYPE: DNA
<213> ORGANISM: Artificial sequence
<220> FEATURE:
<223> OTHER INFORMATION: Synthetic DNA

<400> SEQUENCE: 133 gggggggcccg ttcccgttcc cgttgggggg 29

<210> SEQ ID NO 134
<211> LENGTH: 29
<212> TYPE: DNA
<213> ORGANISM: Artificial sequence
<220> FEATURE:
<223> OTHER INFORMATION: Synthetic DNA

<400> SEQUENCE: 134 gggggggttcg ggttcgggtt cggggggggg 29

<210> SEQ ID NO 135
<211> LENGTH: 29
<212> TYPE: DNA
<213> ORGANISM: Artificial sequence
<220> FEATURE:
<223> OTHER INFORMATION: Synthetic DNA

<400> SEQUENCE: 135 gggggggttcg aattcgaatt cgaagggggg 29

<210> SEQ ID NO 136
<211> LENGTH: 29
<212> TYPE: DNA
<213> ORGANISM: Artificial sequence
<220> FEATURE:
<223> OTHER INFORMATION: Synthetic DNA

<400> SEQUENCE: 136 gggggggttcg ccttcgcctt cgccgggggg 29

<210> SEQ ID NO 137
<211> LENGTH: 16
<212> TYPE: DNA
<213> ORGANISM: Artificial sequence
<220> FEATURE:
<223> OTHER INFORMATION: Synthetic DNA

<400> SEQUENCE: 137
tctctttctt tttctt 16

<210> SEQ ID NO 138
<211> LENGTH: 23
<212> TYPE: DNA
<213> ORGANISM: Artificial sequence
<220> FEATURE:
<223> OTHER INFORMATION: Synthetic DNA

<400> SEQUENCE: 138
tcgtcgtttt gtcgtttgtc gtt 23

IMMUNOSTIMULATORY OLIGODEOXYNUCLEOTIDES

CROSS-REFERENCE TO RELATED APPLICATIONS

This application is a national stage entry under 35 U.S.C. §371 of PCT/EP2011/074211, filed on Dec. 29, 2011, which claims priority to U.S. Provisional Application No. 61/430,301, filed on Jan. 6, 2011; and EP Application No. 10197435.0, filed on Dec. 30, 2010. The content of PCT/EP2011/074211 is hereby incorporated by reference in its entirety.

REFERENCE TO SEQUENCE LISTING SUBMITTED ELECTRONICALLY

The sequence listing of the present application is submitted electronically via EFS-Web as an ASCII formatted sequence listing with a file name "2010031USPCT_SEQTXT_26 Jun. 2013", creation date of Jun. 17, 2013, and a size of 24 KB. This sequence listing submitted via EFS-Web is part of the specification and is herein incorporated by reference in its entirety.

The present invention relates to immunostimulatory oligodeoxynucleotides, vectors and vaccines comprising such oligodeoxynucleotides, to their use as a medicament, to their use in preventing or combating infectious disease, to methods for the detection of such oligodeoxynucleotides and to cells to be used in these methods.

During the past two decades, it has emerged in immunological science that the vertebrate immune system possesses mechanisms to detect microbial infection and to trigger rapid immune activation via the receptor-mediated recognition of unique characteristics of pathogens, the so-called pathogen-associated molecular patterns (PAMPs) interacting with cognate host pathogen recognition receptors (PRRs) (Iwasaki A, Medzhitov R. 2001. *Science* 327, 291-295. Medzhitov R., 2009. *Immunity* 30, 766-775).

It is now clear that certain forms of pathogen deoxyribonucleic acid (DNA) are amongst these PAMPs. In 1995 it was reported that non-methylated CpG motifs in bacterial DNA trigger murine B-cell activation (Krieg et al. 1995). This study generated for the first time a link between the specific recognition of bacterial immunostimulatory non-methylated CpG-containing DNA and the previously recognized CpG suppression as well as the widespread CpG methylation in mammalian DNA. The most effective B cell stimulatory non-methylated CpG oligodeoxynucleotide (CpG ODN) was shown to possess the sequence element GACGTT.

The next landmark paper in the field was published by Shizuo Akira's laboratory in Osaka/Japan (Hemmi et al. 2000). By a gene cloning and a targeted gene knockout approach in mice it could be unequivocally shown, that the cellular response in mice to CpG-ODNs is mediated by the toll-like receptor 9 (TLR9). Subsequently it was shown that the CpG-ODNs are agonists for TLR9 signaling predominantly via the NF kappa-B pathway (Medzhitov 2001). In the following decade, quite a number of studies have been published on basic research topics and on general potential immunotherapeutic applications (e.g. reviewed in Krieg 2002, 2003, 2006; Klinman 2004, Vollmer 2005, Wilson et al. 2006, Kindrachuk et al. 2008, Dorn and Kippenberger 2008, Vollmer and Krieg 2009, Wilson et al. 2009). A number of review articles focus on anti-infective applications of CpG-ODNs (Krieg 2007), the use of TLR9 agonists in the treatment of cancer (Krieg 2007, Weiner 2009), TLR9 activation for asthma and allergy treatment (Kline 2007, Kline and Krieg 2008, Fonseca and Kline 2009) and as vaccine adjuvants (Klinman et al. 2004, Klinman 2006, Daubenberger 2007, Wagner 2009, Mutwiri et al. 2009, Klinman et al. 2009).

CpG ODNs have also been described and discussed as immunostimulatory agents and vaccine adjuvants in veterinary applications, particularly in bovines, pigs, sheep, dogs, chicken and fish (Babiuk et al. 2003, Carrington and Secombes 2006, Griebel et al. 2005, Mutwiri et al. 2003, Singh and O'Hagan 2003, Werling and Jungi 2003).

In the field of veterinary uses in chickens, the use of CpG oligodeoxynucleotides in e.g. vaccines to protect chickens against Newcastle Disease has been described (Linghua 2007).

It has recently been shown that in chicken, TLR21 acts as a functional homologue to mammalian TLR9 in the recognition of CpG oligodeoxynucleotides (Brownlie et al., 2009).

The design of specific CpG ODN's as immunomodulators has so far been quite random. This is especially true for non-mammalian CpG ODN's. The reason for this is multifactorial; first of all there is no knowledge about correlation between immuno modulatory CpG motifs for human TLR's and for TLR's in non-human, let alone non-mammalian species. Secondly, there are no cell-systems available with a sufficiently low background to noise level to selectively test the effects of very low concentrations of CpG ODN's. Moreover, there are no high-throughput screening methods available and even if there were, there is no clear correlation between in vivo versus in vitro efficacy of CpG ODN's as immuno-modulators in non-mammalian species.

Thus, there clearly is a need for novel CpG ODN's that have a high immuno-modulatory effect and therefore are effective in low doses. And there is a need for selective and sensitive CpG ODN selection systems for veterinary purposes that show a correlation between in vitro and in vivo activity of CpG-activity.

It is one of the objectives of the present invention to provide such novel CpG ODN's.

In this respect, one embodiment of the present invention relates to an immunostimulatory non-methylated oligodeoxynucleotide having the general formula

wherein
each $N_1$ is independently C or G; each $N_2$ is independently C or G; $N_3$ is T, C or G, with the proviso that the combination wherein N3 and N4 are both C is excluded; each $N_4$ and $N_5$ are independently C or T; $N_6$=A, T, G or C; $N_7$=A, T, C or G; $N_8$=A, T, C or G; x=3-10; z=0-10; n=2-100; p=1-6, or 1-25 if $N_4$=T; q=1-6, or 1-25 if $N_5$=T; r=0-8, or 1-25 if $N_7$=T and s=0-8, or 1-25 if $N_8$=T, or a pharmaceutically acceptable salt of said oligodeoxynucleotide.

An "immunostimulatory non-methylated oligodeoxynucleotide" refers to an oligodeoxynucleotide, which contains a non-methylated cytidine-phosphate-guanosine di-nucleotide sequence that stimulates the initiation of signaling cascades leading to activation of transcription factors such as NF-κB or Interferon Regulatory Factor 3 (IRF3). It is this activation that in turn results in the expression of inflammatory cytokines and other cellular activation events. NF-κB binding sites and gene expression influenced by NF-κB are i.a. described by Schindler and Baichwal (1994).

The term oligodeoxynucleotide means a short nucleic acid polymer of deoxynucleotides; i.e. a molecule comprising a multitude of deoxyriboses, linked to a phosphate group and to an exchangeable organic base. Such an organic base is a substituted pyrimidine or a substituted purine. Examples are cytosine and thymine respectively adenine and guanine.

The oligonucleotides according to the invention may comprise modifications. Examples of such modifications are e.g. modifications in the phosphodiester internucleoside bridge located at the 3' and/or 5' end of a nucleoside. Such modifications relate i.a. to the replacement of a phosphodiester by e.g. a phosphorothioate or a phosphorodithioate.

Other modifications are e.g. replacements of a phosphodiester bridge by a dephospho bridge. Examples of dephospho bridges are methylhydroxylamine, formacetal and dimethylenesulfone groups.

Still other modifications are modifications that concern the replacement of a natural nucleoside base by a non-natural nucleoside base such as 5-fluorocytosine, 7-deaza-7-substituted guanine, 7-deaza-8-substituted guanine, 2-thiouracil, dihydrouracil, 5-bromo-cytosine, 6-substituted cytosines, N4-substituted cytosines, Again other modifications are modifications concerning the replacement of a sugar unit; a β-ribose sugar or a β-D-2'-ribose sugar unit by a modified sugar unit such as e.g. an L-2'-deoxyribose or 2'-L-arabinose.

A text book giving further insight in oligonucleotides is e.g. "PCR Primer: A Laboratory Manual", Second Edition, 2003, Edited By Carl W. Dieffenbach, *National Institute of Allergy and Infectious Diseases*; Gabriela S. Dreksler, *Uniformed Services University of the Health Sciences*, Cold Spring Harbor Laboratory Press ISBN 978-087969654-2.

The structure $\{N_3[N_4]_p \text{ C G } [N_5]_q N_6\}_n$ carrying the CpG motif represents the active immunostimulating moiety of an ODN according to the invention. Therefore, the present invention provides immunostimulatory oligodeoxynucleotides that comprise this so-called "backbone".

It was found that the backbone of an oligodeoxynucleotide according to the invention, the structure $\{N_3[N_4]_p \text{ C G } [N_5]_q N_6\}_n$ must be present at least two, preferably three times. Therefore, n should be at least two. It was also found that the activity of the oligodeoxynucleotides increases when n increases. This effect is leveling when n increases. Basically, the number n of the backbone structure should therefore be at least 2. Preferably, the range of n is $3 \leq n \leq 100$, merely because of the fact that the longer the synthetic sequence the more difficult it is to make. In practice preferably the range of n is $2 \leq n \leq 18$. More preferably, the range of n is $3 \leq n \leq 18$, even more preferably the range of n is $4 \leq n \leq 18$, still even more preferably the range of n is $5 \leq n \leq 18$.

The identification of CpG ODN's according to the invention was made possible i.a. by using a more selective detection system than the systems currently in use for the detection of NF-κB activation. Brownlie at al. (2009) describe an NF-κB luciferase based reporter system. Other systems are e.g. based upon IL-8 transcript measurement or cytokine secretion or the detection of NO secretion.

Contrary to this, in the present invention a secreted alkaline phosphatase based detection system (SEAP) was used. SEAP is a reporter enzyme in mammalian systems (Yang et al., 1997). This system turned out to be surprisingly sensitive and in addition surprisingly provides a close correlation between the in vitro and in vivo activities of the CpG ODN's tested. The SEAP system was used with para-nitrophenylphosphate (pNPP) as a substrate.

Another improvement over existing systems was the introduction and stable maintenance in cells of the plasmid carrying the SEAP gene. Up till now, all detection systems used transient transfection of cells with the reporter gene. It is due to the introduction and stable maintenance in cells of the reporter gene that now for the first time a dose/response curve could be made. Such a curve is essential if a reliable comparison between various CpG ODN's activity is to be made.

Therefore, the methods and cell lines described in detail in the Examples section of the present invention allow for the first time to make a reliable side-by-side comparison between various CpG ODN's.

Further details of the system used are given in the Examples section.

Since the present methods and cell lines now allow such reliable side-by-side comparisons between various CpG ODN's, it could be determined that an oligodeoxynucleotide according to the invention wherein $N_6$=A, T or C has a higher activity level than when $N_6$=G. Therefore, in a preferred form of this embodiment, $N_6$=A, T or C.

For the same reason, in another preferred form $N_3$ is T or G; and $N_6$=Y(Y=C or T).

In a more preferred form of this embodiment, $N_3$, $N_4$, $N_5$ and $N_6$=T.

Another preferred form of this embodiment relates to an oligodeoxynucleotide according to the invention wherein $N_3$, $N_4$ and $N_5$=T and $N_6$=C Still another preferred form of this embodiment relates to an oligodeoxynucleotide according to the invention wherein $N_3$ is G and $N_6$=T Again another preferred form of this embodiment relates to an oligodeoxynucleotide according to the invention wherein $N_5$=T and $N_6$=C Also, a preferred form of this embodiment relates to an oligodeoxynucleotide according to the invention wherein $N_5$=C, $N_6$=C and q=1

Another preferred form of this embodiment relates to an oligodeoxynucleotide according to the invention wherein $N_4$=Y and $N_5$=Y.

A more preferred form of this last embodiment relates to an oligodeoxynucleotide according to the invention wherein $N_4$=T and $N_5$=Y.

An even more preferred form of this last embodiment relates to an oligodeoxynucleotide according to the invention wherein $N_4$=T and $N_5$=T.

Another form of this embodiment relates to an oligodeoxynucleotide according to the invention wherein x is 4-7 and r=0 or $N_7$ is A or T.

In a preferred form of this embodiment relates to an oligodeoxynucleotide according to the invention wherein x is 6 and r=0 or $N_7$ is A or T.

Another form of this embodiment relates to an oligodeoxynucleotide according to the invention wherein z is 0-6 and s=0 or $N_8$ is A or T.

In a preferred form of this embodiment relates to an oligodeoxynucleotide according to the invention wherein z is 0-3 and s=0 or $N_8$ is A or T.

In again another form of this embodiment, $N_1$ is G.

In a preferred form of this embodiment, $N_2$ is G.

Although there exists a broad range for both the number of the 3'- and the 5'-terminal nucleotides, it was found that there exists an optimum range for both values. It was found that if s=0 or $N_8$ is A or T, the number of $[N_2]$ nucleotides that forms the 3'-flanking region of the backbone of the oligodeoxynucleotide according to the invention preferably ranges between 0 and 5 nucleotides, more preferably between 0 and 3 nucleotides.

It was also found that if r=0 or $N_7$ is A or T, the number of $[N_1]$ nucleotides that forms the 5'-flanking region of the backbone of the oligodeoxynucleotide according to the invention has an optimum in the region between 4 and 7 nucleotides.

In a most preferred form of this embodiment, r=0 or $N_7$ is A or T, and s=0 or $N_8$ is A or T, and n=5-18 and x=4-7 and z=0-3.

As said above, several kinds of modifications in the phosphodiester internucleoside bridge located at the 3' and/or 5' end of a nucleoside are feasible. But basically, depending upon the way of synthesis, usual common types of bonds between two nucleotides are: phosphodiester (PDE) bonds and phosphorothioate (PTO) bonds. In order to improve the stability and the immunostimulatory effect of CpG ODN's, the building blocks of synthetic oligodeoxynucleotides are provided with phosphorothioates, so that they form PTO bonds.

It was surprisingly found, however, that when only the $[N_1]$ nucleotides and the $[N_2]$ nucleotides are bound by PTO bonds and the other nucleotides are bound by PDE bonds, the efficacy of the oligodeoxynucleotide according to the invention is strongly increased. (In such cases, the N1 to N7 bond (GT) is a PTO, while the N8 to N2 (TG) bond is a PDE.)

This is especially the case when the $[N_1]$ and $[N_2]$ nucleotides are G's.

Therefore, another preferred form of this embodiment relates to oligodeoxynucleotides according to the invention wherein the $N_1$'s and/or the $N_2$'s have a phosphorothioate binding and the other nucleotides have a phosphodiester binding.

It was found that for oligodeoxynucleotides according to the invention an even more effective oligodeoxynucleotide is obtained when $N_7$=T and $N_8$=T, Thus, again another preferred form of this embodiment relates to oligodeoxynucleotides according to the invention wherein $N_7$=T and $N_8$=T. In this case, r and s are independently between 1-25.

It is not necessary that the backbone of oligodeoxynucleotides according to the invention, the structure $\{N_3[N_4]_p C G [N_5]_q N_6\}_n$ is identical for every n. This means that an oligodeoxynucleotide according to the invention could look i.a. like this: $\{T T C G T T\} \{C T C G T G\} \{G T C G T A\}$. Such a series of three different consecutive different backbones would be indicated as a heteropolymer. A stretch of three identical copies would be called a homopolymer.

Preferably, the oligodeoxynucleotide according to the invention comprises a $\{N_3[N_4]_p C G [N_5]_q N_6\}$ homopolymer.

The CpG oligodeoxynucleotides according to the invention are in most cases active in nanomolar amounts, both in the in vitro test system and in vivo. However some of the CpG oligodeoxynucleotides according to the invention are even active in picomolar (sub-nanomolar) amounts; their EC50 is below 1 nM.

The half-maximal effective concentration (EC50) of an oligodeoxynucleotide is the amount of oligodeoxynucleotide that is necessary to induce an amount of the reporter enzyme SEAP (that produces the colored product absorbing at 405 nm) in the reporter cells (HEK293-pNifty2-chickenTLR21 or HD11-pNifTy2Hyg) that gives a half-maximal absorption. If the EC50 of an oligodeoxynucleotide is below 1 nM in these cells, it is considered to be active in picomolar (sub-nanomolar) amounts.

Most of the CpG ODN's that fit in one of the four general formulae listed below were shown to trigger an in vitro effect in nanomolar amounts:

1) $^{5'}[G]_x \{T T C G T N_6\}_n[G]_z^{3'}$ wherein $N_6$=A or T, n=5-100, x=3-10, z=0-10

2) $^{5'}[G]_x \{N_3 T C G T C\}_n[G]_z^{3'}$ wherein $N_3$=G or T, n=5-100, x=3-10, z=0-10

3) $^{5'}[G]_x \{T T C G C C\}_n[G]_z^{3'}$ wherein n=5-100, x=3-10, z=0-10

4) $^{5'}[G]_x \{T [T]_p C G [T]_q T\}_n[G]_z^{3'}$ wherein p=1-10, q=1-10, n=5-100, x=3-10, z=0-10

For all of these four formulae, for reasons of cost effectiveness, n is preferably in the range of 5-18. X is preferably in the range of 4-9, 5-8, 6 or 7 in that order of preference, and z is preferably 8, 7, 6, 5, 4, 3, 2, 1 or 0 in that order of preference. Where applicable, p is preferably 1-5 and q is preferably 1-5.

It is very well possible to link an oligodeoxynucleotide according to the invention to a carrier or hapten, via a reactive chemical group. Such linkage enhances the immunostimulatory effect of the combined molecules.

Mere examples of such components are e.g. digoxigenin, aminohexyl-, Texas red and biotin. Preferred carriers or haptens are 3'- and 5'-labeled Texas red and 5'-labeled digoxigenin. The linkage of oligodeoxynucleotides to haptens/carriers is well-known in the art.

Another embodiment of the invention relates to a vector comprising an immunostimulatory non-methylated oligodeoxynucleotide according to the invention. Such a vector can be a nucleic acid molecule such as a plasmid, a virus, a bacteriophage or any other vector used in molecular biology. Merely as an example: a vector comprising an immunostimulatory non-methylated oligodeoxynucleotide can e.g. be a DNA molecule such as a plasmid that can be multiplied in bacteria, into which an immunostimulatory non-methylated oligodeoxynucleotide according to the invention has been cloned. Such a plasmid preferably has an active origin of replication, causing high numbers of the plasmid to be present in the host. Growing such bacteria on a large scale followed by isolation of the plasmids provides an alternative for the synthetic production of the immunostimulatory non-methylated oligodeoxynucleotide according to the invention.

One of the aims of the present invention is to provide new CpG ODN's that can be used as successful immunostimulating components in vaccines that prevent or combat infectious disease together with an antigen component or genetic information encoding an antigen component, and a pharmaceutically acceptable carrier.

In general, the term antigen component refers to a composition of matter that comprises at least one epitope that can induce, stimulate or enhance an immune response when administered to a human or an animal.

The antigen component may be any kind of antigen component but preferably is derived from a micro-organism or virus that in its wild-type form is pathogenic to humans or animals.

The antigen component can be the whole pathogen, preferably in an inactivated or attenuated form, an extract of the pathogen or an immunogenic protein of the pathogen.

If the antigen component is an immunogenic protein of the pathogen, that immunogenic protein is preferably expressed in and recovered from in vitro cultured cells.

Therefore, another embodiment relates to a vaccine for preventing or combating infectious disease characterised in that said vaccine comprises an immunostimulating amount of an oligodeoxynucleotide according to the invention and/or a vector according to the invention, an immunogenic amount of an antigen component or genetic information encoding an antigen component, and a pharmaceutically acceptable carrier.

Of course, the immunostimulating amount of the oligodeoxynucleotide and the immunogenic amount of the antigen component are strongly interrelated. It is one of the merits of the present invention that the presence of the oligodeoxynucleotide according to the invention can lower the amount of antigen component that is necessary to prevent or combat infectious disease.

The amount of antigen component that is necessary to prevent or combat infectious disease is referred to as the immunogenic amount of the antigen component.

An immunostimulating amount of the oligodeoxynucleotide is the amount that is capable of decreasing the immunogenic amount of the antigen component, i.e. the amount of the antigen component that is necessary to prevent or combat an infectious disease.

So basically, the wording "immunostimulating amount of the oligodeoxynucleotide" and "immunogenic amount" must be seen in relation to each other.

It goes without saying that, if the vaccine comprises genetic information encoding an antigen component, the amount of antigen component expressed by this genetic information should be enough to prevent or combat infectious disease, i.e.; it must be an immunogenic amount.

The fact that the non-methylated oligodeoxynucleotides according to the invention are immunostimulatory, means that they enhance the immunological efficacy of antigen components in vaccines. For that reason, vaccines according to the invention will in many cases comprise less of the antigen component or the genetic information encoding the antigen component than would be the case if no oligodeoxynucleotides according to the invention would be present.

In some cases an antigen component as such, without the addition of immunostimulatory oligonucleotides, may have such low immunogenic properties that high amounts must be given anyway, albeit without reaching the desired immunogenic level. In such cases, the antigen component can be given in the usual high concentration, however now together with an oligodeoxynucleotide according to the invention in order to so obtain the desired level of immunogenicity.

Thus, the amount of the antigen component or the genetic information encoding the antigen component to be administered with a oligonucleotide according to the invention would as a rule of thumb be equal or below the amount given in the absence of the oligonucleotide. The skilled person involved in the manufacturing of a specific vaccines, would know that amount for that specific vaccine. Also, the Examples give e.g. ample guidance for the amount of antigen components to be used, e.g. in three different inactivated viral vaccines: Newcastle disease virus vaccine, Infectious Bronchitis virus vaccine and Turkey Rhinotracheitis vaccine.

The amount of the oligodeoxynucleotide according to the invention that needs to be administered together with the antigen component or the genetic information encoding the antigen component depends both on the selected oligodeoxynucleotide and the antigen component.

A very suitable amount of oligodeoxynucleotide according to the invention would usually vary between 1 and 100 nanomol. Very good in vivo results have e.g. been obtained with 1-10 μg of oligodeoxynucleotides according to the invention with an average length of 30 deoxynucleotides that were shown to be active in in vitro tests in the nanomolar range.

If an oligodeoxynucleotide is chosen from the group of oligodeoxynucleotides that are active in the picomolar range, the skilled person would realise that amounts below, possibly far below, 1 nanomol, i.e. picomolar amounts, would be worth testing before testing nanomolar amounts.

Vaccines according to the invention comprise a pharmaceutically acceptable carrier. The nature of this carrier depends i.a. upon the route of administration. If the administration route is through the oral or intranasal route, the carrier could be as simple as sterile water, a physiological salt solution or a buffer. If injection is the preferred route, the carrier should preferably be isotonic and have pH restrictions that make it suitable for injection. Such carriers however are extensively known in the art.

Vaccines according to the invention may, in addition to the antigen component or the genetic information encoding the antigen component, and an oligodeoxynucleotide according to the invention, comprise an adjuvant. Adjuvants in general are substances that boost the immune response of the host in a non-specific manner.

Many adjuvants are known in the art to be suitable, such as Freund's Complete and Incomplete adjuvant, vitamin E, non-ionic block polymers and polyamines such as dextran sulphate, carbopol and pyran, alum hydroxide. Also frequently used are alumin phosphate, saponins, vegetable oils such as tocopherol and mineral oils. Very efficient adjuvants are oil-in-water emulsions and especially water-in-oil emulsions, further also referred to as are oil-in-water adjuvants and water-in-oil adjuvants. Such emulsions are well-known in the art. Thus, preferably, the vaccine comprises a water-in-oil adjuvant.

Preferably the antigen component is, or is derived from a virus or micro-organism that in its wild-type form is pathogenic to poultry.

More preferably, said virus or micro-organism is selected from the group consisting of Infectious Bronchitis virus, Newcastle Disease virus, Infectious Bursal Disease (Gumboro), Chicken Anaemia agent, Avian Reovirus, *Mycoplasma gallisepticum*, Turkey Rhinotracheitis virus, *Haemophilus paragallinarum* (Coryza), Chicken Poxvirus, Avian Encephalomyelitis virus, Egg Drop syndrome virus, Infectious Laryngotracheitis virus, Herpes Virus of Turkeys, *Eimeria* species, *Ornithobacterium rhinotracheale, Pasteurella multocida, Mycoplasma synoviae, Salmonella* species and *Escherichia coli*.

Again another embodiment of the present invention relates to an immunostimulatory non-methylated oligodeoxynucleotide according to the invention for use as a medicament Again another embodiment of the present invention relates to an immunostimulatory non-methylated oligodeoxynucleotide according to the invention for use in preventing or combating infectious disease in poultry Up till now, all detection systems used transient transfection of cells with the reporter gene. Such transient systems do not allow for a reliable side-by-side comparison of the efficacy of CpG ODN's. As said above, a major improvement over existing systems was the introduction and stable maintenance in cells, of the plasmid carrying the reporter gene. Stable means that the plasmid remains present in the cell after several cell division cycles.

Frequently, stable maintenance of a plasmid is obtained by growing the cells under the pressure of one or more selective agents, such as antibiotics for which a resistance gene is present on the plasmid. Loss of the plasmid would then cause the cell that lost the plasmid to die. Remaining viable cells would still harbour the plasmid.

Thus, still another embodiment of the present invention relates to a cell comprising a TLR21-receptor and a plasmid encoding an NF-κB reporter gene, which plasmid is stably maintained in the cell. Such cells are very suitable for use in the screening of CpG molecules, more specifically the screening of CpG molecules according to the invention.

The Examples give ample guidance about how to obtain such a cell comprising a plasmid encoding a reporter gene that can be stably maintained in the cell.

As also mentioned above, detection systems based upon secreted alkaline phosphatase (SEAP) were shown to be very suitable for the detection system used.

Thus, preferably the reporter gene is a gene encoding secreted alkaline phosphatase.

Basically, any cell or cell line carrying a TLR21 that allows introduction and preferably the stable maintenance of a plasmid carrying a NF-κB reporter gene, preferably the SEAP gene as described above is suitable for testing TLR21-specific CpG ODN's.

A preferred example of such a suitable cell line for testing TLR21-specific CpG ODN's is the chicken cell line HD11.

Therefore, preferably, a cell line for use in the detection system is a HD11 cell line comprising a stable plasmid encoding a reporter gene.

Chicken cell lines such as the HD11 cell line display a whole panel of chicken-TLR's. This may in certain conditions generate a certain background activity.

Therefore, non-poultry cell lines such as mammalian cell lines are more preferred cell lines. An example of such a mammalian cell line is a HEK293 cell into which the TLR21 has been cloned. Such a cell line is more specifically selective for TLR21-activating signals.

Therefore, more preferably, a cell line for use in the detection system is the mammalian cell line HEK293 comprising a stably maintained reporter gene and into which HEK293 cell the TLR21 has been cloned.

Still another embodiment of the present invention relates to a method for the detection of immunostimulatory oligodeoxynucleotides according to the invention wherein that method comprises the steps of a) contacting an oligodeoxynucleotide with a cell according to the invention, b) detecting the level of product of the reporter gene.

In a preferred form of this method, the product of the reporter gene is SEAP

A more preferred form of this embodiment relates to a method for the detection of immunostimulatory oligodeoxynucleotides according to the invention, wherein the cell is a cell of chicken cell line HD11, or a HEK293 cell line into which chicken TLR21 has been cloned.

EXAMPLES

Example 1

Gene Cloning and Heterologous Expression of Chicken TLR21

Recent progress in chicken TLR research suggests that TLR21 is the functional homolog of mammalian TLR9 in avian species (Keestra 2008, Brownlie et al. 2009).

Outline of TLR21 Gene Cloning

Based on the Genbank database sequence NM_001030558, a primer pair was synthesized for the polymerase chain reaction (PCR) amplification of the chicken TLR21 gene:

```
Ga-TLR21-for1
GAAGCTTACCATGATGGAGACAGCGGAGAAGGC (SEQ ID NO: 1)

Ga-TLR21-rev1
GGCGGCCGCTACATCTGTTTGTCTCCTTCCCTG (SEQ ID NO: 2)
```

The primers were designed to provide flanking restriction cloning sites (underlined) and a Kozak sequence (italic) to the start and stop codons (bold). RT-PCR was performed using these primers and chicken spleen total RNA as a template. A PCR product of the expected size (~3000 bp) was cloned into pCR2.1-Topo and 5 independent plasmid clones (P1, P2, P12, P13, P14) were sequenced.

```
DNA sequence of chicken TLR21, as used.
AAGCTTACCATGATGGAGACAGCGGAGAAGGCATGGCCCAGCACCAGGATGTGCCCCTCCCACTGCTGTCCACTCTGGC

TGCTGCTGCTGGTGACAGTGACACTGATGCCGATGGTGCACCCGTATGGCTTTCGCAACTGCATTGAGGATGTCAAGGC

ACCTTTGTACTTCCGCTGCATCCAGCGCTTCCTGCAGTCGCCGGCCCTGGCAGTGTCTGACCTGCCACCACATGCCATC

GCGCTCAATCTGTCATACAACAAAATGCGCTGCCTGCAGCCCTCTGCCTTTGCCCACCTGACACAGCTGCATACCCTGG

ACCTGACCTACAACCTCCTGGAGACCCTCTCCCCTGGTGCCTTCAATGGGCTGGGTGTGCTGGTGGTGCTGGACCTGTC

TCACAACAAGCTGACCACACTTGCTGAAGGGGTGTTCAACAGCTTGGGCAACCTGTCCTCGCTGCAGGTACAACATAAC

CCCCTCAGCACGGTGTCACCAAGTGCTCTGCTACCCCTGGTCAACCTGCGCCGCCTGTCTCTACGGGCGGGCGGCTGA

ATGGGTTGGGGGCAGTGGCAGTGGCAGTGCAGGGCTTGGCACAGCTGGAGCTGTTGGACCTATGTGAAAACAACCTGAC

AACGCTGGGGCCAGGCCCACCGCTACCCGCCTCGCTGCTCACCCTGCAGCTGTGCAACAACTCGCTGAGGGAGTTAGCG

GGGGGCAGCCCGGAGATGCTATGGCACGTGAAGATACTCGACCTCTCCTACAACAGTATCTCACAGGCGGAGGTCTTCA

CCCAGCTCCACCTGCGCAACATCAGCCTGCTCCACCTGATCGGCAACCCCTTGGATGTCTTCCACCTGTTGGACATCTC

TGACATCCAACCTCGCAGCCTGGATTTCTCTGGGTTGGTGCTGGGGGCTCAGGGGCTGGATAAGGTGTGCCTGAGGCTG

CAGGGTCCCCAGGCCTTGCGGCGGCTGCAGCTACAACGCAACGGGCTGAAGGTGCTGCATTGTAATGCACTGCAGTTGT

GTCCTGTGCTGAGAGAGCTGGACCTGTCCTGGAACCGGCTACAGCACGTGGGCTGTGCCGGCCGGCTGCTGGGCAAGAA

GCAGCGGGAGAAGCTGGAAGTGCTGACAGTGGAACACAACCTGCTGAAGAAACTGCCGTCTTGCCTGGGGGCCCAGGTG

CTGCCTCGGCTGTACAACATTTCCTTCCGCTTTAACCGCATCCTGACTGTTGGGCCCCAAGCCTTTGCCTACGCCCGG

CCCTGCAGGTGTTGTGGCTCAATATTAACAGCCTGGTGTGGCTGGACAGGCAGGCACTGTGGAGGCTGCACAACCTGAC

AGAGCTGCGCCTGGACAACAACCTGCTGACCGACCTCTATCACAACTCCTTCATTGACCTCCACAGACTGCGCACCCTC
```

```
-continued
AACCTGCGCAACAACCGTGTCTCCGTCCTCTTCTCTGGTGTCTTCCAGGGGCTGGCTGAGCTGCAGACGCTGGATTTAG

GGGGCAACAACTTGCGCCACCTGACTGCACAGTCACTGCAGGGGCTGCCCAAACTGCGCAGGCTGTACCTGGACCGCAA

CAGATTGCTGGAGGTGAGCAGCACTGTGTTCGCCCCAGTGCAGGCTACCCTGGGGGTGCTGGACCTGCGGGCCAACAAC

CTGCAGTACATCTCACAGTGGCTGCGCAAGCCGCCACCCTTCCGCAACCTGAGCAGCCTGTACGACCTGAAGCTGCAGG

CGCAGCAGCCCTATGGACTGAAGATGCTGCCTCACTACTTCTTCCAGGGCTTGGTGAGGCTGCAGCAGCTGTCGCTGTC

ACAGAACATGCTGCGGTCCATCCCACCGGATGTCTTCGAGGACTTGGGCCAGCTGCGCTCCCTGGCATTGGCTGACAGC

AGCAATGGGCTGCATGACCTGCCTGACGGCATCTTCAGAAACCTGGGCAACCTGCGGTTCCTGGACCTGGAGAATGCAG

GGCTGCACTCGCTCACTCTGGAAGTCTTCGGCAATCTCAGCCGGCTGCAGGTGCTGCACTTGGCCAGAAACGAGCTGAA

GACCTTCAATGACAGCGTTGCCAGCCGGCTGTCCTCCTTGCGCTACCTGGACCTGCGCAAGTGTCCGCTCAGCTGCACC

TGTGACAACATGTGGCTGCAGGGCTGGCTGAACAACAGCCGTGTGCAGGTTGTCTACCCCTACAACTACACCTGTGGCT

CACAGCACAATGCCTACATCCACAGCTTTGACACACACGTCTGCTTCCTGGACCTGGGGCTCTATCTCTTTGCTGGGAC

TGCACCGGCAGTGCTGCTGCTGCTGGTGGTGCCGGTGGTGTACCACCGCGCCTACTGGAGGCTGAAGTACCACTGGTAC

CTTCTGCGGTGCTGGGTCAACCAGCGGTGGCGGCGGGAGGAAAAGTGCTACCTCTATGACAGCTTTGTGTCCTACAATT

CAGCTGATGAAAGTTGGGTGTTGCAGAAGCTGGTGCCTGAGCTGGAGCACGGTGCCTTCCGCCTCTGCTTGCACCACCG

CGACTTCCAGCCGGGCCGCAGCATCATTGACAACATTGTGGATGCTGTCTACAACAGCCGGAAGACGGTGTGCGTGGTG

AGCCGCAGCTACCTGCGCAGCGAGTGGTGCTCTCTAGAGGTGCAGTTGGCCAGCTACCGGCTGTTGGATGAGCGGCGTG

ACATCCTGGTACTGGTGCTGCTGGAGGACGTGGGTGATGCTGAGCTGTCTGCCTACCACCGCATGCGGCGGGTGCTGCT

GCGGCGCACCTACCTGCGCTGGCCTCTTGACCCCGCAGCTCAGCCGCTCTTTTGGGCACGGCTGAAGAGGGCACTGAGG

TGGGGAGAGGGAGGAGAGGAGGAGGAAGAAGAAGGTTTGGGTGGAGGGACGGGAAGGCCCAGGGAAGGAGACAAACAGA

TGTAGCGGCCGC (SEQ ID NO: 3)
```

Transfection of HEK293-pNifTy2-Zeo (Clonal Cell Line) with pcDNA3.1(+)-Neo-chiTLR21

Human embryonic kidney (HEK) cells 293 have been generated in the 1970s by viral transformation (Graham et al., 1977), and are now available to the research community via cell line repositories, such as ATCC.

pNifty2 is a plasmid that allows the detection of NFκB transcription factor activation, which is a hallmark of many immunostimulatory actions, toll-like receptor activations amongst them. The reporter gene in pNifTy2 dependent in its transcription/translation on NFκB activation is secreted alkaline phosphatase (SEAP). Details are described in the datasheet of the company selling this plasmid: Invivogen. Transformation/transfection events by pNifty2 are selected in both bacteria and mammalian cells by zeocin addition to the growth media.

HEK293 cells were transfected with pNifTy2 by standard methods (lipofection), a stable cell line was selected, the functionality of the NF-kB/SEAP axis established by stimulation with human tumor necrosis factor α (Sigma). Secreted SEAP in the culture supernatant of stimulated cells was determined by a microtiter plate colorimetric assay employing the chromogenic substrate p-nitrophenylphosphate (pNPP, 5 mM) in an alkaline buffer (50 mM NaHCO$_3$, pH9.6, 2 mM MgCl$_2$). Colour development ($\lambda$=405 nm) was monitored by a microtiter plate reader. This readout was also used for selecting clonal lines (by the limiting dilution method) with high signal to noise ratios. One of these selected clones (dubbed clone 11) was then used for further studies with chicken TLR21.

pcDNA3.1(+)-neo is a standard mammalian expression vector purchased from Invitrogen. Subcloning of the chicken TLR21 gene into this vector was done via flanking Hind III (start codon) and Not I (stop codon) sites that were introduced by PCR. (See FIG. 1).

This plasmid was then transfected (lipofection) into the clonal HEK293-pNifty2-zeo line, and recombinant cells were selected by addition of both zeocin and G418 into the growth medium. Functionality of the resulting polyclonal recombinant cell line was assessed by stimulation of the culture with ODN-X4 and ODN-HEK1-PTO and detection of SEAP. Superior clonal lines were then identified by the limiting dilution method followed by stimulation and SEAP detection.

SEAP is a reporter enzyme in mammalian systems (Yang et al., 1997). SEAP is a secreted form of human embryonic alkaline phosphatase. Its main advantages are the high stability and the extremely high specific activity, which ensure sensitivity and robustness of detection. Several substrates have been described for SEAP detection, but the economical and robust pNPP was selected, as its reaction product p-nitrophenolate is detected with high sensitivity ($\epsilon_{405}$=18500 M$^{-1}$ cm$^{-1}$). In our test setups, we perform kinetic assays, because they provide a wider dynamic range of quantification.

HEK293-pNifTy2-Zeo cells were transfected with pcDNA3.1(+)-Neo-chiTLR21 (linearized with Pvu I) and a polyclonal cell line was selected by supplementing the media with 350 μg/ml zeocin and 600 μg/ml G418. A functionality test was performed by stimulating the cells with ODN-X4 (PDE) and with ODN-HEK1 (PTO). Secreted alkaline phosphatase (SEAP) was produced by the selected cells, but not by the parental HEK293-pNifTy2-Zeo cell line. Single cell cloning was performed and individual clones were analyzed for their responsiveness to ODN-X4 (PDE) (GGGGGGT- TCGTTTTCGTTTTCGTTGGGGG) (SEQ ID NO: 27) and
ODN-HEK1 (PTO) (TCGTCGTTTTGTCGTTTGTCGTT)
(SEQ ID NO: 138)

Out of 46 zeo/G418-double-resistant clonal cell lines, only 3 were clearly responsive to the ODN stimuli, while 3-4 further cell lines showed weaker signals. 85% of the selected clones were, therefore, not functional.

For all further studies, clonal cell line 38, which produced by far the highest SEAP readout signal on response to ODN-X4 (PDE) and ODN-HEK1 (PTO) stimulation, was used.

FIGS. 2-5 give an overview of the SEAP activity of the various zeo/G418-double-resistant clonal cell lines.

Example 2

Analysis of Influence of the Nature of $N_3$-$N_6$ on Activity

The following PDE CpG-ODNs were tested:

```
ODN-X1 = (SEQ ID NO: 4),
ODN-X2 = (SEQ ID NO: 5),
ODN-X3 = (SEQ ID NO: 6),
ODN-X4 = (SEQ ID NO: 7),
ODN-X5 = (SEQ ID NO: 8),
ODN-X6 = (SEQ ID NO: 9),
ODN-X7 = (SEQ ID NO: 10).
```

Furthermore, as a control the PDE version of ODN-2006 (CpG7909), whose PTO counterpart is a drug/vaccine candidate in human tumor treatment, was used as a positive control, while its GpC counterpart was used as negative control (ODN2006-control).

Figure 6:
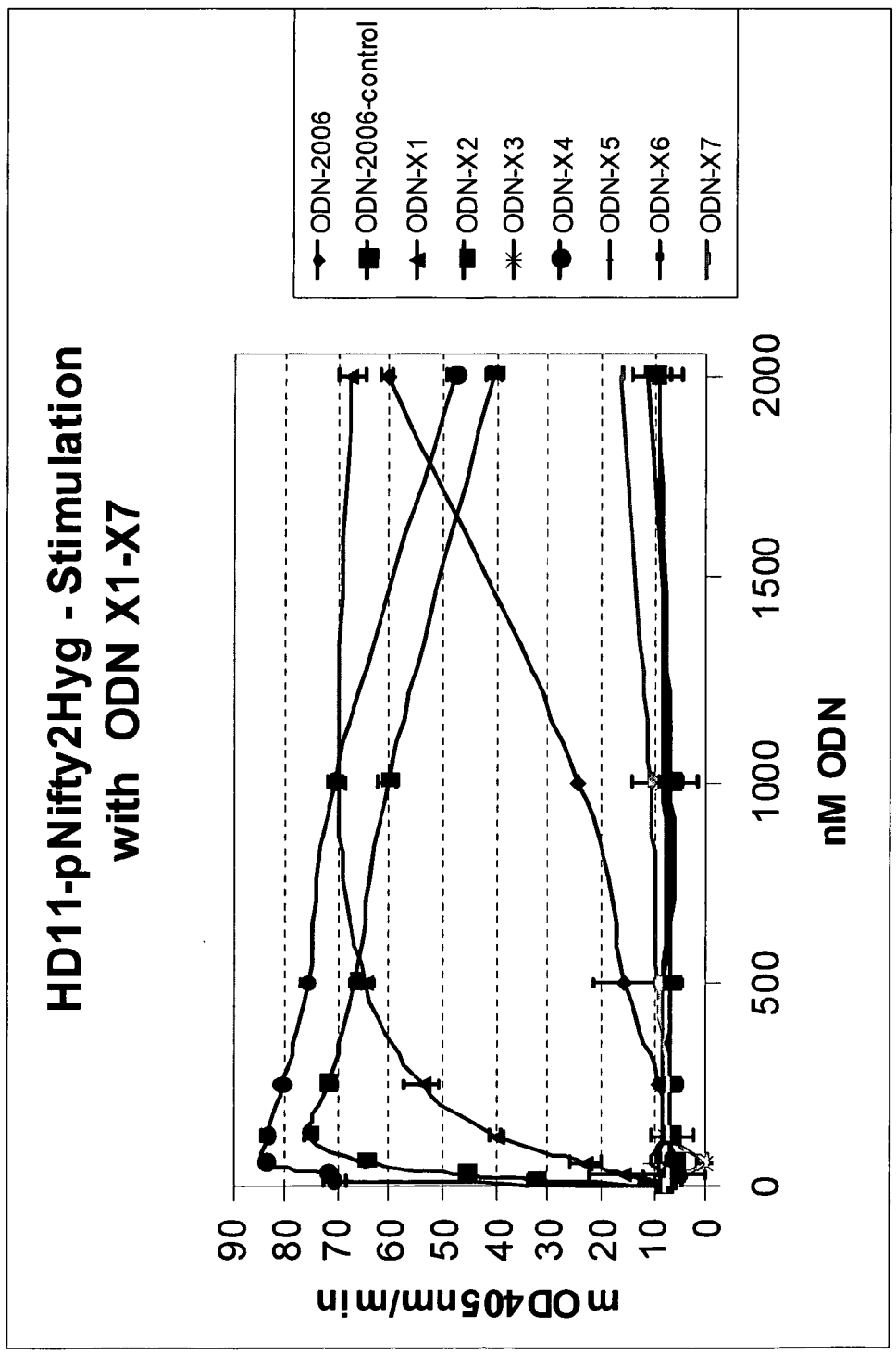

With the HD11-pNifTyhyg clonal cell line, the results obtained in titration experiments starting at 2000 nM are shown in FIG. 6.
The ranking of activity based on this test:
ODN-X4>ODN-X2>ODN-X1>>ODN-2006 (PDE)
Less active:
ODN-X3, ODN-X5, ODN-X6, ODN-X7, ODN-2006-control (PDE)

Figure 7:
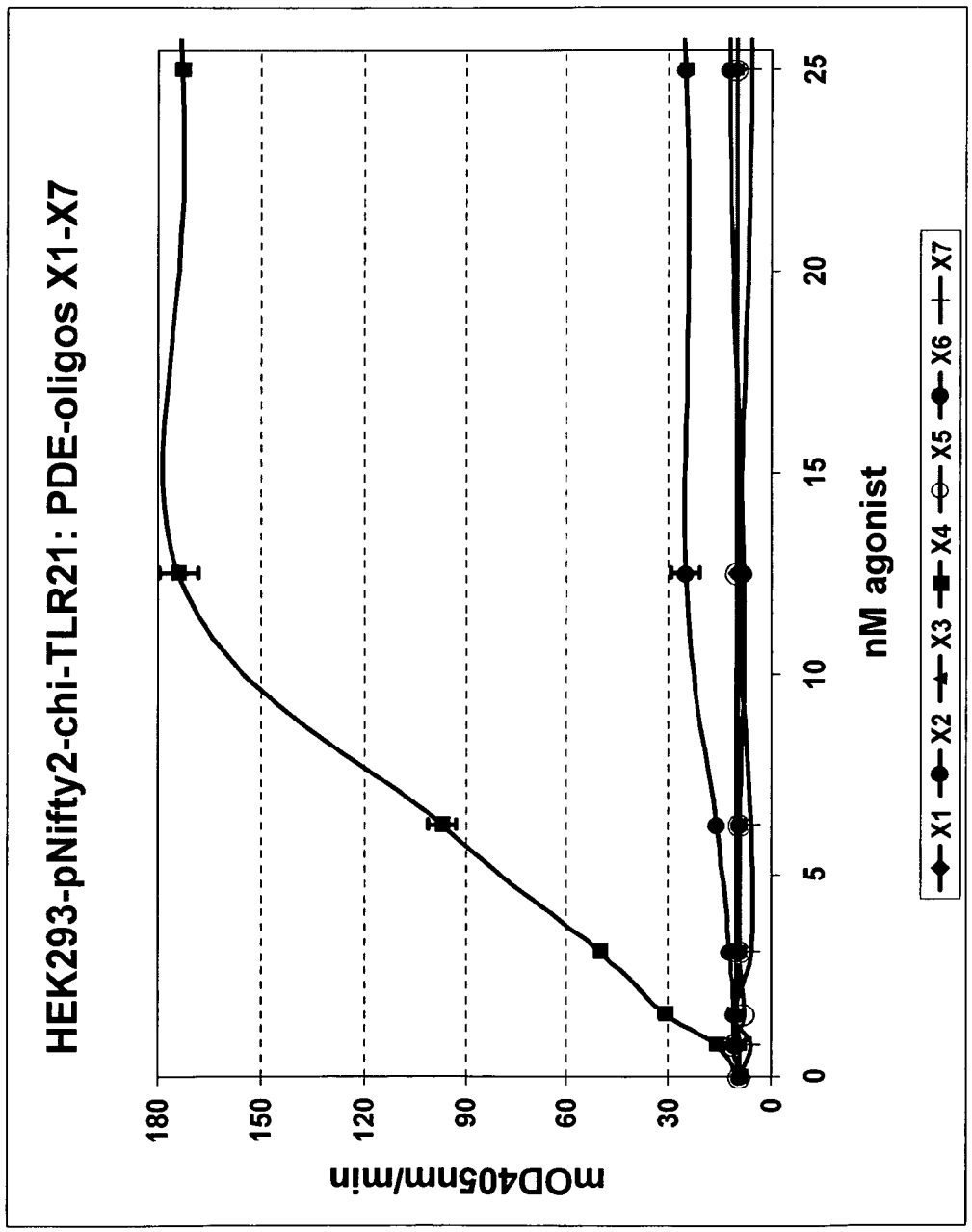

With the HEK293-pNifTy2-pcDNA3.1-chiTLR21 clonal cell line, the results obtained in titration experiments starting at 100 nM are shown in FIG. 7.
The ranking of activity based on this test:
ODN-X4>>ODN-X2
Less active:
ODN-X1, ODN-X3, ODN-X5, ODN-X6, ODN-X7

Taken together, from these tests, PDE CpG ODN-X4, and not the typical mouse (ODN-X1) and human (ODN-X2) proved to be the most efficient reagent in both chicken cell line HD11 and in a heterologous chicken TLR21 test system.

Example 3

The Role of the Nucleotides Immediately Adjacent to the CpG Motif

In order to identify the activity of variant hexanucleotide sequence motifs for chicken HD11 cells and heterologously expressed chicken TLR21, derivatives were made where the directly neighboring positions of the CpG element were permutated:

Based on the [TNCGNT]$_3$ Motif

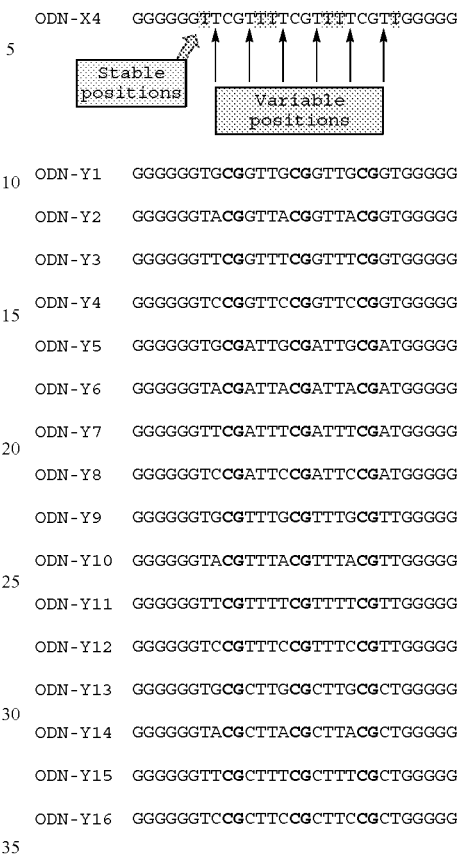

```
ODN-Y1    GGGGGGTGCGGTTGCGGTTGCGGTGGGGG
ODN-Y2    GGGGGGTACGGTTACGGTTACGGTGGGGG
ODN-Y3    GGGGGGTTCGGTTTCGGTTTCGGTGGGGG
ODN-Y4    GGGGGGTCCGGTTCCGGTTCCGGTGGGGG
ODN-Y5    GGGGGGTGCGATTGCGATTGCGATGGGGG
ODN-Y6    GGGGGGTACGATTACGATTACGATGGGGG
ODN-Y7    GGGGGGTTCGATTTCGATTTCGATGGGGG
ODN-Y8    GGGGGGTCCGATTCCGATTCCGATGGGGG
ODN-Y9    GGGGGGTGCGTTTGCGTTTGCGTTGGGGG
ODN-Y10   GGGGGGTACGTTTACGTTTACGTTGGGGG
ODN-Y11   GGGGGGTTCGTTTTCGTTTTCGTTGGGGG
ODN-Y12   GGGGGGTCCGTTTCCGTTTCCGTTGGGGG
ODN-Y13   GGGGGGTGCGCTTGCGCTTGCGCTGGGGG
ODN-Y14   GGGGGGTACGCTTACGCTTACGCTGGGGG
ODN-Y15   GGGGGGTTCGCTTTCGCTTTCGCTGGGGG
ODN-Y16   GGGGGGTCCGCTTCCGCTTCCGCTGGGGG
```

ODN-Y1=(SEQ ID NO: 11), ODN-Y2=(SEQ ID NO: 12), ODN-Y3=(SEQ ID NO: 13), ODN-Y4=(SEQ ID NO: 14), ODN-Y5=(SEQ ID NO: 15), ODN-Y6=(SEQ ID NO: 16), ODN-Y7=(SEQ ID NO: 17), ODN-Y8=(SEQ ID NO: 18), ODN-Y9=(SEQ ID NO: 19), ODN-Y10=(SEQ ID NO: 20), ODN-Y11=(SEQ ID NO: 21), ODN-Y12=(SEQ ID NO: 21, ODN-Y13=(SEQ ID NO: 23), ODN-Y14=(SEQ ID NO: 24), ODN-Y15=(SEQ ID NO: 25), ODN-Y16=(SEQ ID NO: 26),

It should be pointed out here, that the permutation of the sequences leads in one case back to the ODN-X4 motif (→ODN-Y11)

Figure 8:
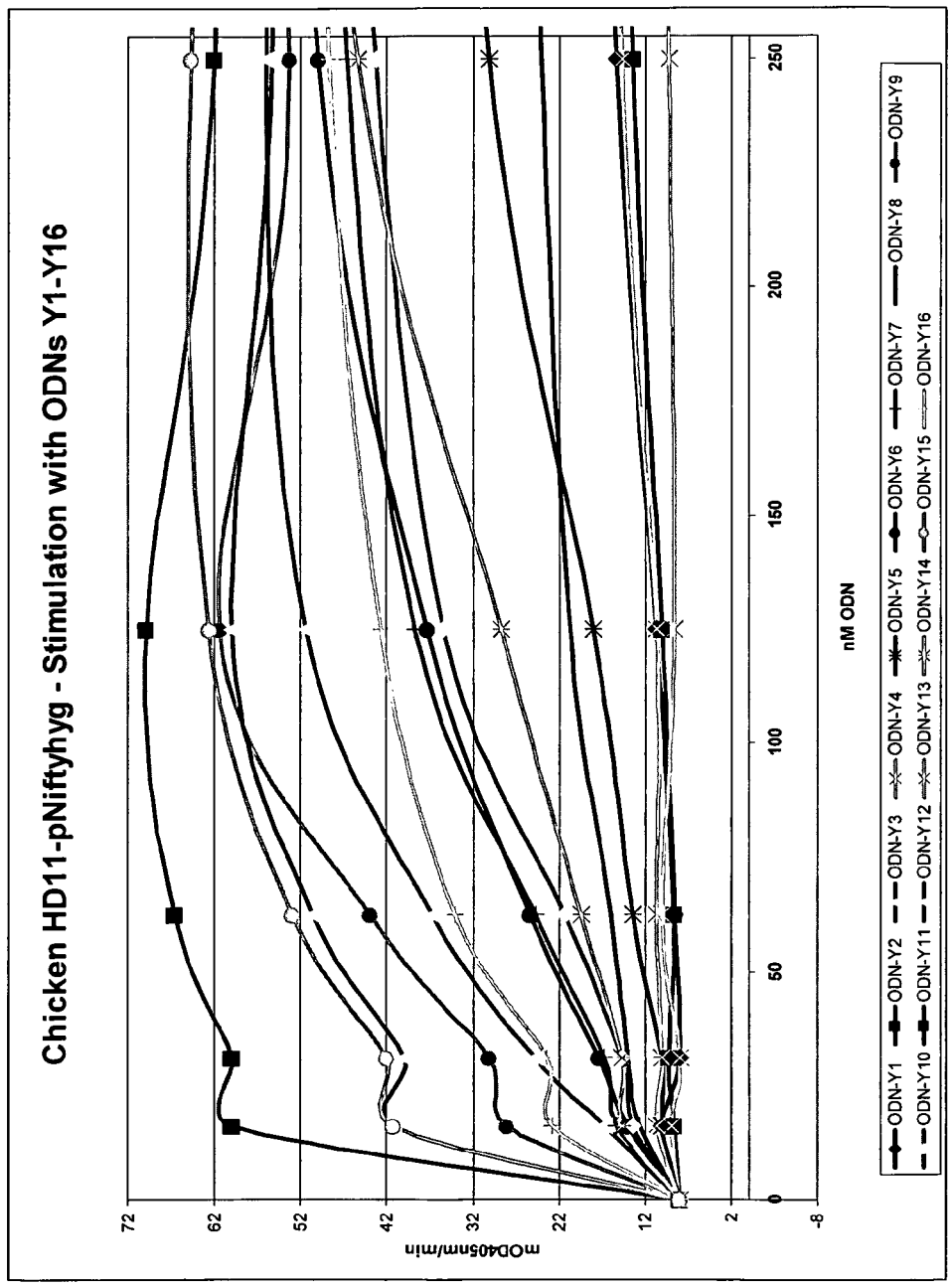

With the HD11-pNifTyhyg clonal cell line, the results obtained in titration experiments starting at 2000 nM are shown in FIG. 8.
The ranking of activity based on this test in HD11-pNiftyhyg:
ODN-Y11 (=ODN-X4)>ODN-Y15>ODN-Y12>ODN-Y9>ODN-Y3>ODN-Y16>ODN-Y7~ODN-Y6~ODN-Y10~ODN-Y14>ODN-Y8~ODN-Y5
Less active: ODN-Y1, ODN-Y2, ODN-Y4, ODN-Y13

Figure 9:
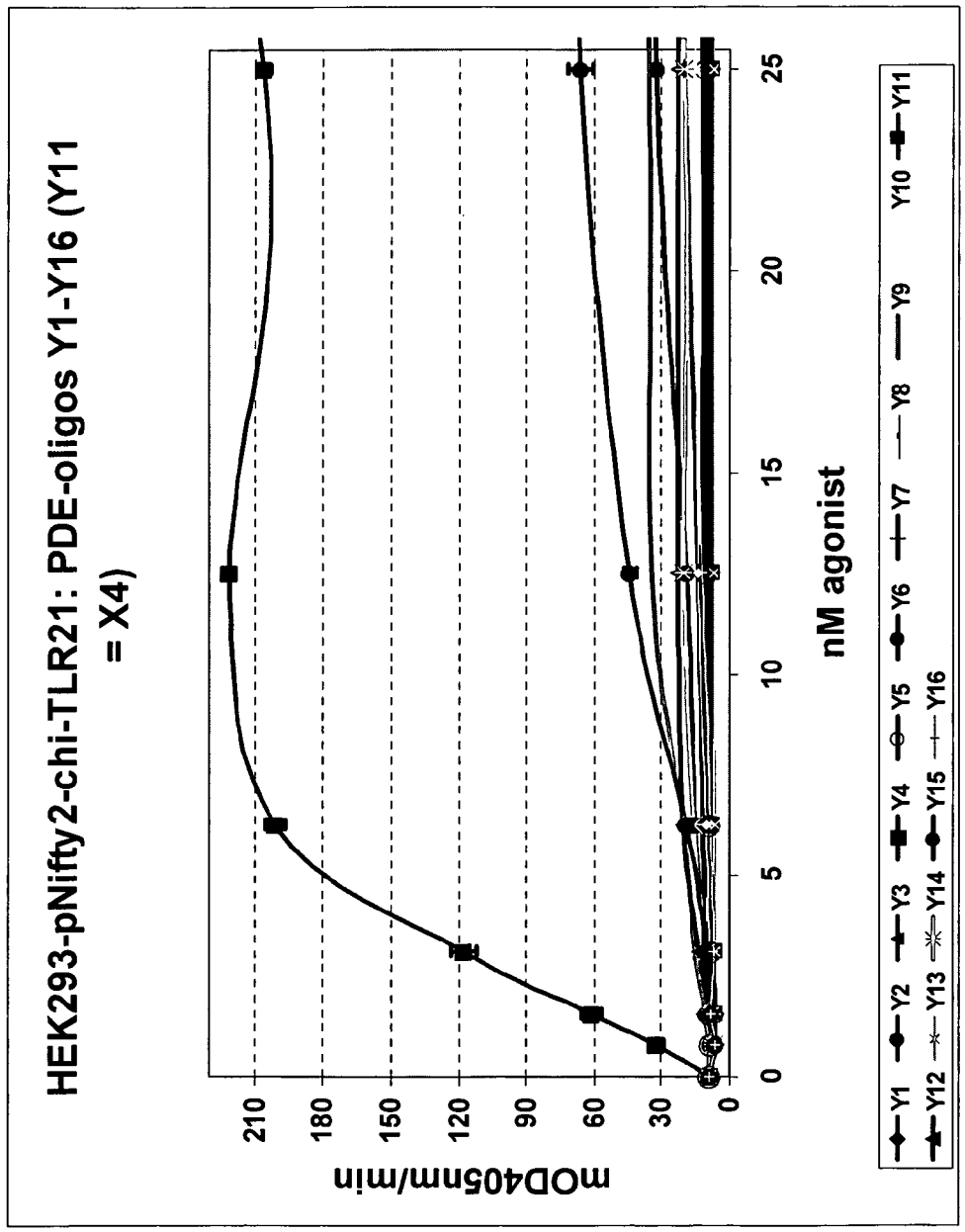

With the HEK293-pNifTy2-pcDNA3.1-chiTLR21 clonal cell line, the results obtained in titration experiments starting at 100 nM are shown in FIG. 9
The ranking of activity based on this test: in HEK293-pNifty2-pcDNA3.1-chiTLR21: ODN-Y11 (=ODN-X4)>>ODN-Y15>ODN-Y9>ODN-Y12>ODN-Y14~ODN-Y6>ODN-Y7~ODN-Y8~ODN-Y10~ODN-Y16>ODN-Y3~ODN-Y5
Less active: ODN-Y1, ODN-Y2, ODN-Y4, ODN-Y13

Taken together, from both test systems similar conclusions can be drawn:

ODN-Y11, which is identical to ODN-X4, is confirmed as the strongest stimulator of HD11 macrophages and of HEK293 cells that heterologously express chicken TLR21. It appears that the discriminatory power of the HEK293-pNifTy2-pcDNA3.1-chiTLR21 clonal cell line is higher than that of HD11-pNiftyhyg.

Example 4

The Role of 3'-Neighboring Positions of the TpCpGpT Element in ODN-X4

In order to further identify preferred hexanucleotide sequence motifs for chicken HD11 cells and heterologously expressed chicken TLR21, the 3'-neighboring positions of the TpCpGpT element in ODN-X4 were permutated:
Based on the (TTCGTN)$_3$ Motif

```
ODN-X4  = (SEQ ID NO: 27),
ODN-X41 = (SEQ ID NO: 28),
ODN-X42 = (SEQ ID NO: 29),
ODN-X43 = (SEQ ID NO: 30),
```

Figure 10:
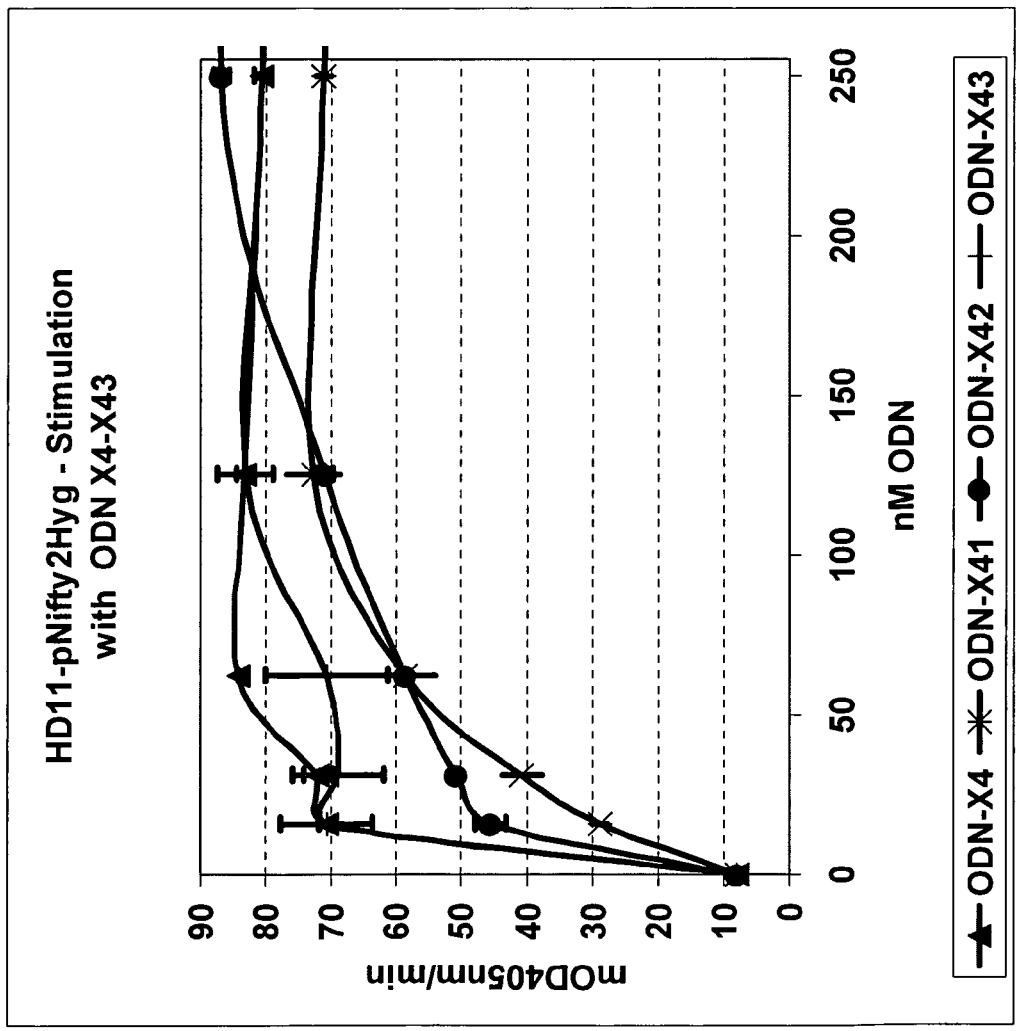
Figure 11:
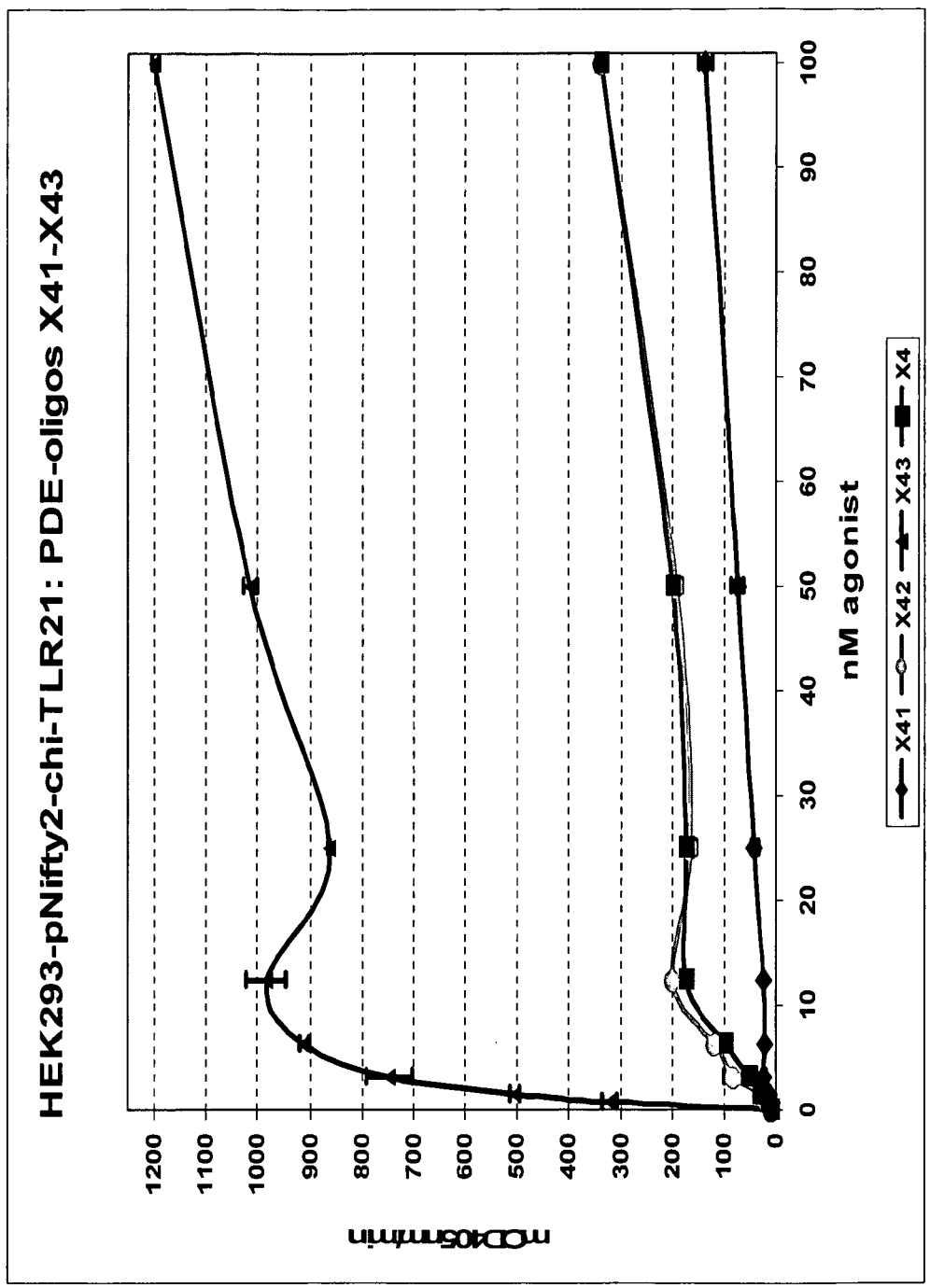

With the HD11-pNifTyhyg clonal cell line, the results obtained in titration experiments starting at 2000 nM are shown in FIG. 10.
The ranking of activity based on this test in HD11-pNiftyhyg: ODN-X4~ODN-X43>ODN-X42~ODN-X41
With the HEK293-pNifTy2-pcDNA3.1-chiTLR21 clonal cell line, the results obtained in titration experiments starting at 100 nM are shown in FIG. 11.
The ranking of activity based on this test in HEK293-pNifTy2-pcDNA3.1-chiTLR21: ODN-X43>>ODN-X4~ODN-X42>ODN-X41

Example 5

The Role of the 5'-Neighboring Positions of the TpCpGpT Element in ODN-X4

In order to still further identify further hexanucleotide sequence motifs for chicken HD11 cells, the 5'-neighboring positions of the TpCpGpT element in ODN-X4 were permutated:
Based on the (NTCGTT)$_3$ Motif

```
ODN-X2     GGGGGGGTCGTTGTCGTTGTCGTTGGGGG
ODN-X24    GGGGGGATCGTTATCGTTATCGTTGGGGG
ODN-X25    GGGGGGCTCGTTCTCGTTCTCGTTGGGGG
ODN-X26/4  GGGGGGTTCGTTTTCGTTTTCGTTGGGGG
```

Figure 12:
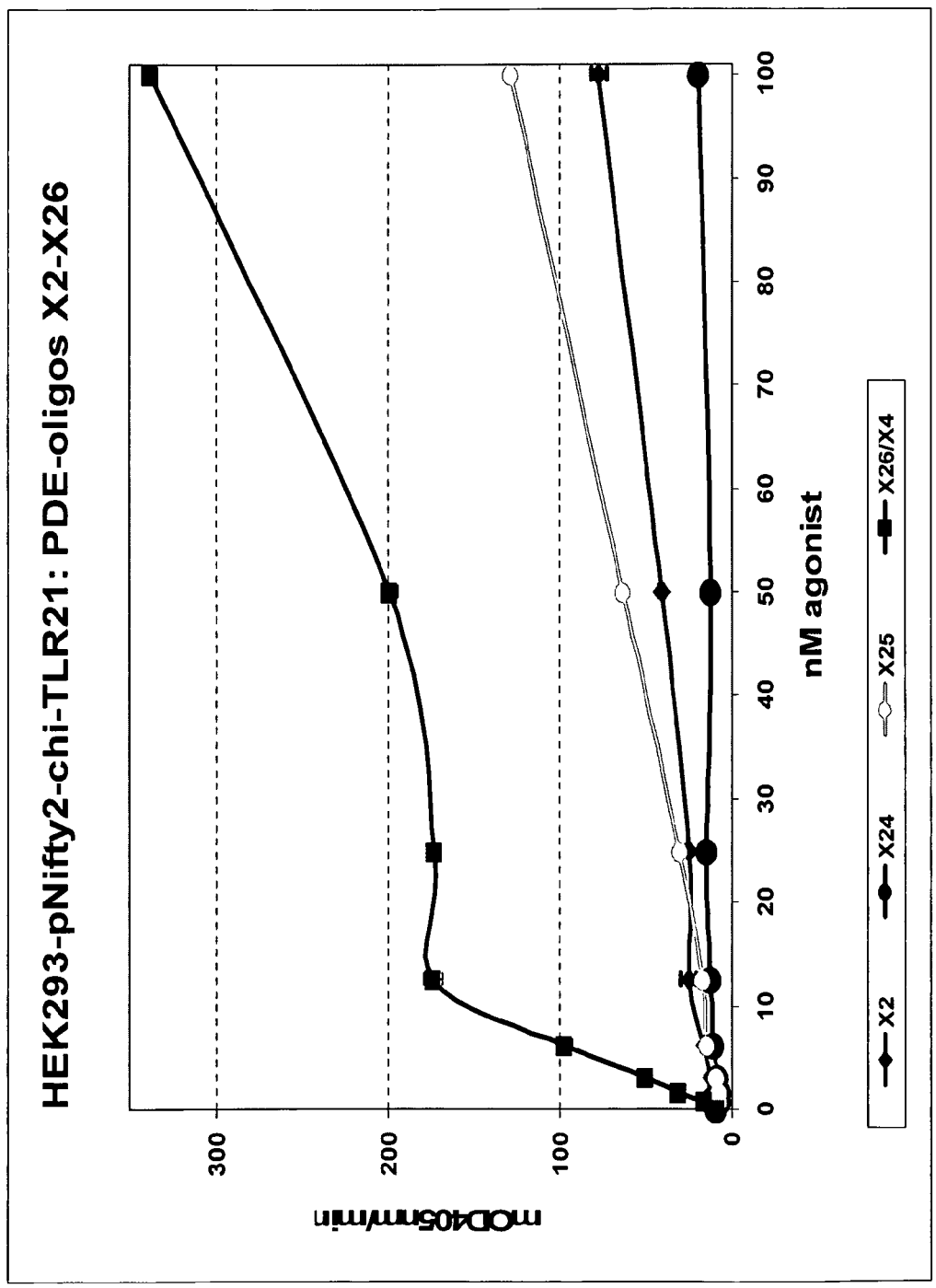

ODN-X2=(SEQ ID NO: 31), ODN-X24=(SEQ ID NO: 32), ODN-X25=(SEQ ID NO: 33), ODN-X26/4=(SEQ ID NO: 34),
With the HEK293-pNifTy2-pcDNA3.1-chiTLR21 clonal cell line, the results obtained in titration experiments starting at 100 nM are shown in FIG. 12.
The ranking of activity based on this test in HEK293-pNifTy2-pcDNA3.1-chiTLR21: ODN-X4>>ODN-X25>ODN-X2>ODN-X24

Example 6

The Effect of Shortening or Deletion of the 5'-dG$_6$

In order to further characterize the structure-activity relationship (SAR) for PDE-ODN X4 in chicken HD11 cells and heterologously expressed chicken TLR21, the effect of shortening or deletion of the 5'-dG$_6$ was investigated.

```
ODN-X4      = (SEQ ID NO: 35),
ODN-X4-5MIN1 = (SEQ ID NO: 36),
ODN-X4-5MIN2 = (SEQ ID NO: 37),
ODN-X4-5MIN3 = (SEQ ID NO: 38),
ODN-X4-5MIN4 = (SEQ ID NO: 39)
ODN-X4-5MIN5 = (SEQ ID NO: 40),
ODN-X4-5MIN6 = (SEQ ID NO: 41)
```

Figure 13:
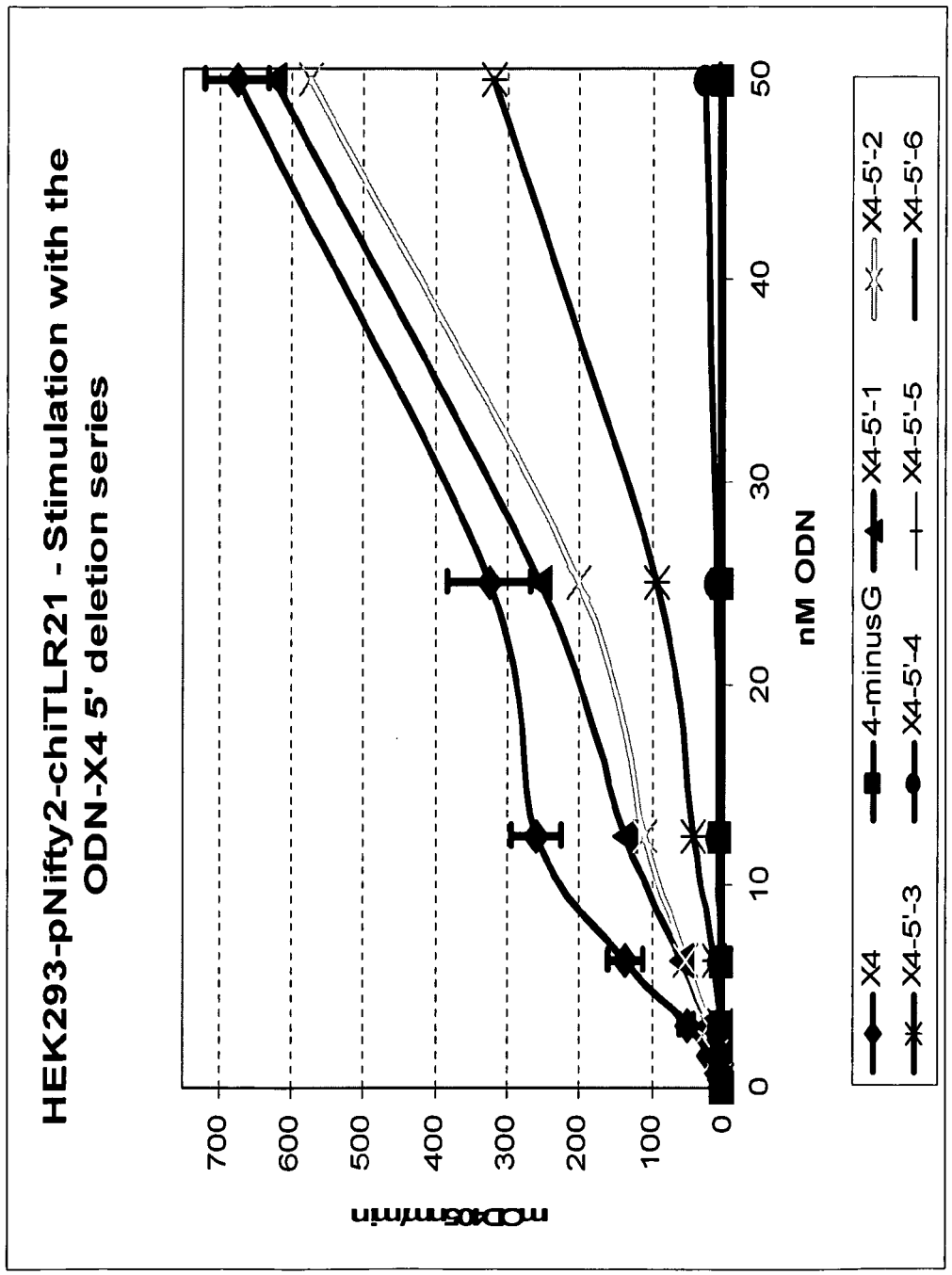

With the HEK293-pNifTy2-pcDNA3.1-chiTLR21 clonal cell line, results obtained in titration experiments starting at 100 nM are shown in FIG. 13.
The ranking of activity based on this test in HEK293-pNifTy2-pcDNA3.1-chiTLR21: ODN-X4>ODN-X4-5'-1>ODN-X4-5'-2>ODN-X4-5'-3>>ODN-X4-5'-4>ODN-X4-5'-6≈ODN-X4-5'-5
ODNs X4-5'-4-6 are less active in this concentration range.

Example 7

The Effect of Shortening or Deletion of the 3'-dG$_5$

In order to further characterize the structure-activity relationship (SAR) for PDE-ODN X4 in chicken HD11 cells and heterologously expressed chicken TLR21, the effect of shortening or deletion of the 3'-dG$_5$ was investigated.

```
ODN-X4-3MIN1 = (SEQ ID NO: 42),
ODN-X4-3MIN2 = (SEQ ID NO: 43),
ODN-X4-3MIN3 = (SEQ ID NO: 44),
ODN-X4-3MIN4 = (SEQ ID NO: 45),
ODN-X4-3MIN5 = (SEQ ID NO: 46)
```

Figure 14:
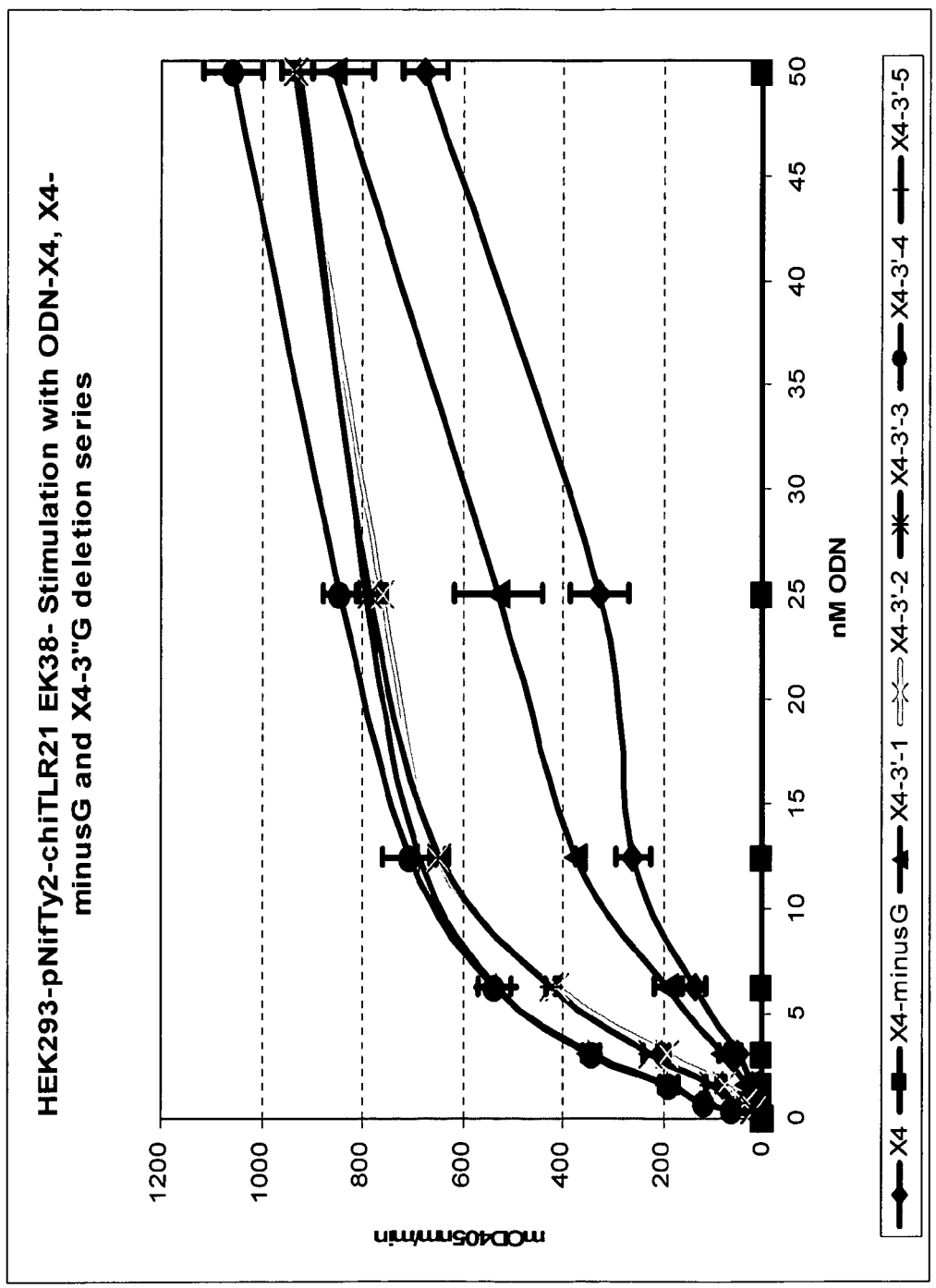

With the HEK293-pNifTy2-pcDNA3.1-chiTLR21 clonal cell line, the results obtained in titration experiments starting at 100 nM are shown in FIG. 14.
The ranking of activity based on this test in HEK293-pNifTy2-pcDNA3.1-chiTLR21: ODN-X4-5'-5≈ODN-X4-5'-4≈ODN-X4-5'-3≈ODN-X4-5'-2>ODN-X4-5'-1>ODN-X4 The ODN X4-minusG lacking both 3'dG$_6$ and 3'dG$_5$ is less active in this concentration range.
Furthermore, it was investigated whether additional Gs in the 5'-dG$_6$ and the 3'-dG$_5$ have an effect:

```
ODN-X4       GGGGGGTTCGTTTTCGTTTTCGTTGGGGG
ODN-X4-plus1 GGGGGGGTTCGTTTTCGTTTTCGTTGGGGGG
ODN-X4-plus2 GGGGGGGGTTCGTTTTCGTTTTCGTTGGGGGGG
```

Figure 15:
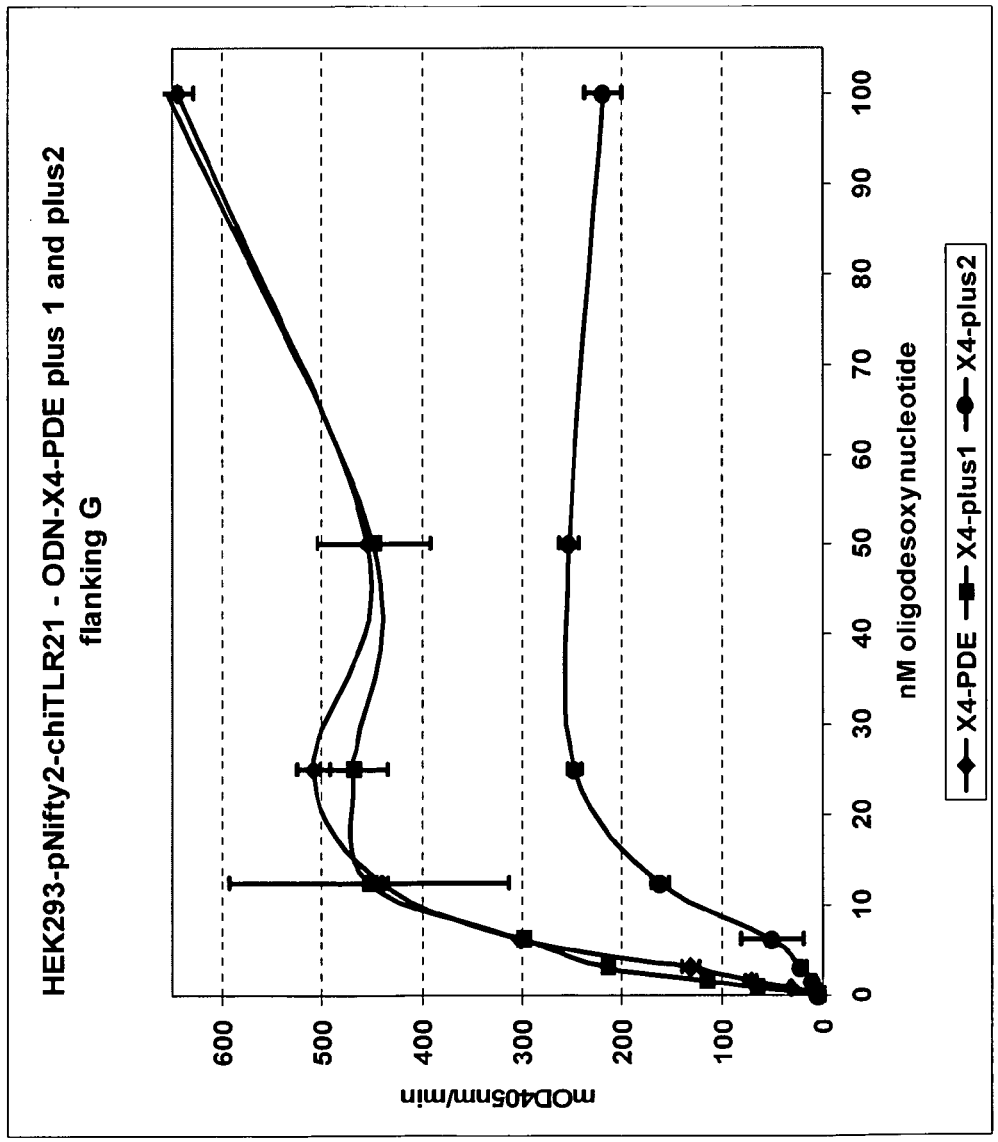

With the HEK293-pNifTy2-pcDNA3.1-chiTLR21 clonal cell line, the results obtained in titration experiments starting at 100 nM are shown in FIG. 15.

While the addition of one G on both sides of ODN-X4 does have neither a beneficial nor a deleterious effect on the stimulatory activity in HEK293-pNifTy2-pcDNA3.1-chiTLR21, the addition of two Gs seems to lead to a molecule with lower potency.

Example 8

The Replacement of Phosphodiester (PDE) Bonds by Phosphorothioate (PTO) Analogs

In order to improve the stability and immunostimulatory capacity of CpG-ODNs the replacement of phosphodiester (PDE) bonds by phosphorothioate (PTO) analogs was investigated. In order to further characterize this aspect of the structure-activity relationship (SAR) for PDE-ODN X4 in HD11-pNifTyhyg chicken macrophages and in heterologously expressed chicken TLR21, the effect of replacement of all PDE bonds by PTO (ODN-X4-PTO) and of the PDE bonds by PTO only in the 5'-dG$_6$ and 3'dG$_5$ runs (ODN-X4-PTO-Gonly) was investigated.

Figure 16:
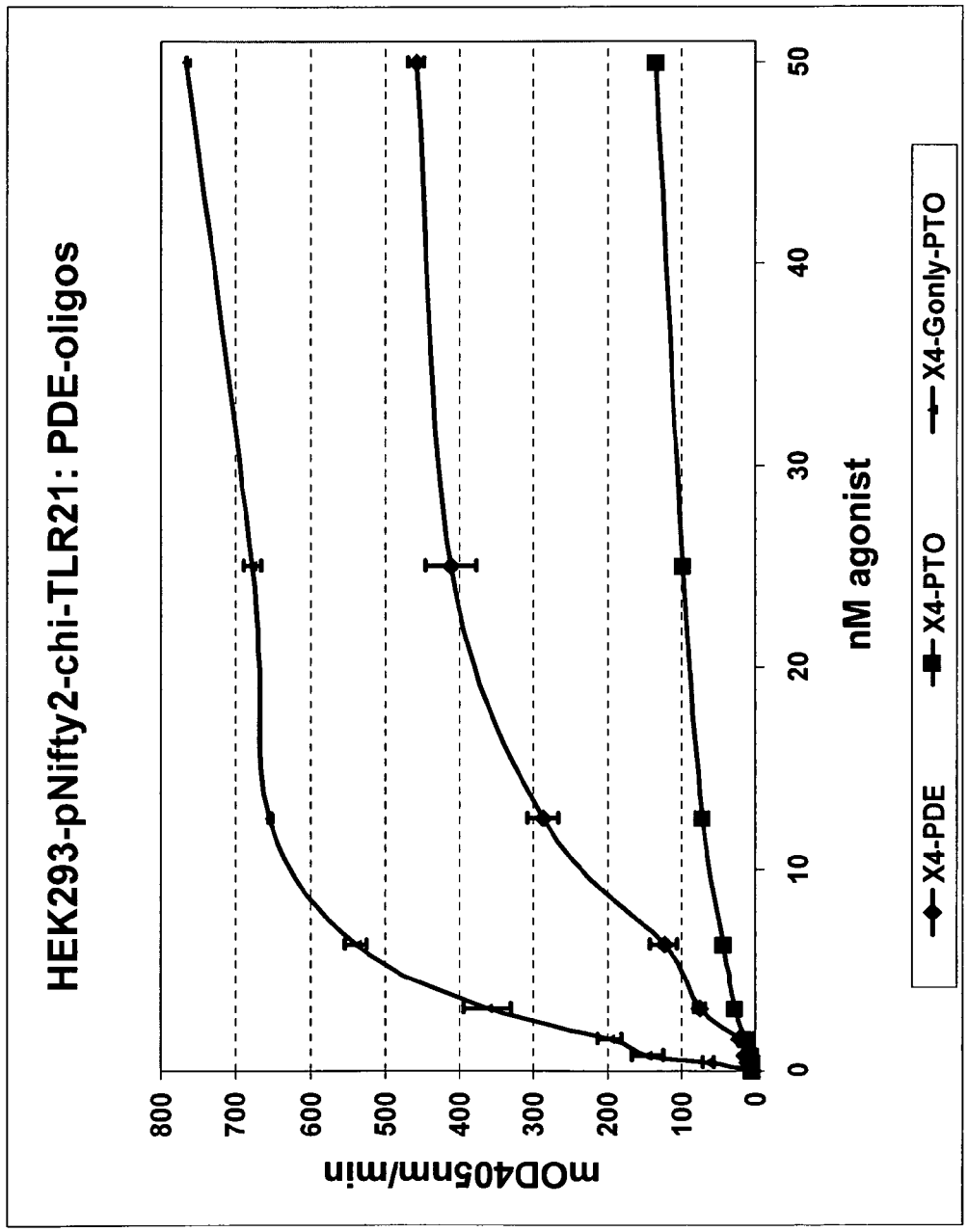

With the HEK293-pNifTy2-pcDNA3.1-chiTLR21 clonal cell line, the results obtained in titration experiments starting at 50 nM are shown in FIG. 16.

In this readout system, a lower potency of X4-PTO versus X4-PDE was found. The X4-PTO-Gonly proved to be of higher potency in HEK293-pNifTy2-pcDNA3.1-chiTLR21 than the parental X4-PDE.

In vitro potency ranking:
ODN-X4-PTO-G$_{only}$>ODN-X4 (PDE)>ODN-X4-PTO

Example 9

Investigation of the Species-Specificity of ODN-X4 (PDE)

In order to investigate the species-specificity of ODN-X4 (PDE), HEK293-XL-pUNO-humanTLR9 cells were purchased, subsequently transfected with pNifTy2, their responsiveness to literature PTO-CpGs was established, clonal functional cell lines were generated and one of them was used for comparative studies with HEK293-pNifTy2-pcDNA3.1-chiTLR21.

In these comparative studies, in addition to ODN-X4 (PDE), the well-established for human TLR9 high potency PTO-ODNs 2006 (=CpG7909) and 2007 and their GpC control counterparts were used.

Figure 17:
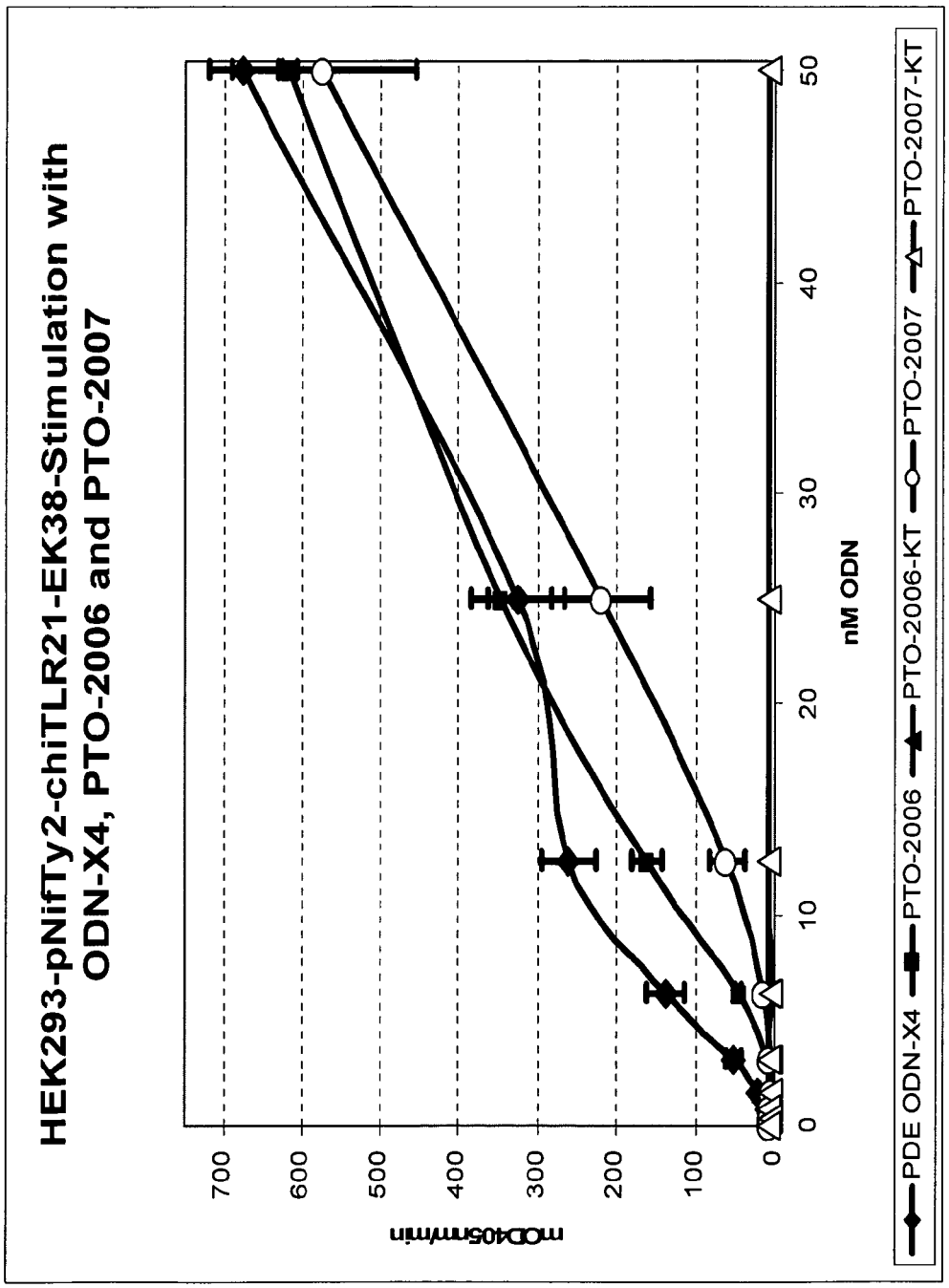

With the HEK293-pNifTy2-pcDNA3.1-chiTLR21 clonal cell line, the results obtained in titration experiments starting at 50 nM are shown in FIG. 17.

The following ranking order of activity was obtained:
ODN-X4 (PDE)~PTO-2006>PTO-2007.

The GpC control PTO-ODNs 2006 and 2007 were inactive in the concentration ranges considered here.

Figure 18:
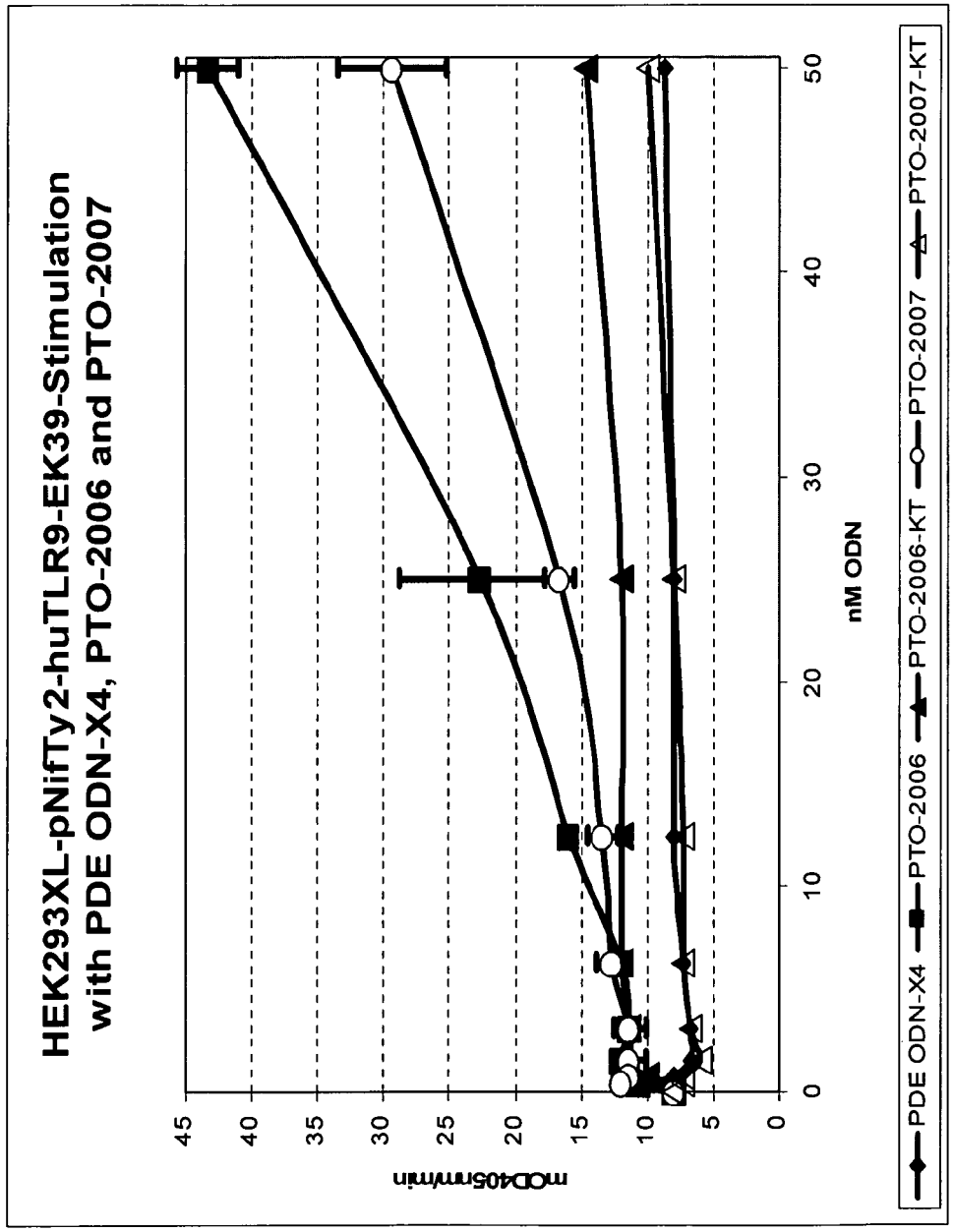

With the HEK293XL-pUNO-huTLR9-pNifTy2 clonal cell line, the results obtained in titration experiments starting at 50 nM are shown in FIG. 18.

The following ranking order of activity was obtained:
PTO-2006>PTO-2007.

The GpC control PTO-ODNs 2006 and 2007 and the ODN-X4 (PDE) were inactive in the concentration ranges considered.

This result established the chicken species specificity of ODN-X4 (PDE).

Example 10

Investigations on the Optimal Number of TTCGTT Repeats

In order to invest the optimal number of TTCGTT repeats the following constructs were made:

```
                                           (SEQ ID NO: 51)
1 X4-Sin   GGGGGGTTCGTTGGGGG (SEQ ID NO: 52)
2 X4-Doub  GGGGGGTTCGTTTTCGTTGGGGG (SEQ ID NO: 53)
3 X4-Trip  GGGGGGTTCGTTTTCGTTTTCGTTGGGGG (SEQ ID NO: 54)
4 X4-Quad  GGGGGGTTCGTTTTCGTTTTCGTTTTCGTTGGGGG (SEQ ID NO: 55)
5 X4-Pent  GGGGGGTTCGTTTTCGTTTTCGTTTTCGTTTTCGTTGGGGG (SEQ ID NO: 56)
6 X4-Hex   GGGGGGTTCGTTTTCGTTTTCGTTTTCGTTTTCGTTTTCGT
           TGGGGG
```

Figure 19:
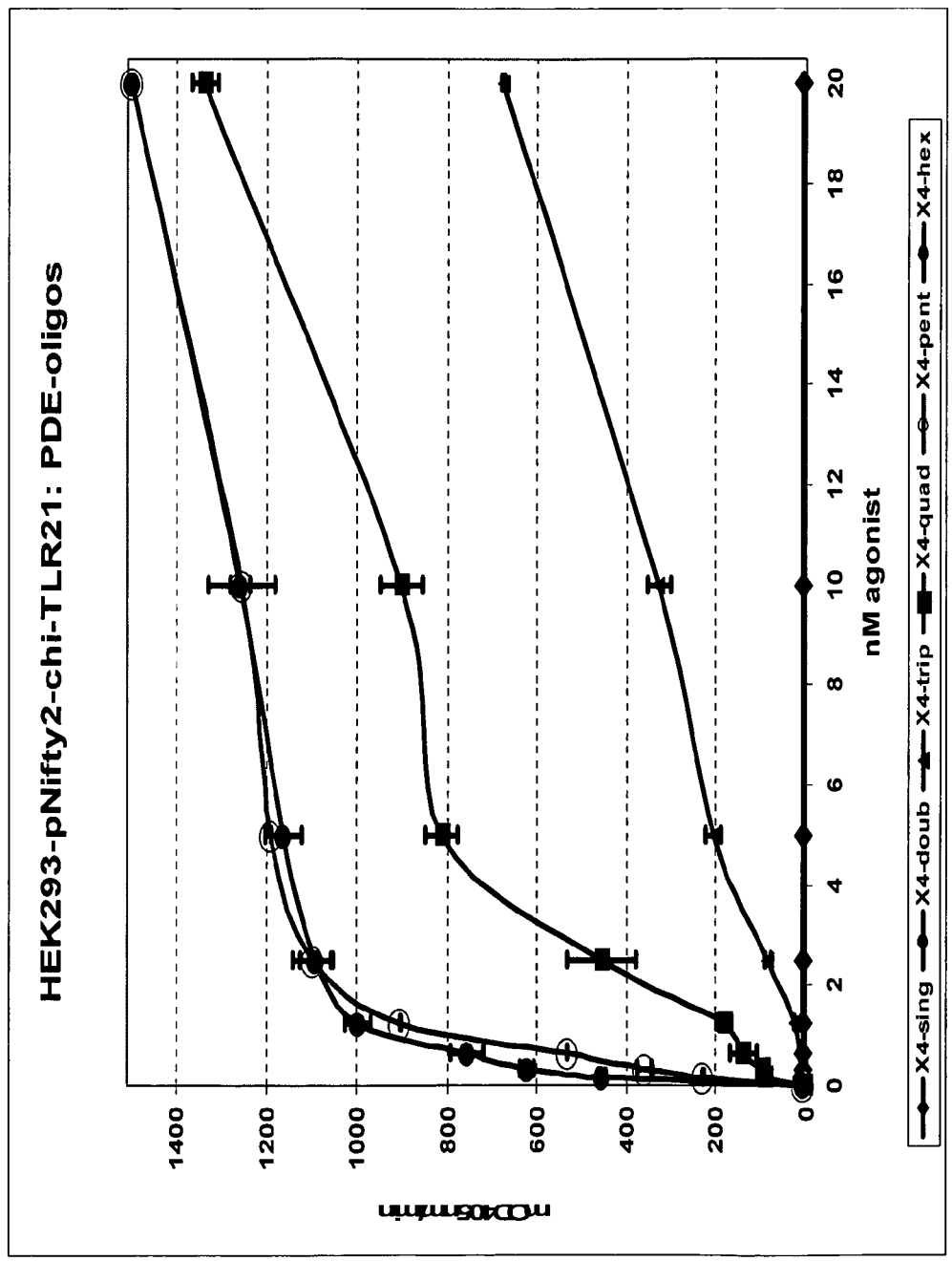

With the HEK293-pNifTy2-pcDNA3.1-chiTLR21 clonal cell line, the results obtained in titration experiments starting at 20 nM are shown in FIG. 19.

The following ranking of stimulatory potency was identified for HEK293-pNifTy2-pcDNA3.1-chiTLR21:

X4-hex~X4-pent>X4-quad>X4-trip (='classical' X4)

X4-doub and X4-sing were inactive at the test concentrations applied here.

Example 11

The Effect of the Number of Separating Ts

In order to invest the effect of the number of Ts separating the CpG motifs, the following constructs were made:

```
                                           (SEQ ID NO: 57)
1 X4-Li1   GGGGGGTTCGTCGTCGTTGGGGG (SEQ ID NO: 58)
2 X4-Li2   GGGGGGTTCGTTCGTTCGTTGGGGG (SEQ ID NO: 59)
3 X4-Li3   GGGGGGTTCGTTTCGTTTCGTTGGGGG (SEQ ID NO: 60)
4 X4-Li4   GGGGGGTTCGTTTTCGTTTTCGTTGGGGG (SEQ ID NO: 61)
5 X4-Li5   GGGGGGTTCGTTTTTCGTTTTTCGTTGGGGG (SEQ ID NO: 62)
6 X4-Li6   GGGGGGTTCGTTTTTTCGTTTTTTCGTTGGGGG
```

Figure 20:
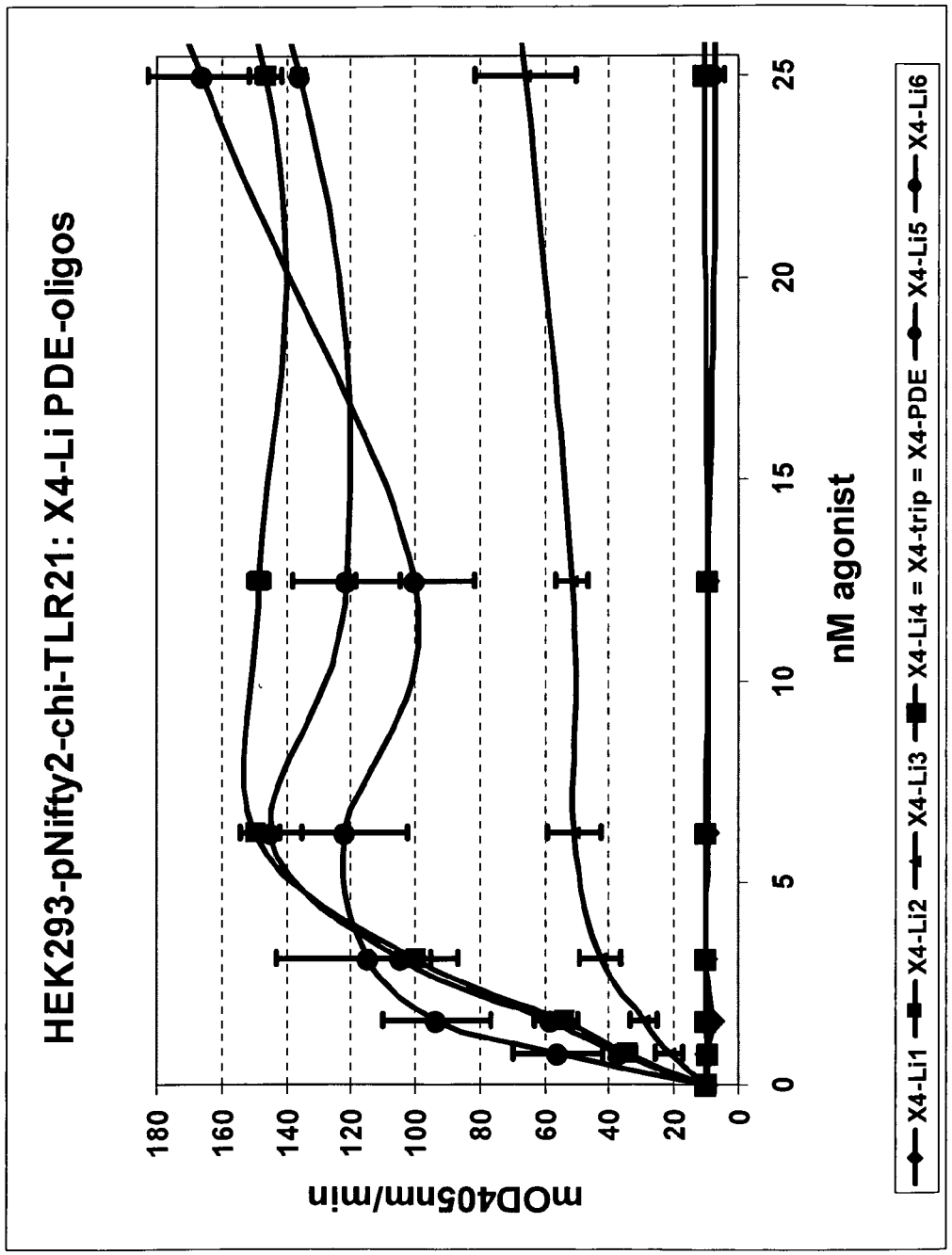

With the HEK293-pNifTy2-pcDNA3.1-chiTLR21 clonal cell line, the following results were obtained in titration experiments starting at 25 nM are shown in FIG. 20.

The following ranking of stimulatory potency was identified for HEK293-pNifTy2-pcDNA3.1-chiTLR21:
X4-Li6~X4-Li5~X4-Li4 (='classical' X4)>X4-Li3>X4-Li2~X4-Li1

Example 12

Investigations on the Optimal Number of T Residues at the Borders to the dG Runs In order to investigate the optimal number of T residues at the borders to the dG runs, the following constructs were made:

```
                                            (SEQ ID NO: 63)
X4-Bo1    GGGGGGTCGTTTTCGTTTTCGTGGGGG (SEQ ID NO: 64)
X4-Bo2    GGGGGGTTCGTTTTCGTTTTCGTTGGGGG (SEQ ID NO: 65)
X4-Bo3    GGGGGGTTTCGTTTTCGTTTTCGTTTGGGGG (SEQ ID NO: 66)
X4-Bo4    GGGGGGTTTTCGTTTTCGTTTTCGTTTTGGGGG
```

Figure 21:
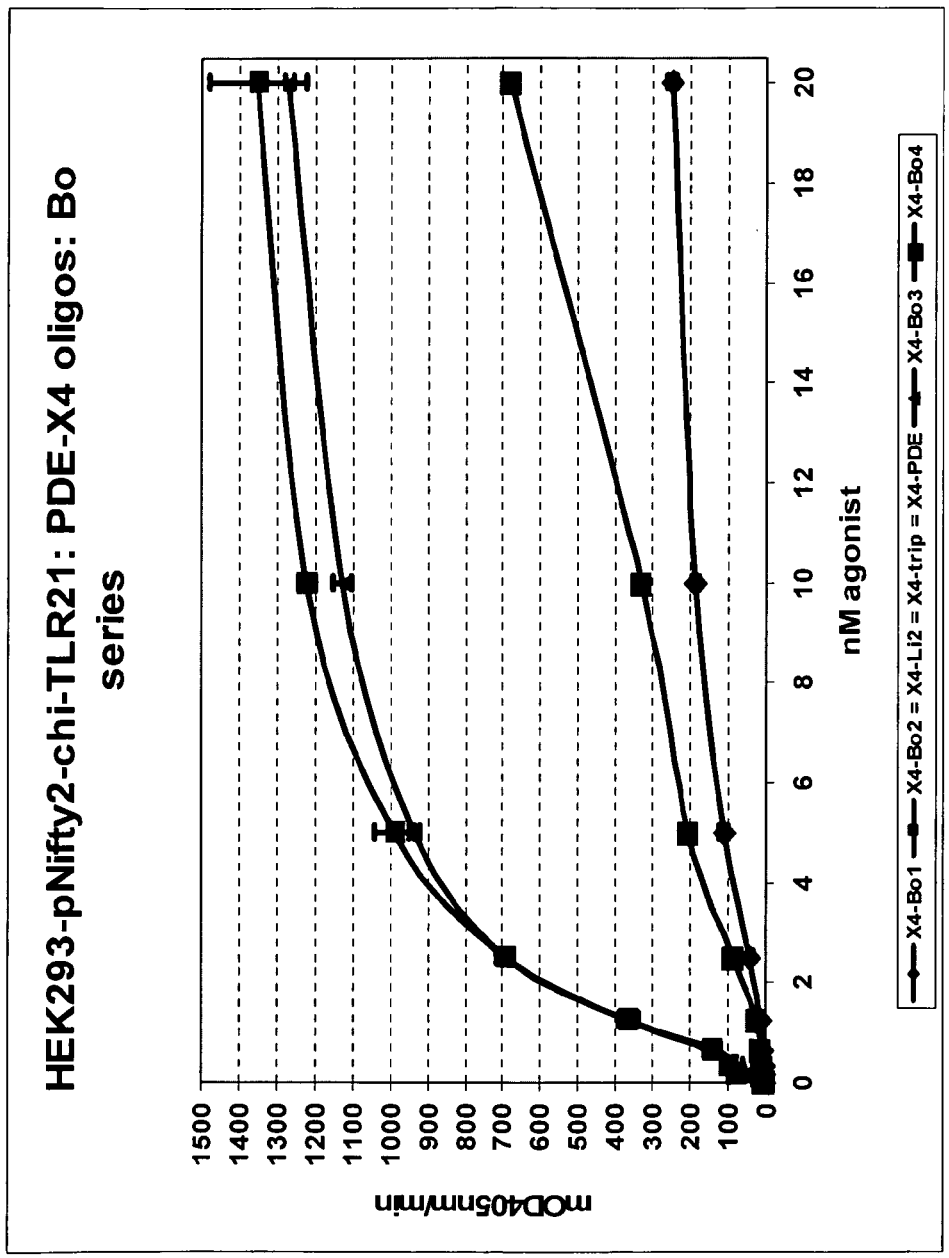

With the HEK293-pNifTy2-pcDNA3.1-chiTLR21 clonal cell line, the results obtained in titration experiments starting at 20 nM are shown in FIG. 21.

The following ranking of stimulatory potency was identified for HEK293-pNifTy2-pcDNA3.1-chiTLR21:
X4-Bo4~X4-Bo3>X4-Bo2 (='classical' X4)>X4-Bo1

In order to further investigate the optimal number of T residues at the borders to the dG runs, the following (same and longer) constructs were made and (re)-tested:

```
                                            (SEQ ID NO: 67)
X4-Bo1    GGGGGGTCGTTTTCGTTTTCGTGGGGG (SEQ ID NO: 68)
X4-Bo2    GGGGGGTTCGTTTTCGTTTTCGTTGGGGG (SEQ ID NO: 69)
X4-Bo3    GGGGGGTTTCGTTTTCGTTTTCGTTTGGGGG (SEQ ID NO: 70)
X4-Bo4    GGGGGGTTTTCGTTTTCGTTTTCGTTTTGGGGG (SEQ ID NO: 71)
X4-Bo5    GGGGGGTTTTTCGTTTTCGTTTTCGTTTTTGGGGG (SEQ ID NO: 72)
X4-Bo6    GGGGGGTTTTTTCGTTTTCGTTTTCGTTTTTTGGGGG
```

Figure 22:
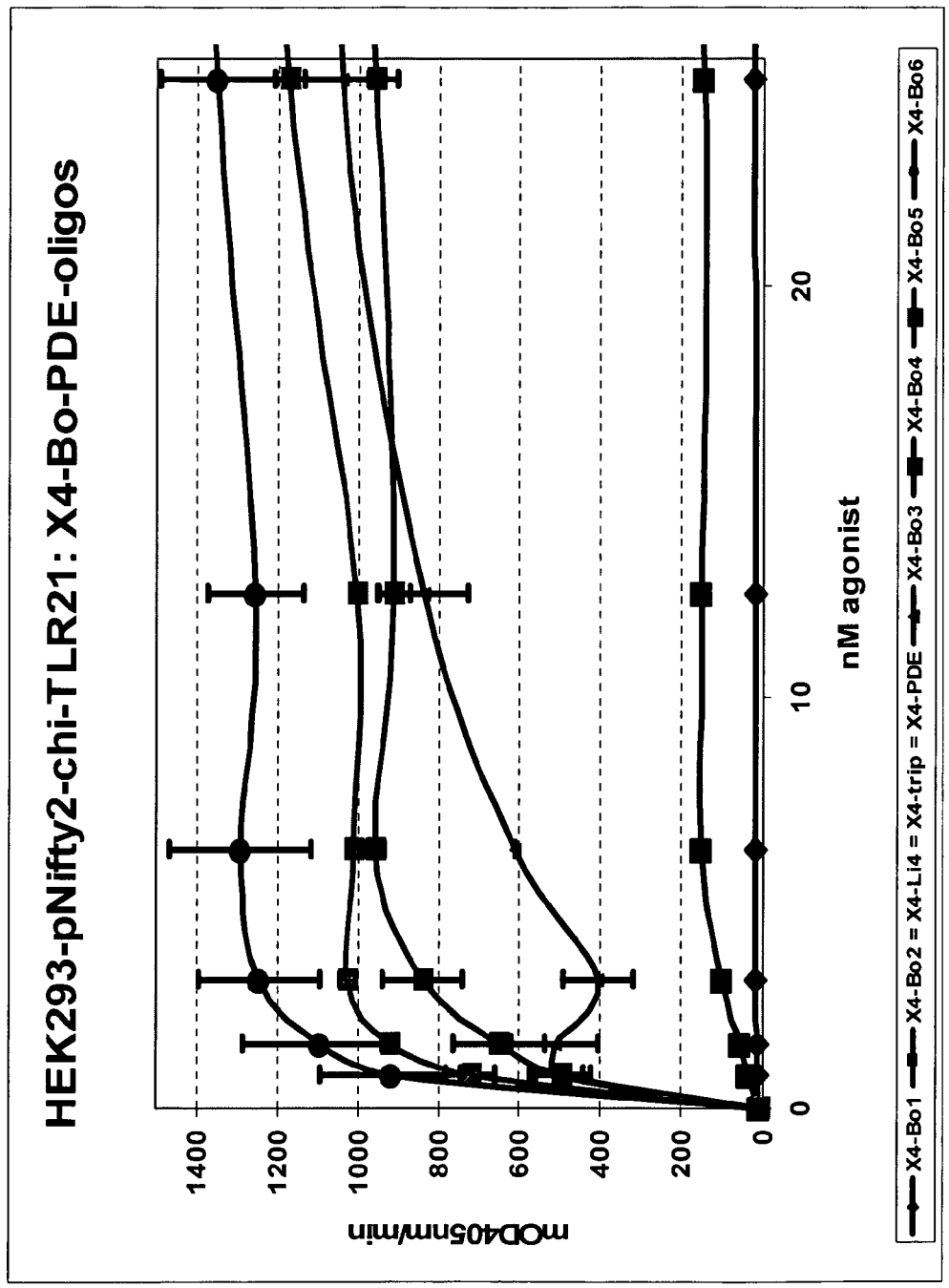

With the HEK293-pNifTy2-pcDNA3.1-chiTLR21 clonal cell line, the results obtained in titration experiments starting at 20 nM are shown in FIG. 22.

The following ranking of stimulatory potency was identified for HEK293-pNifTy2-pcDNA3.1-chiTLR21:
X4-Bo6>X4-Bo5>X4-Bo4>X4-Bo3>X4-Bo2 (='classical' X4)>X4-Bo1

Example 13

Further Investigation of the Effect of the Number of Ts Bordering a Trimer of the Backbone In order to investigate the optimal number of Ts bordering a trimer of the backbone, the following constructs were made:

```
                                            (SEQ ID NO: 63)
X4-Bo1b   GGGGGGTCGTTTTCGTTTTCGTGGGGG (SEQ ID NO: 27)
X4-Bo2b   GGGGGGTTCGTTTTCGTTTTCGTTGGGGG (SEQ ID NO: 65)
X4-Bo3b   GGGGGGTTTCGTTTTCGTTTTCGTTTGGGGG (SEQ ID NO: 66)
X4-Bo4b   GGGGGGTTTTCGTTTTCGTTTTCGTTTTGGGGG (SEQ ID NO: 71)
X4-Bo5b   GGGGGGTTTTTCGTTTTCGTTTTCGTTTTTGGGGG (SEQ ID NO: 72)
X4-Bo6b   GGGGGGTTTTTTCGTTTTCGTTTTCGTTTTTTGGGGG (SEQ ID NO: 73)
X4-Bo7    GGGGGGTTTTTTTCGTTTTCGTTTTCGTTTTTTTGGGGG (SEQ ID NO: 74)
X4-Bo8    GGGGGGTTTTTTTTCGTTTTCGTTTTCGTTTTTTTTGGGGG (SEQ ID NO: 75)
X4-Bo9    GGGGGGTTTTTTTTTCGTTTTCGTTTTCGTTTTTTTTTGGGGG (SEQ ID NO: 76)
X4-Bo10   GGGGGGTTTTTTTTTTCGTTTTCGTTTTCGTTTTTTTTTT
          TGGGGG
```

It appears that both with respect to the maximal stimulation and with respect to the 'effective concentration 50%' (=EC50), the increases caused by addition of further Ts from X4-Bo5 on are marginal or not present. Nevertheless; X4-Bo10 is still highly active. It can thus be safely assumed that the effect of adding more T's levels off. It can easily be envisioned that constructs up to X4-Bo20, X4-Bo25 or even X4-Bo30 are still very suitable. See FIG. 23.

Example 14

Further Investigation of the Effect of the Number of Ts, Separating' the CG Elements In order to investigate the optimal number of Ts separating the CG elements, the following constructs were made:

```
                                            (SEQ ID NO: 77)
X4-Li1b   GGGGGGTTCGTCGTCGTTGGGGG (SEQ ID NO: 78)
X4-Li2b   GGGGGGTTCGTTCGTTCGTTGGGGG (SEQ ID NO: 79)
X4-Li3b   GGGGGGTTCGTTTCGTTTCGTTGGGGG (SEQ ID NO: 80)
X4-Li4b   GGGGGGTTCGTTTTCGTTTTCGTTGGGGG (SEQ ID NO: 81)
X4-Li5b   GGGGGGTTCGTTTTTCGTTTTTCGTTGGGGG (SEQ ID NO: 82)
X4-Li6b   GGGGGGTTCGTTTTTTCGTTTTTTCGTTGGGGG (SEQ ID NO: 83)
X4-Li7    GGGGGGTTCGTTTTTTTCGTTTTTTTCGTTGGGGG (SEQ ID NO: 84)
X4-Li8    GGGGGGTTCGTTTTTTTTCGTTTTTTTTCGTTGGGGG
```

-continued

```
                                              (SEQ ID NO: 85)
X4-Li9     GGGGGGTTCGTTTTTTTTTCGTTTTTTTTTCGTTGGGGG (SEQ ID NO: 86)
X4-Li10    GGGGGGTTCGTTTTTTTTTTCGTTTTTTTTTTCGTTGGGGG
```

As seen before, X4-Li1 and X4-Li2 are inactive in the concentration range considered (<20 nM). It appears that while EC50 does not change much from X4-Li3 to X4-Li7, the maximal stimulation attainable does increase in that order. A surprise is the jump in EC50 from X4-Li7 to X4-Li8, which is also accompanied by an increase in maximal stimulation. X4-Li8, X4-Li9 and X4-Li10 are roughly equally potent with respect to EC50 and maximal stimulation. Nevertheless, X4-Li10 is still highly active. It can thus be safely assumed that the effect of adding more T's levels off. It can easily be envisioned that constructs up to X4-Li20, X4-Li25 or even X4-Li30 are still very suitable. See FIG. 24.

Example 15

Further Investigation of the Effect of the Number of TTCGTT Repeats

In order to investigate the optimal number of TTCGTT repeats, the following constructs were made:

```
                                              (SEQ ID NO: 87)
X4-Sin-b   GGGGGGTTCGTTGGGGG (SEQ ID NO: 88)
X4-Doub-b  GGGGGGTTCGTTTTCGTTGGGGG (SEQ ID NO: 89)
X4-Trip-b  GGGGGGTTCGTTTTCGTTTTCGTTGGGGG (SEQ ID NO: 90)
X4-Quad-b  GGGGGGTTCGTTTTCGTTTTCGTTTTCGTTGGGGG (SEQ ID NO: 91)
X4-Pent-b  GGGGGGTTCGTTTTCGTTTTCGTTTTCGTTTTCGTTGGGGG (SEQ ID NO: 92)
X4-Hex-b   GGGGGGTTCGTTTTCGTTTTCGTTTTCGTTTTCGTTTTCGTTGGGGG (SEQ ID NO: 93)
X4-Hept    GGGGGGTTCGTTTTCGTTTTCGTTTTCGTTTTCGTTTTCGTTTTCGTTGGGGG (SEQ ID NO: 94)
X4-Oct     GGGGGGTTCGTTTTCGTTTTCGTTTTCGTTTTCGTTTTCGTTTTCGTTTTCGTT
           GGGGG (SEQ ID NO: 95)
X4-Non     GGGGGGTTCGTTTTCGTTTTCGTTTTCGTTTTCGTTTTCGTTTTCGTTTTCGTT
           TTCGTTGGGGG (SEQ ID NO: 96)
X4-Dec     GGGGGGTTCGTTTTCGTTTTCGTTTTCGTTTTCGTTTTCGTTTTCGTTTTCGTT
           TTCGTTTTCGTTGGGGG
```

As seen before, X4-sing and X4-doub are inactive in the concentration range considered (<20 nM). It appears the maximal stimulation attainable does increase strongly from X4-trip to X4-hept, and in that order the EC50 also decreases strongly. In particular the jump from X4-quad to X4-pent is remarkable. From X4-hept to X4-dec, the maximal stimulation increases and the EC50 decreases moderately, but continuously. It can thus be safely assumed that the effect of adding more trimers levels off. It can easily be envisioned that constructs up to X4-X, X4-XV or even X4-XVIII are still very suitable. Such constructs would however be increasingly difficult to synthesize. See FIGS. 25 and 26.

Example 16

Further Investigation of the Effect of the Type of Repeat Trimers

In order to investigate the optimal type of repeat trimers, the following constructs were made:

```
                                              (SEQ ID NO: 97)
X4         GGGGGGTTCGTTTTCGTTTTCGTTGGGGG (SEQ ID NO: 98)
X4-I       GGGGGGTTTCGTTTTTTCGTTTTTTCGTTTGGGGG (SEQ ID NO: 99)
X4-II      GGGGGGTTTTCGTTTTTTTCGTTTTTTTCGTTTTGGGGG (SEQ ID NO: 100)
X4-III     GGGGGGTTTTTCGTTTTTTTTTCGTTTTTTTTTCGTTTTT
           TGGGGG
```

Stimulation levels do increase strongly from X4-trip to X4-I to X4-II/X4-III. Furthermore the EC50 decreases strongly from X4 to X4-I and then gets gradually smaller to X4-III. X4-III is still highly active. See FIG. 27.

Example 17

Further Investigation of the Effect of TTTCGTTT Repeats

In order to investigate the optimal number of T residues at the borders of the TTCGTT repeats, the following constructs were made:

```
X4-I-sing    GGGGGGTTTCGTTTGGGGG                                      (SEQ ID NO: 101)

X4-I-doub    GGGGGGTTTCGTTTTTCGTTTGGGGG                               (SEQ ID NO: 102)

X4-I-trip    GGGGGGTTTCGTTTTTCGTTTTTCGTTTGGGGG                        (SEQ ID NO: 103)

X4-I-quad    GGGGGGTTTCGTTTTTCGTTTTTCGTTTTTCGTTTGGGGG                 (SEQ ID NO: 104)

X4-I-pent    GGGGGGTTTCGTTTTTCGTTTTTCGTTTTTCGTTTTTCGTTTGGGGG          (SEQ ID NO: 105)

X4-I-hex     GGGGGGTTTCGTTTTTCGTTTTTCGTTTTTCGTTTTTCGTTTTTCGTTT        (SEQ ID NO: 106)
             GGGGG
```

Like in the X4 series, X4-I-sing and X4-I-doub are inactive in the concentration range considered (<20 nM). The first potent ODN is X4-I, and maximal stimulation attainable increases further for X4-quad and X4-I-pent/X4-I-hex. The $EC_{50}$ is in the same order of magnitude (low nM) for X4-I-trip-X4-I-hex.

X4-I-hex is still highly active. See FIG. 28.

Example 18

Further Investigation of the Trimeric Hexamer CG Motif

3' Border Position

In order to investigate the optimal trimeric hexamer CG motif—3' border position, the following constructs were made:

```
ODN-X4     GGGGGGTTCGTTTTCGTTTTCGTTGGGGG

ODN-X41    GGGGGGTTCGTGTTCGTGTTCGTGGGGGG

ODN-X42    GGGGGGTTCGTATTCGTATTCGTAGGGGG

ODN-X43    GGGGGGTTCGTCTTCGTCTTCGTCGGGGG
```

ODN-X4=(SEQ ID NO: 107), ODN-X41=(SEQ ID NO: 108), ODN-X42=(SEQ ID NO: 109), ODN-X43=(SEQ ID NO: 110),

| $EC_{50}$ calculation: | X4:  | 61.6 nM                 |
|---|---|---|
|                        | X41: | not determined, >> 100 nM |
|                        | X42: | 62.1 nM                 |
|                        | X43: | 3.3 nM                  |

Based on these (and earlier) results, ODN-X43 is superior to ODN-X4 both with respect to the maximal stimulation and $EC_{50}$ value. ODN-X42 is somewhat lower with respect to the maximal signal, but the $EC_{50}$ is similar to that of ODN-X4.

Example 19

Further Investigation of the Trimeric Hexamer CG Motif

Identification of GTCGTC

In exploring the potential of PDE-ODNs based on ODN-X2, the following ODNs were synthesized as modifications of the 5'- and 3' end of the hexamer. The results of X2, X24, X25 and X26/X4 were reported above.

```
ODN-X2     GGGGGGGTCGTTGTCGTTGTCGTTGGGGG            (SEQ ID NO: 111)

ODN-X21    GGGGGGGTCGTGGTCGTGGTCGTGGGGGG            (SEQ ID NO: 112)

ODN-X22    GGGGGGGTCGTAGTCGTAGTCGTAGGGGG            (SEQ ID NO: 113)

ODN-X23    GGGGGGGTCGTCGTCGTCGTCGTCGGGGG            (SEQ ID NO: 114)

ODN-X24    GGGGGGATCGTTATCGTTATCGTTGGGGG            (SEQ ID NO: 115)

ODN-X25    GGGGGGCTCGTTCTCGTTCTCGTTGGGGG            (SEQ ID NO: 116)

ODN-X26/4  GGGGGGTTCGTTTTCGTTTTCGTTGGGGG            (SEQ ID NO: 117)
```

X2, X24, X25, like X21 and X22, are only poorly active or inactive compared to X26/X4. X23, however, showed an unexpected high activity superior to that of X26/X4.

| $EC_{50}$ calculation: | X23: | 3.1 nM |
|---|---|---|
|                        | X4:  | 61.6 nM |

Based on these (and earlier) results, ODN-X23 is superior to ODN-X4 both with respect to the maximal stimulation and $EC_{50}$ value.

Example 20

Effect of the ODN-X42 Motif Number

ODN-X42 is based on a trimer of the TTCGTA motif. In order to test the effect of the motif number, the motif number was investigated from 1 to 6:

```
X42-sin    GGGGGGTTCGTAGGGGG                        (SEQ ID NO: 118)

X42-doub   GGGGGGTTCGTATTCGTAGGGGG                  (SEQ ID NO: 119)

X42-trip   GGGGGGTTCGTATTCGTATTCGTAGGGGG            (SEQ ID NO: 120)
```

```
                                                      (SEQ ID NO: 121)
X42-quad     GGGGGGTTCGTATTCGTATTCGTATTCGTAGGGGG (SEQ ID NO: 122)
X42-pent     GGGGGGTTCGTATTCGTATTCGTATTCGTATTCGTAGGGGG (SEQ ID NO: 123)
X42-hex      GGGGGGTTCGTATTCGTATTCGTATTCGTATTCGTATTCGT
             AGGGGG
```

| | $EC_{50}$ |
|---|---|
| ODN-X4-trip | 40.6 nM |
| ODN-X42-trip | 33 nM |
| ODN-X42-quad | 3.1 nM |
| ODN-X42-pent | 0.84 nM |
| ODN-X42-hex | 0.37 nM |
| ODN-X4-trip-PTO-Gonly | 6.8 nM |

As seen in the previous experiment, the potencies of X4-trip and X42-trip are comparable. Decreasing the number of hexanucleotide repeats in the X42 series leads to loss of activity (X42-sing, X42-doub), while increase in number to 4, 5 and 6 leads to an increase in maximal signal and EC50 in that order, reaching picomolar potency at X42-pent. Also remarkable is the fact, that from X42-quad onwards the ODNs are superior to ODN-X4-trip-PTO-Gonly.

It can easily be envisioned that constructs up to n=10, n=15 or even n=18 are still very suitable. Such constructs would however be increasingly difficult to synthesize. See FIG. 29.

Example 21

Effect of the ODN-X43 Motif Number

ODN-X43 is based on a trimer of the TTCGTC motif. In order to test the effect of the motif number, the motif number was investigated from 1 to 6.

Furthermore the PTOG-only variants of X43-trip-X43-hex were synthesized and tested.

```
                                                      (SEQ ID NO: 124)
X43-Sin      GGGGGGTTCGTCGGGGG (SEQ ID NO: 125)
X43-Doub     GGGGGGTTCGTCTTCGTCGGGGG (SEQ ID NO: 126)
X43-Trip     GGGGGGTTCGTCTTCGTCTTCGTCGGGGG (SEQ ID NO: 127)
X43-Quad     GGGGGGTTCGTCTTCGTCTTCGTCTTCGTCGGGGG (SEQ ID NO: 128)
X43-Pent     GGGGGGTTCGTCTTCGTCTTCGTCTTCGTCTTCGTCGGGGG (SEQ ID NO: 129)
X43-Hex      GGGGGGTTCGTCTTCGTCTTCGTCTTCGTCTTCGTCTTCGTCGGGGG (SEQ ID NO: 126)
X43-Trip-PTOg gggggGTTCGTCTTCGTCTTCGTCggggg (SEQ ID NO: 127)
X43-Quad-PTOg gggggGTTCGTCTTCGTCTTCGTCTTCGTCggggg (SEQ ID NO: 128)
X43-Pent-PTOg gggggGTTCGTCTTCGTCTTCGTCTTCGTCTTCGTCggggg (SEQ ID NO: 129)
X43-Hex-PTOg gggggGTTCGTCTTCGTCTTCGTCTTCGTCTTCGTCTTCGTCggggg
```

| | $EC_{50}$ [nM] |
|---|---|
| ODN-X4-trip | 40.6 |
| ODN-X43-trip | 1.2 |
| ODN-X43-quad | 0.56 |
| ODN-X43-pent | 0.4 |
| ODN-X43-hex | 0.38 |
| ODN-X43-trip-PTOG-only | 1.12 |
| ODN-X43-quad-PTOG-only | 0.51 |
| ODN-X43-pent-PTOG-only | 0.32 |
| ODN-X43-hex-PTO-Gonly | 0.38 |
| X4-PTOG-only | 6.8 |

As seen in the previous experiments, the potency of X43-trip is superior to that of X4-trip. Decreasing the number of hexanucleotide repeats in the X43 series leads to loss of activity (X43-sing, X43-doub), while increase in number to 4, 5 and 6 leads to an increase in maximal signal and $EC_{50}$ in that order, reaching picomolar potency already at X43-quad. Also remarkable is the fact, that all X43-ODNs from X43-trip onwards are superior to ODN-X4-trip-PTO-Gonly.

The PTOG-only versions of X43-trip-X43-hex are at least as active as the purely phosphodiester-linked ODN versions.

X43-hex and X43-hex-PTOG-only are still highly active, i.e. the limits and/or the optimum have not yet been reached.

Again, it can easily be envisioned that constructs up to n=10, n=15 or even n=18 are still very suitable. Such constructs would however be increasingly difficult to synthesize. See FIGS. 30 and 31.

Example 22

Further Variations of ODN-X4

With the aim to explore further the potential of PDE-ODNs based on ODN-X4, ODNs were synthesized with replacements of the TT dinucleotides 5'- and 3'- of the CpG elements with GG, AA and CC, respectively.

| | | |
|---|---|---|
| X4-TT = TT-X4 | GGGGGGTTCGTTTTCGTTTTCGTTGGGGG | (SEQ ID NO: 130) |
| X-GG | GGGGGGGGCGTTGGCGTTGGCGTTGGGGG | (SEQ ID NO: 131) |
| X-AA | GGGGGGAACGTTAACGTTAACGTTGGGGG | (SEQ ID NO: 132) |
| X-CC | GGGGGGCCCGTTCCCGTTCCCGTTGGGGG | (SEQ ID NO: 133) |
| GG-X | GGGGGGTTCGGGTTCGGGTTCGGGGGGGG | (SEQ ID NO: 134) |
| AA-X | GGGGGGTTCGAATTCGAATTCGAAGGGGG | (SEQ ID NO: 135) |
| CC-X | GGGGGGTTCGCCTTCGCCTTCGCCGGGGG | (SEQ ID NO: 136) |

In the HEK293-pNifty2-chiTLR21 stimulation tests, X4-GG, X4-AA, X4-CC, GG-X and AA-X proved to be inactive over the concentration ranges considered. However, CC-X ($EC_{50}$=6.94 nM) showed an $EC_{50}$ activity superior by a factor of 7 to that of X4 ($EC_{50}$=52.3 nM) and also showing higher maximal stimulation signals. See FIG. 32.

Example 23

Animal Testing of CpG Motifs According to the Invention

1 Introduction 1.1 Objective

To assess whether a TLR (Toll Like Receptor) ligand combined with a minimal amount of inactivated NDV Clone 30 antigen combined with W/O EMULSION can give protection against a live NDV Herts 33/56 challenge.

1.2

2 Materials And Methods 2.1 Short Outline of the Experiment

Eighteen groups of 3 weeks-old SPF White Leghorn chickens, placed in isolators, were vaccinated only once intramuscularly (i.m.) in the right breast muscle with one of the formulations indicated in Table 1 "Grouping and dosing". From each group of 12 animals only 10 chickens were vaccinated the other 2 birds served as controls. Blood samples were taken 1 day before vaccination (T=0) from 18 randomly picked animals (1 from each group) and at T=3 weeks post-vaccination from all animals from all groups. After blood sampling at T=3 weeks post-vaccination all chickens were challenged via the intramuscular (i.m.) route in the right leg muscle with 0.2 ml ($10^{6.0}$ $EID_{50}$) per chicken of the velogenic NDV strain Herts 33/56. During a period of 14 days post-challenge chickens were scored daily for the occurrence of clinical evidence of NDV infection or mortality. Two weeks post-challenge blood was taken from all remaining animals after which the animals were euthanized. The local reactions were macroscopically investigated and scored. Samples for routine histology were taken when reactions or lesions were visible.

2.2 Test Materials 2.2.1

2.2.1.1 Vaccine 0.25% w/w inactivated NDV Clone 30 in W/O emulsion 2.2.1.2 TLR Ligands X4-PDE (Y11)—produced by Biolegio—The Netherlands
X4-PTO (Y11)—produced by TibMolBiol—Berlin—Germany
X4-PTO-G-only (Y11)—produced by TibMolBiol
2007-PTO (known from literature)—produced by TibMolBiol 2.2.1.3 CpG sequences:

```
X4-PDE (Y11):
GGGGGGTTCGTTTTCGTTTTCGTTGGGGG
(complete PDE backbone) (SEQ ID NO: 27)

X4-PTO (Y11):
gsgsgsgsgsgsTsCsgsTsTsTsTsCsgsTsTsTsTsCsgsTsT
sgsgsgsgsgs
(complete PTO backbone) (SEQ ID NO: 27)

X4-PTO-G-only (Y11):
gsgsgsgsgsgsTTCGTTTTCGTTTTCGTTgsgsgsgsgs
(PTO g-stretch) (SEQ ID NO: 27)

2007-PTO:
TsCsgsTsCsgsTsTsgsTsCsgsTsTsTsTsgsTsCsgsTsTs
(complete PTO backbone) (SEQ ID NO: 137)
PTO = phospho(ro)thioate (indicated with "s")(= nuclease
resistant);
PDE = phosphodiester (standard oligo synthesis)
```

TABLE 1

| | | | Grouping and dosing | | |
|---|---|---|---|---|---|
| gr | N | IP nr | vaccine | TLR ligand | TLR |
| 1 | 10 | 100132.1 | 0.25% w/w NDV in W/O emulsion | — (PBS) | — |
|   | 2 | — | — | | |
| 2 | 10 | 100132.4 | 0.25% w/w NDV in W/O emulsion | 1 µg/dose X4-PDE (Y11) | TLR21 |
|   | 2 | — | — | | |
| 3 | 10 | 100132.5 | 0.25% w/w NDV in W/O emulsion | 10 µg/dose X4-PDE(Y11) | TLR21 |
|   | 2 | — | — | | |
| 4 | 10 | 100132.7 | 0.25% w/w NDV in W/O emulsion | 1 µg/dose X4-PTO (Y11) | TLR21 |
|   | 2 | — | — | | |

TABLE 1-continued

Grouping and dosing

| gr | N | IP nr | vaccine | TLR ligand | TLR |
|---|---|---|---|---|---|
| 5 | 10 | 100132.8 | 0.25% w/w NDV in W/O emulsion | 10 μg/dose X4-PTO (Y11) | TLR21 |
|   | 2 | — | — | — |   |
| 6 | 10 | 100132.10 | 0.25% w/w NDV in W/O emulsion | 1 μg/dose X4-PTO-G-only (Y11) | TLR21 |
|   | 2 | — | — | — |   |
| 7 | 10 | 100132.11 | 0.25% w/w NDV in W/O emulsion | 10 μg/dose X4-PTO-G-only (Y11) | TLR21 |
|   | 2 | — | — | — |   |
| 8 | 10 | 100132.13 | 0.25% w/w NDV in W/O emulsion | 1 μg/dose 2007-PTO | TLR21 |
|   | 2 | — | — | — |   |
| 9 | 10 | 100132.14 | 0.25% w/w NDV in W/O emulsion | 10 μg/dose 2007-PTO | TLR21 |
|   | 2 | — | — | — |   |

2.2.2 Vaccine Preparation

With each TLR ligand a certain dilution was freshly made which was added to the [0.25% w/w NDV in W/O emulsion]-vaccine up to a final concentration of 2.5% v/v resulting in a dose of 1 μg or 10 μg per 0.5 ml. (A full vaccine dose of the experimental vaccine used here comprises 8.06% w/v allantois fluid of NDV-infected eggs/W/O emulsion). After addition of the TLR ligand to the vaccine it was thoroughly mixed using a mini-vortex.

(A "¼ dose of inactivated Newcastle Disease virus" means; ¼ of the minimal amount of inactivated NDV known to give an antibody titer that is capable of protecting poultry against NDV infection in the absence of the oligodeoxynucleotide).

2.3 Vaccination

Ten animals from each group were vaccinated with 0.5 ml vaccine i.m. in the right breast muscle at the age of 3 weeks-old. The remaining 2 animals in each group were not vaccinated and served as controls.

2.4 Challenge

At 3 weeks post-vaccination all 12 animals from all 18 groups were challenged with 0.2 ml Live NDV Herts 33/56 ($10^{6.0}$ $EID_{50}$ per chicken) via the i.m. route in the right leg muscle.

2.5 Blood Samples

Blood samples for serology were taken 1 day before vaccination (T=0) from 18 randomly picked animals (1 from each group) and at T=3 weeks post primo-vaccination from all animals. Two weeks post-challenge blood was taken from all remaining animals that survived the NDV challenge.

2.6 HI-Assay

Serum levels of NDV-specific antibodies were determined by a haemagglutination-inhibition (HI) assay. Serial two-fold dilutions of sera were prepared in microtiter plates and mixed with an equal volume containing 8 haemagglutinating units/50 μl NDV antigen. Titers are expressed as the reciprocal of the highest dilution that gives complete inhibition of haemagglutination of chicken red blood cells (1% (v/v) in buffered saline). Samples were regarded positive for inhibition of haemagglutination at a dilution≥1:2.

3 Results

| | 0.25% (w/w) NDV clone 30 in GNE | | |
|---|---|---|---|
| gr. TLR ligand | at 3 wkpv* mean Log2 NDV HI titre | ⇩ % chickens protected | at 5 wkpv (=2wkpc*) mean Log2 NDV HI titre |
| 1 — | 0.0 ± 0.0 | 0% | — |
| 2  1 μg/dose X4-PDE (Y11) | 1.5 ± 1.7 | 40% | 9.3 ± 1.0 |
| 3  10 μg/dose X4-PDE (Y11) | 4.3 ± 1.9 | 70% | 9.1 ± 1.1 |
| 4  1 μg/dose X4-PTO (Y11) | 1.7 ± 1.3 | 30% | 8.7 ± 0.6 |
| 5  10 μg/dose X4-PTO (Y11) | 2.3 ± 2.2 | 40% | 8.3 ± 0.5 |
| 6  1 μg/dose X4-PTO-G-only (Y11) | 2.2 ± 1.6 | 40% | 9.3 ± 1.0 |
| 7  10 μg/dose X4-PTO-G-only (Y11) | 5.0 ± 1.5 | 90% | 8.8 ± 0.7 |
| 8  1 μg/dose 2007-PTO | 2.5 ± 1.6 | 60% | 8.7 ± 0.8 |
| 9  10 μg/dose 2007-PTO | 3.3 ± 2.1 | 70% | 9.0 ± 0.6 |

*wkpv = weeks post-vaccination; wkpc = weeks post-challenge

NDV HI Titers:

From the results it is also clear that the NDV HI titers correlate nicely with protection. For each TLR ligand that induced protection, the highest HI titer was found to correlate with the highest protection, i.e. at 10 μg per dose. In contrast, at the highest dose of TLR ligand the HI titer was the lowest.

Histology and Pathology:

At macroscopic investigation of the injection sites, there were no major macroscopic differences found between the injection sites of the birds from the different groups. These observations indicate that the used TLR ligands were safe and that they did not induce additional side effects, e.g. local reactions.

Protection/Survival:

From the results it is clear that no protection was obtained with NDV in W/O emulsion only (group 1), while in some other groups 20% to 90% of the birds were protected due to the addition of a TLR ligand to the 0.25% (w/w) NDV clone 30 in W/O emulsion.

No protection was observed in the non-vaccinated control chickens (n=36).

Example 24

Further animal testing of CpG motifs according to the invention:

1 Introduction 1.1 Objective

To assess the influence of X4-Pent-PDE in combination with W/O emulsion (a water-in-oil emulsion based upon a mineral oil) on the anti-NDV, anti-IBV and anti-TRT antibody titers in chickens.

1.2 Motivation

In this trial we investigated whether the addition of X4-Pent-PDE to one quarter of a full dose of inactivated NDV, IBV or TRT antigen combined with W/O emulsion can evoke antibody titers which are equal or higher when compared to the full dose of NDV and TRT, or to a half dose of IBV.

2 Material And Methods 2.1 Short Outline of the Experiment

Groups of 4 weeks-old SPF White Leghorn chickens (n=10 per group) were vaccinated once i.m. in the right leg muscle with one of the formulations indicated in table 2. Blood samples were taken before vaccination (T=0) from 20 randomly picked animals and at T=4 and T=6 weeks post-vaccination from all animals from all groups. Sera were used to determine the anti-NDV, anti-IBV and anti-TRT antibody titers.

2.2 Test Materials 2.2.1 Test Articles 2.2.1.1 Antigens (Inac.)

NDV clone 30: A full vaccine dose comprises 8.06% w/v allantois fluid of NDV-infected eggs/W/O emulsion.
IBV-249G: A full vaccine dose comprises 30% w/v allantois fluid of IB-infected eggs/W/O emulsion.
TRT: standard production batch. A full vaccine dose comprises 100 E.U./dose.

2.2.1.2 Vaccines: See Table 2

2.2.1.3 Immunostimulant

X4-Pent-PDE: (SEQ ID NO: 55)
5'-GGGGGGTTCGTTTTCGTTTTCGTTTTCGTTTTCGTTGGGGG-3'.
(Eurofins MWG Operon (Germany))

(Eurofins MWG Operon (Germany))

2.2.2 Vaccine Preparation

A X4-Pent-PDE TLR ligand pre-dilution was freshly made and added to the vaccines up to a final concentration of 2.5% v/v resulting in a dose of 1 μg or 10 μg per 0.5 ml vaccine. After addition of the TLR ligand the vaccine was thoroughly mixed using a mini-vortex.

2.3 Vaccination

The animals from each group were vaccinated with 0.5 ml vaccine i.m. in the right leg muscle at the age of 4 weeks-old.

2.4 Blood Samples

Blood samples for serology were taken before vaccination (T=0) from 20 randomly picked animals and at T=4 weeks post primo-vaccination from all animals.

2.5 Antibody Titers 2.5.1 NDV HI-Assay

Serum levels of NDV-specific antibodies were determined by a haemagglutination-inhibition (HI) assay. Serial two-fold dilutions of sera were prepared in microtiter plates and mixed with an equal volume containing 8 haemagglutinating units/50 μl NDV antigen. Titers are expressed as the reciprocal of the highest dilution that gives complete inhibition of haemagglutination of chicken red blood cells (1% (v/v) in buffered saline). Samples were regarded positive for inhibition of haemagglutination at a dilution≥1:4 and are expressed in 2 log.

2.5.2 IBV HI-Assay

Serum levels of IB-specific antibodies were determined by a haemagglutination-inhibition (HI) assay. Serial two-fold dilutions of sera were prepared in microtiter plates and mixed with an equal volume containing 8-16 haemagglutinating units/50 μl IBV-D274 antigen. Titers are expressed as the reciprocal of the highest dilution that gives complete inhibition of haemagglutination of chicken red blood cells (1% (v/v) in buffered saline). Samples were regarded positive for inhibition of haemagglutination at a dilution≥1:16 and are expressed in 2 log.

2.5.3 TRT ELISA

Serum levels of TRT-specific antibodies were determined by standard ELISA. Briefly, 100 μl of 1:200 diluted TRT antigen material was coated in microtiter plates. Sera were pre-diluted 1:100 and 1:800 and added to the microtiter plates. Serum titers are regarded positive at a titer≥5 and are expressed in 2 log.

2.5.4 Conclusion

The following can immediately be concluded from the results of table 2:
1) a ¼ dosis NDV-vaccine when administered together with 10 μg X4-Pent gives a titre that is comparable with the titre of a full dose of NDV without the addition of X4-Pent.
2) a ¼ dosis of a combined NDV/IBV-vaccine when administered together with 10 μg X4-Pent gives an NDV- and IBV-titre that is comparable with a full dose of a combined NDV/IBV-vaccine without the addition of X4-Pent.
3) a ¼ dosis TRT-vaccine when administered together with 10 μg X4-Pent gives a titre that is comparable to a full dose of TRT-vaccine without the addition of X4-Pent.

TABLE 2

| vaccine (+LV-W/O emulsion) | | | | T = 4 weeks | | | T = 6 weeks | | |
|---|---|---|---|---|---|---|---|---|---|
| NDV | IBV-249G | TRT | PAMP | NDV | IBV | TRT | NDV | IBV | TRT |
| full | — | — | — | 9.3 ± 0.7 | — | — | 9.2 ± 0.8 | — | — |
| — | ½ | — | — | — | 9.3 ± 1.8 | — | — | 9.4 ± 0.7 | — |
| full | ½ | — | — | 9.2 ± 0.9 | 9.1 ± 1.5 | — | 8.6 ± 1.1 | 9.2 ± 0.8 | — |
| ¼ | — | — | 10 μg X4-Pent | 9.2 ± 1.0 | — | — | 8.8 ± 0.9 | — | — |
| ¼ | ¼ | -- | 10 μg X4-Pent | 9.5 ± 0.5 | 9.9 ± 2.0 | — | 9.0 ± 0.8 | 9.5 ± 0.5 | — |
| — | — | full | — | — | — | 11.7 ± 0.4 | — | — | 12.4 ± 0.3 |
| — | — | ¼ | 10 μg X4-Pent | — | — | 12.2 ± 0.4 | — | — | 12.3 ± 0.8 |
| full = 8.06% w/v | full = 30.1% w/v | full = 100 EU | | | | | | | |

LEGEND TO THE FIGURES

FIG. 1: Plasmid map of pcDNA3.1(+)-chiTLR21

FIG. 2-5: overview of the SEAP activity of the various zeo/G418-double-resistant clonal cell lines.

Figure 23:
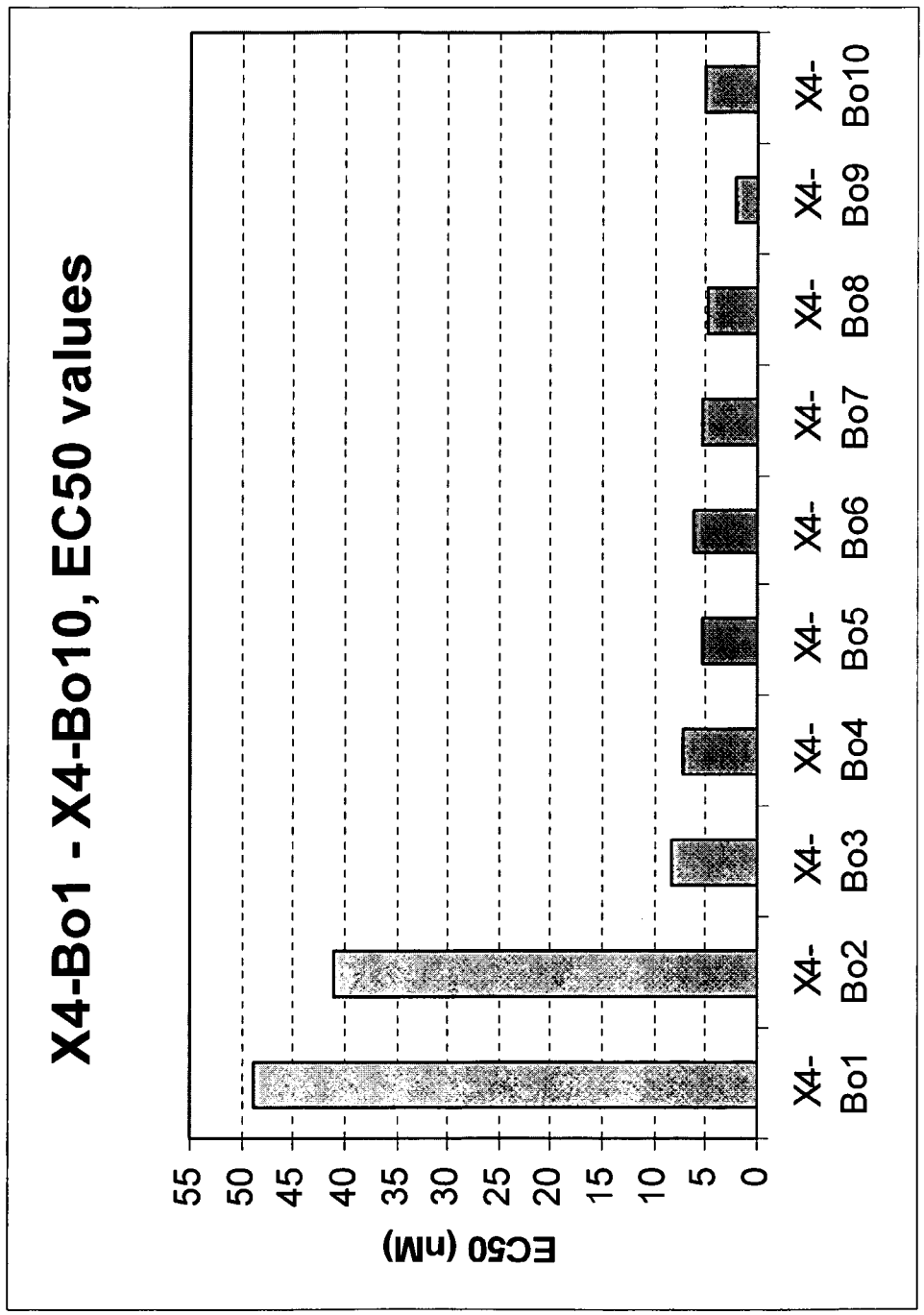
Figure 24:
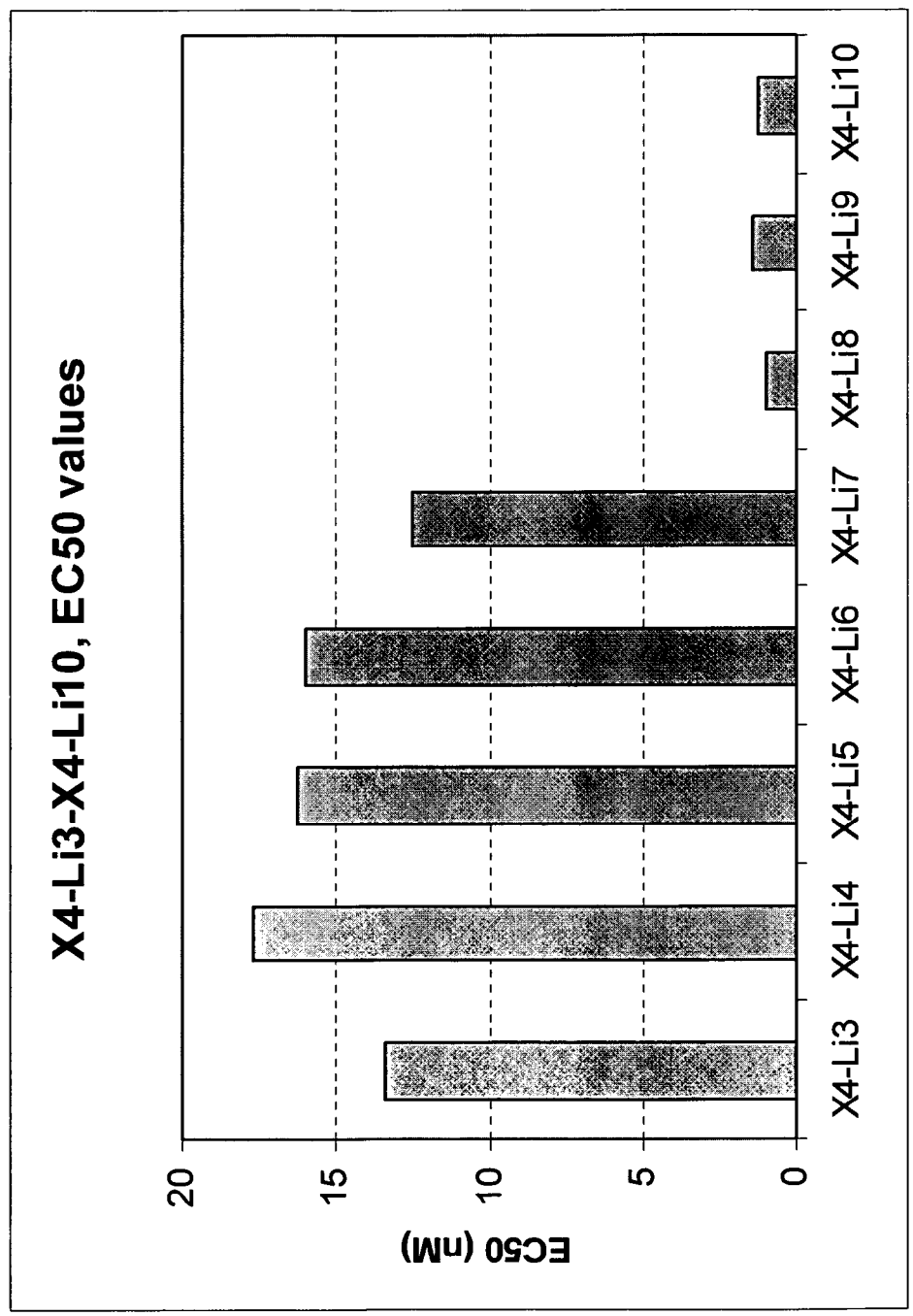
Figure 25:
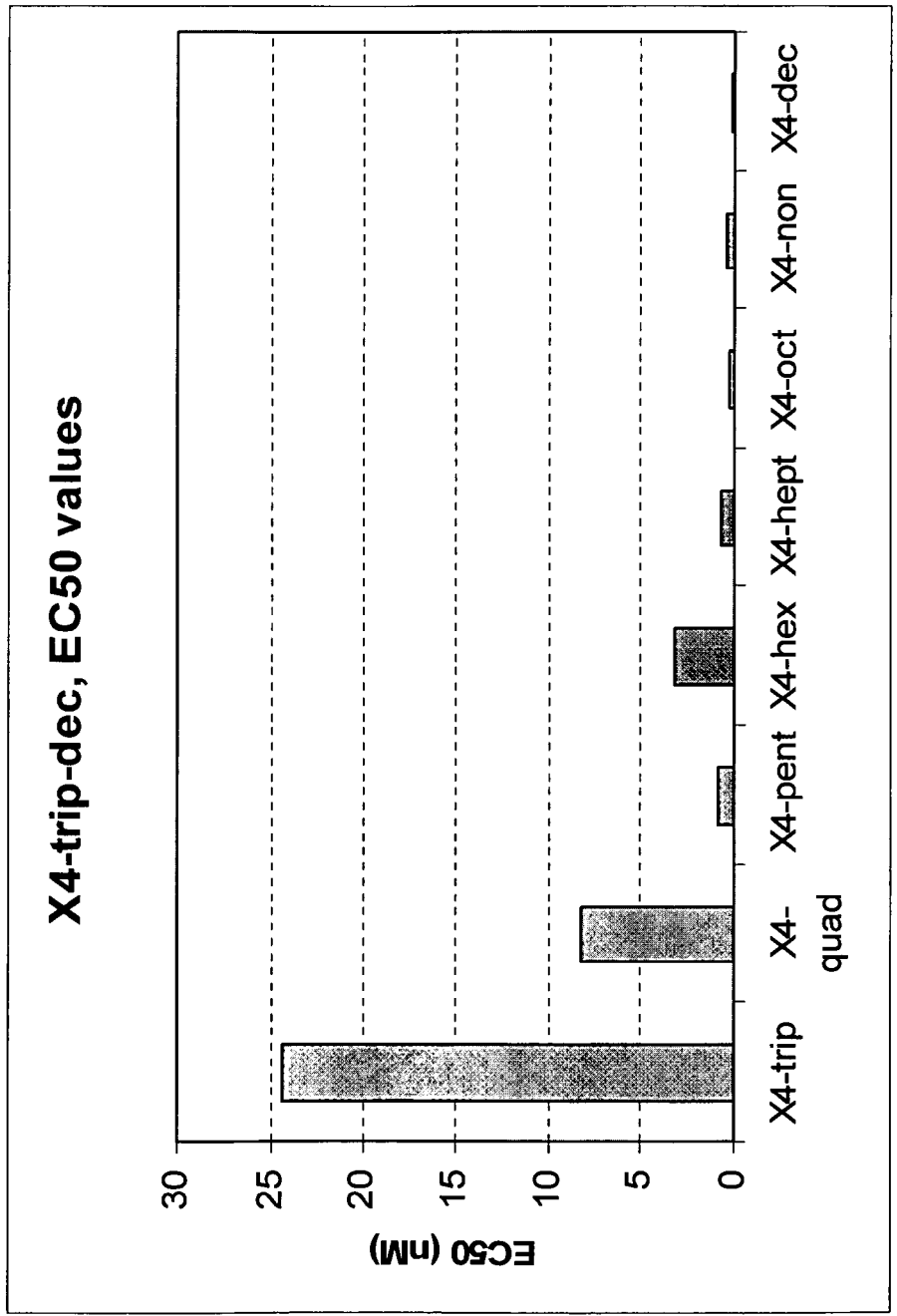
Figure 26:
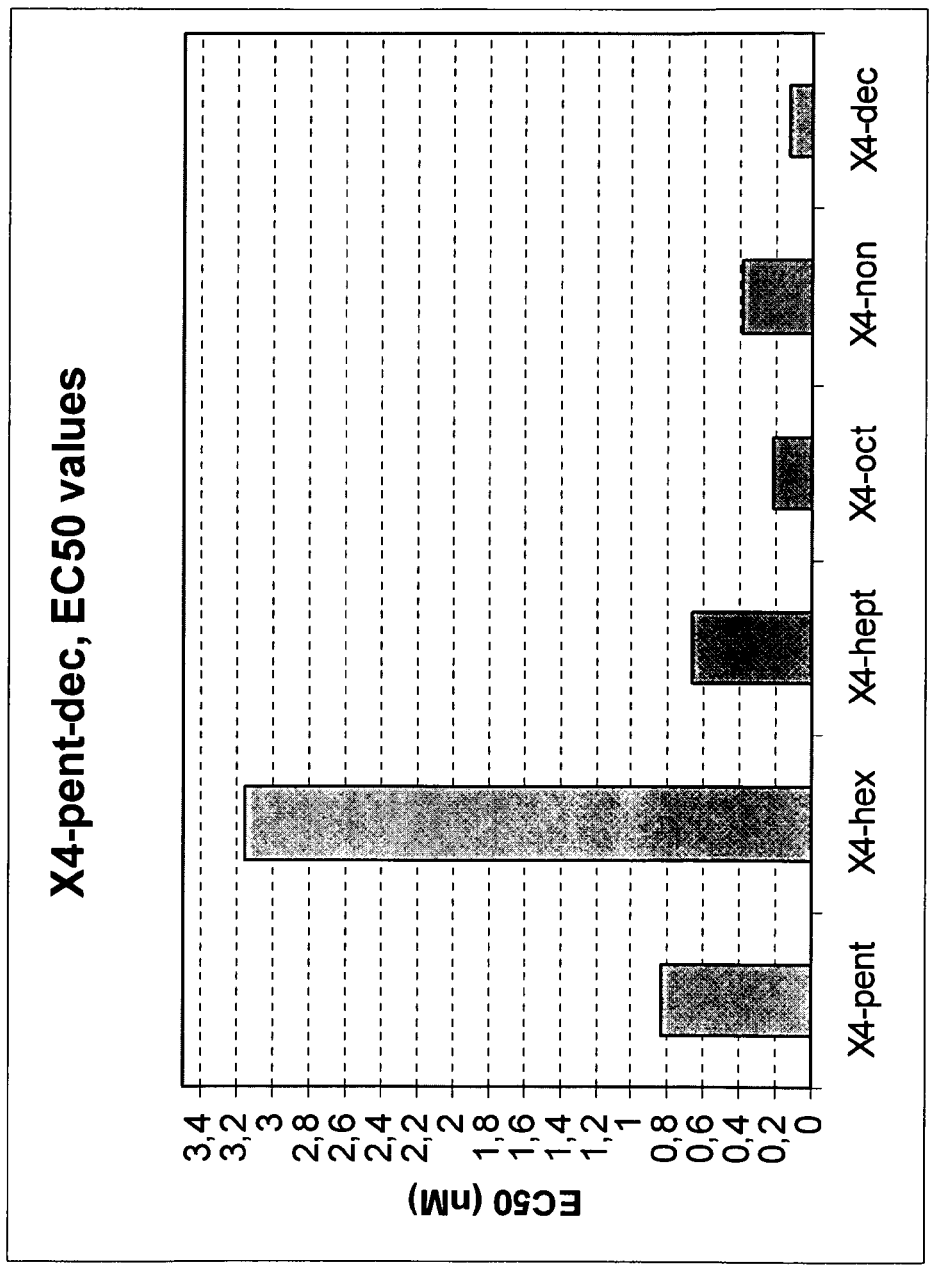
Figure 27:
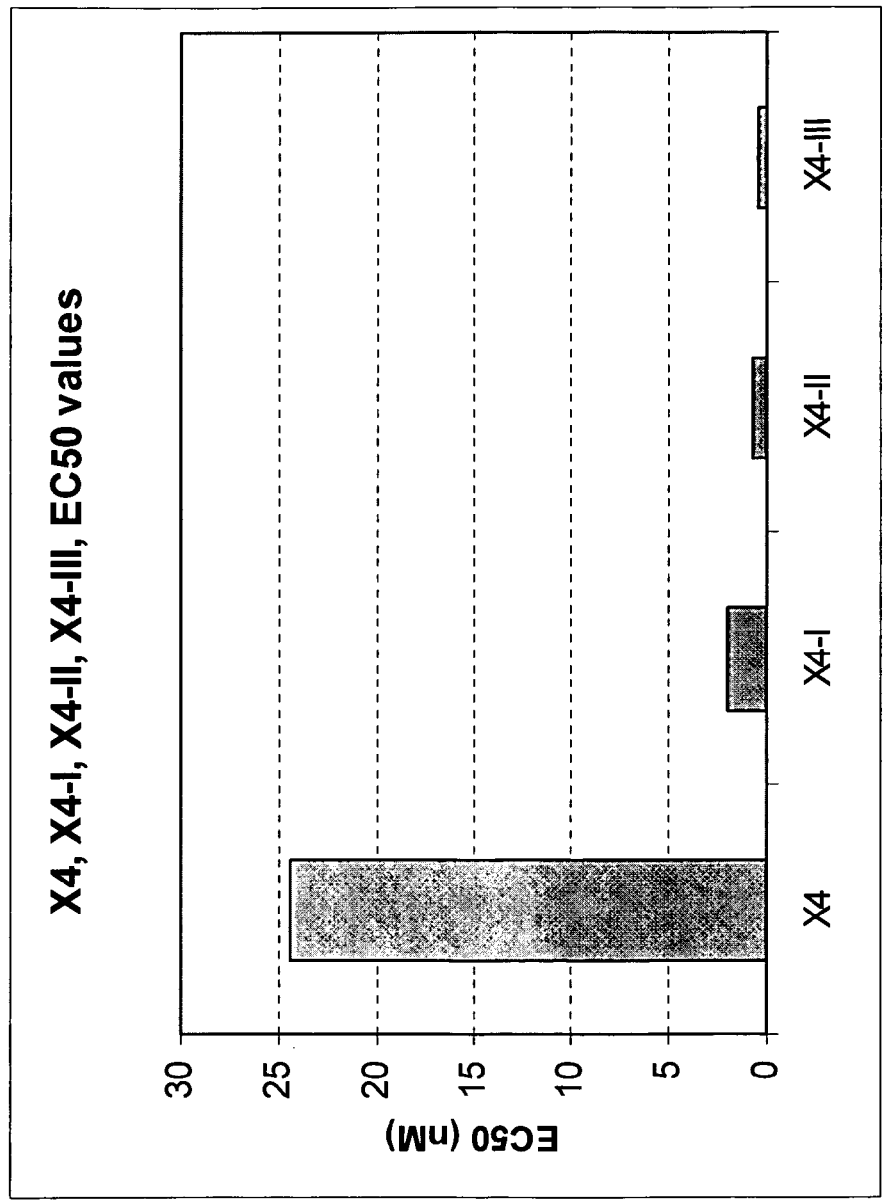
Figure 28:
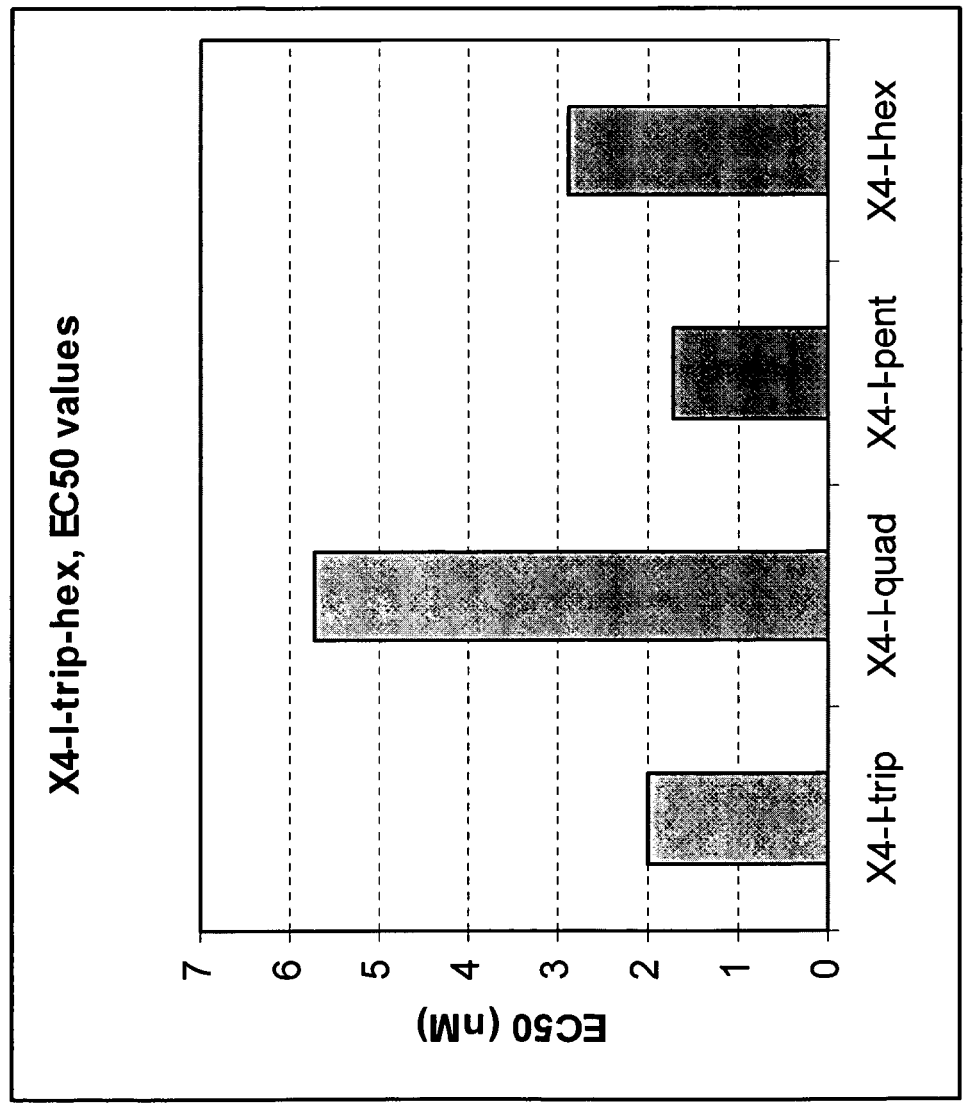
Figure 29:
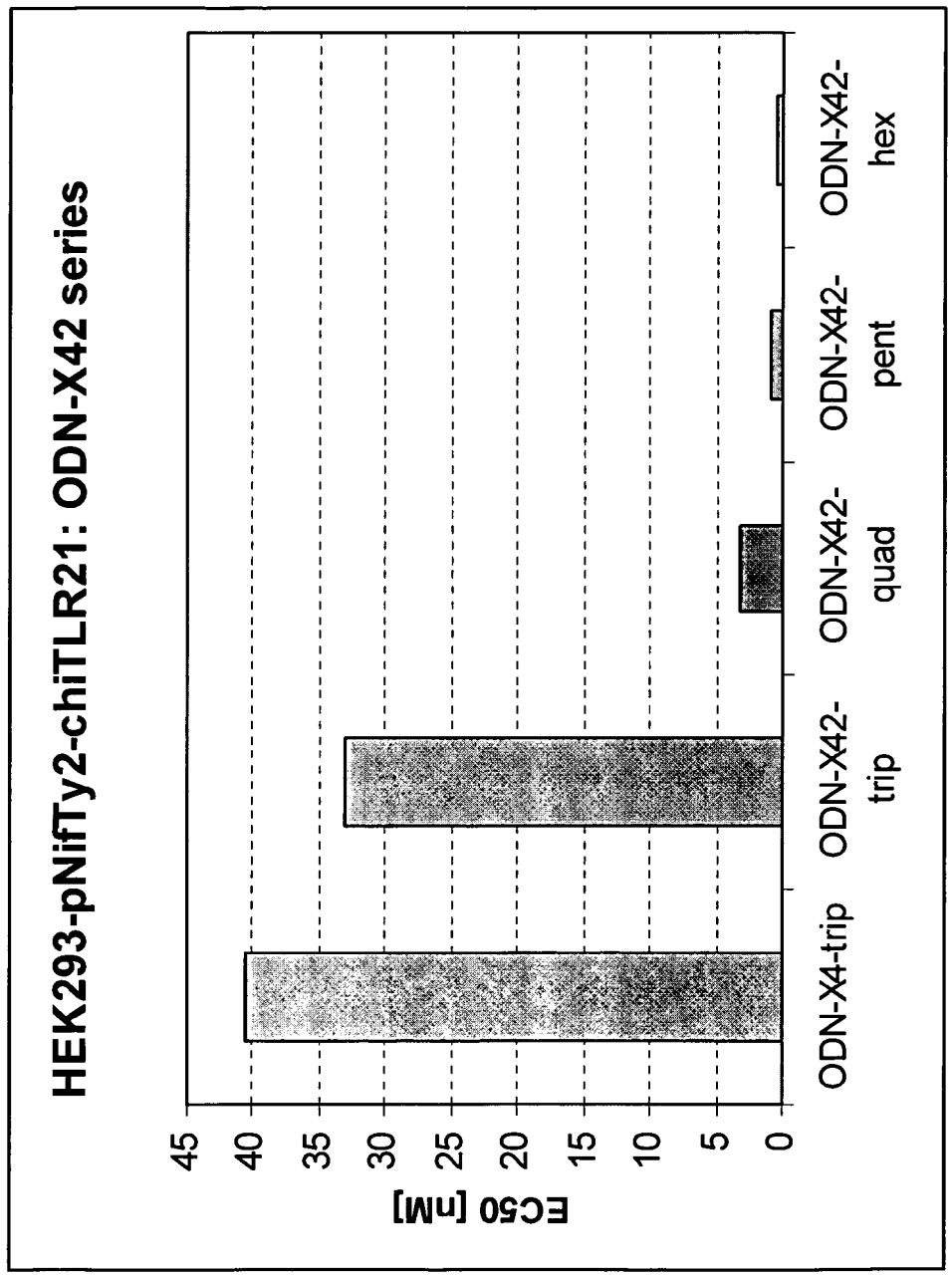
Figure 30:
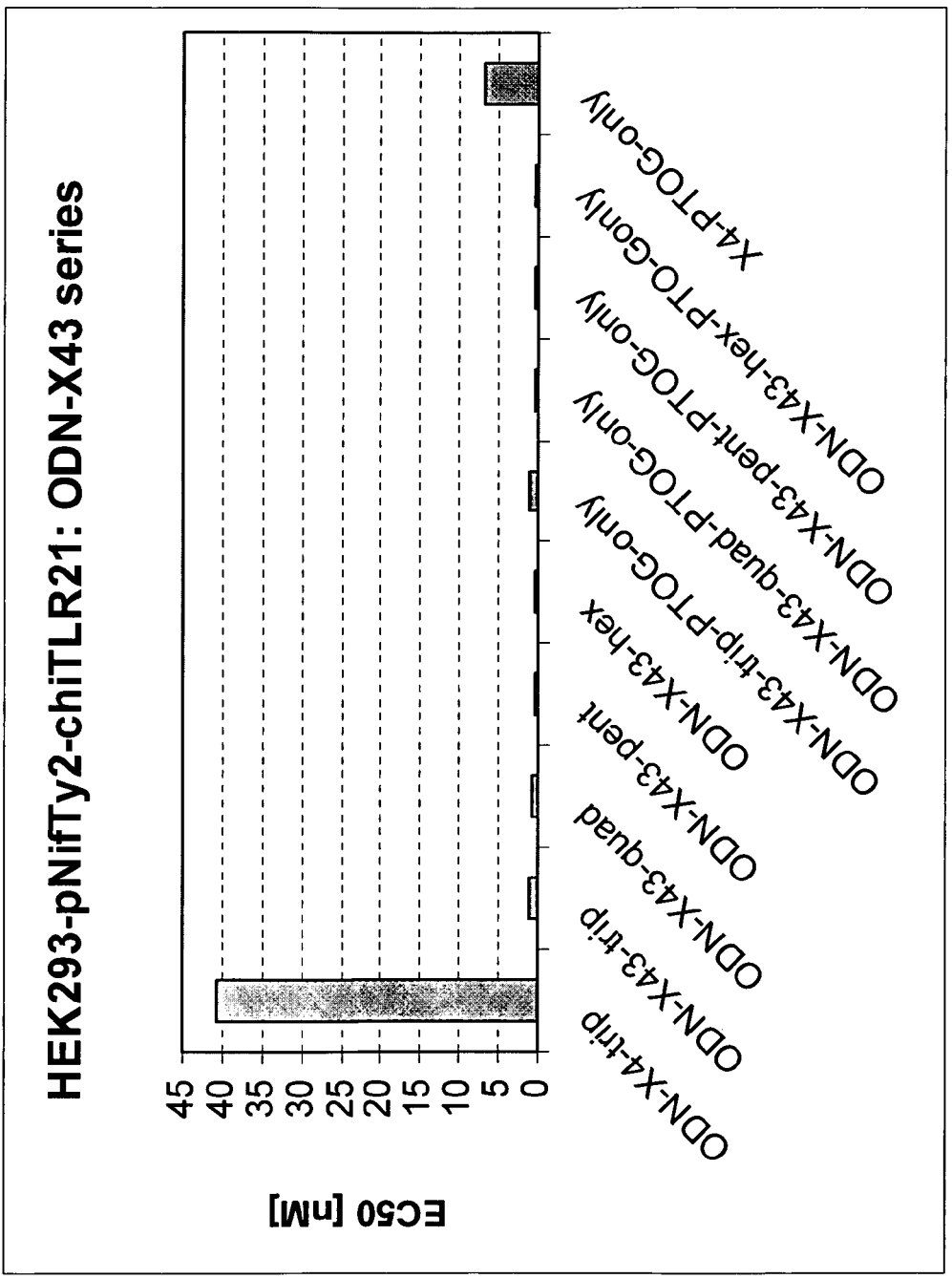
Figure 31:
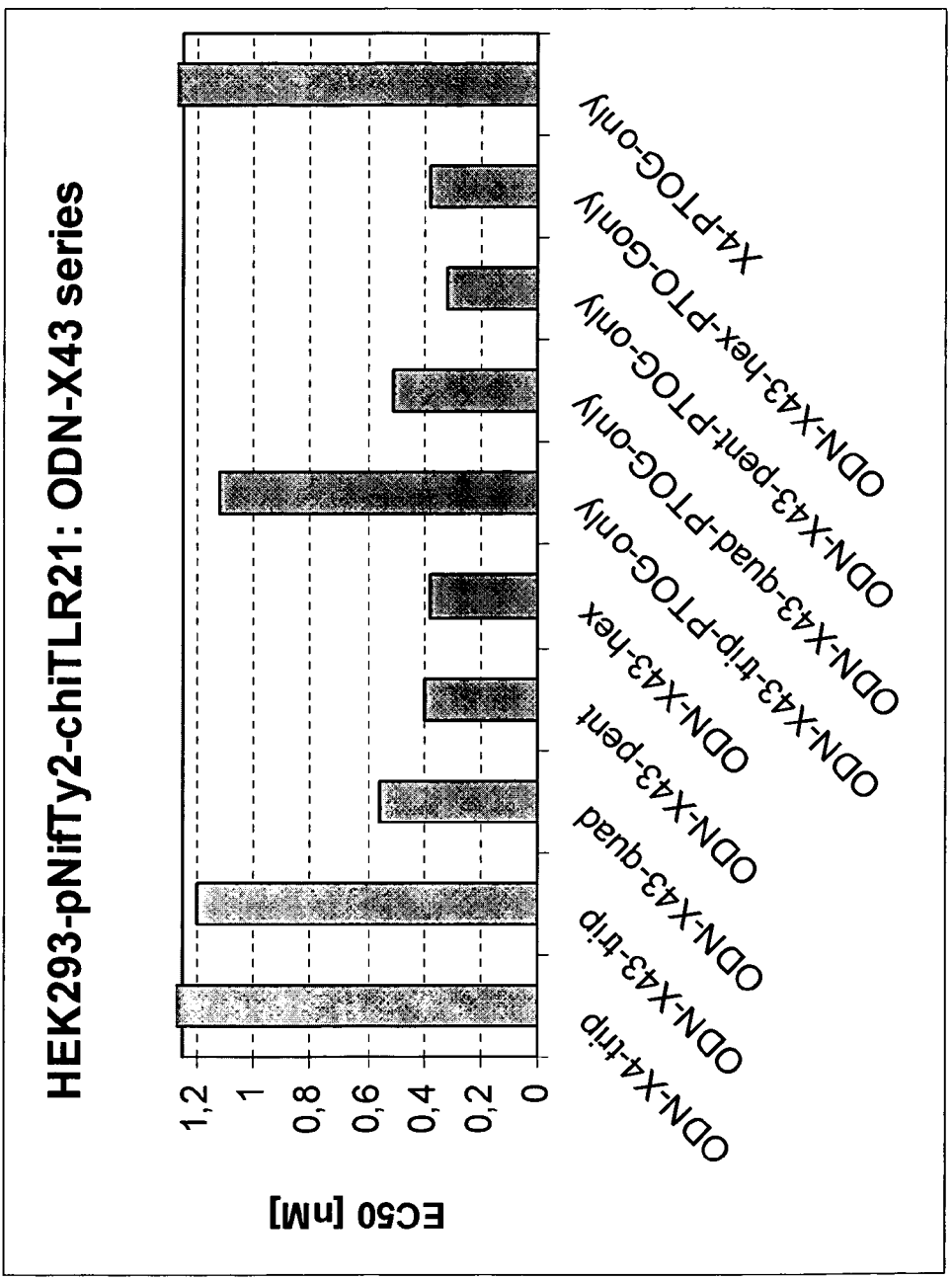
Figure 32:
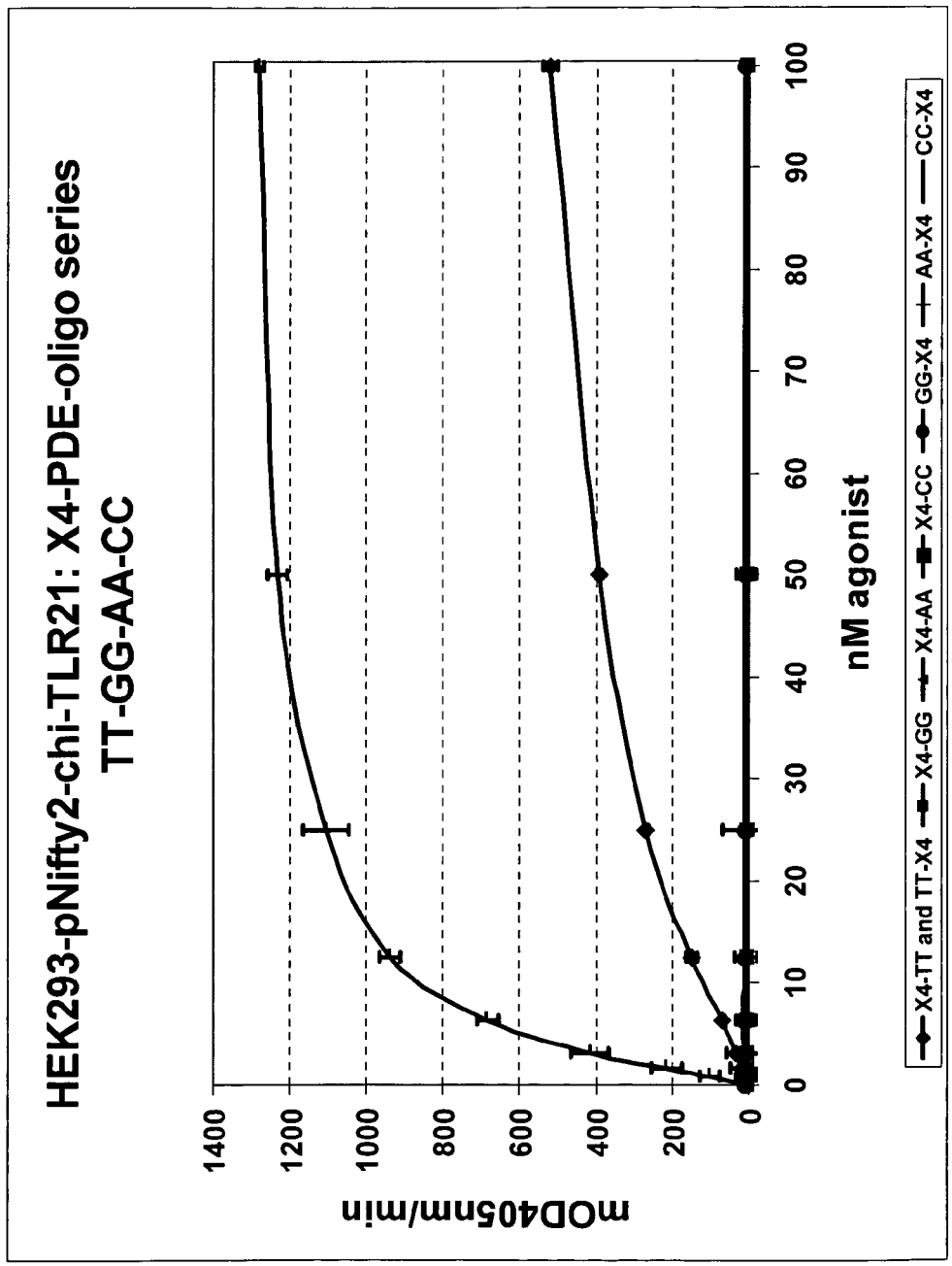

FIG. 6: titration experiments starting at 2000 nM with the HD11-pNifTyhyg clonal cell line FIG. 7: the HEK293-pNifTy2-pcDNA3.1-chiTLR21 clonal cell line results obtained in titration experiments starting at 100 nM FIG. 8: the HD11-pNifTyhyg clonal cell line results obtained in titration experiments starting at 2000 nM FIG. 9: the HEK293-pNifTy2-pcDNA3.1-chiTLR21 clonal cell line results obtained in titration experiments starting at 100 nM FIG. 10: the HD11-pNifTyhyg clonal cell line results obtained in titration experiments starting at 2000 nM FIG. 11-15: the HEK293-pNifTy2-pcDNA3.1-chiTLR21 clonal cell line results obtained in titration experiments starting at 100 nM FIG. 16-17: the HEK293-pNifTy2-pcDNA3.1-chiTLR21 clonal cell line results obtained in titration experiments starting at 50 nM FIG. 18: the HEK293XL-pUNO-huTLR9-pNifTy2 clonal cell line results obtained in titration experiments starting at 50 nM FIG. 19: the HEK293-pNifTy2-pcDNA3.1-chiTLR21 clonal cell line results obtained in titration experiments starting at 20 nM FIG. 20: the HEK293-pNifTy2-pcDNA3.1-chiTLR21 clonal cell line results obtained in titration experiments starting at 25 nM FIG. 21: the HEK293-pNifTy2-pcDNA3.1-chiTLR21 clonal cell line results obtained in titration experiments starting at 20 nM FIG. 22: the HEK293-pNifTy2-pcDNA3.1-chiTLR21 clonal cell line results obtained in titration experiments starting at 20 nM FIG. 23: effect of the number of Ts bordering a trimer of the backbone FIG. 24: effect of the number of Ts 'separating' the CG elements FIG. 25: effect of the number of TTCGTT repeats FIG. 26: the effect of the number of TTCGTT repeats FIG. 27: the effect of the type of repeat trimers FIG. 28: the effect of number of T residues at the borders of the TTCGTT repeats FIG. 29: the effect of the ODN-X42 motif number FIG. 30-31: the effect of the ODN-X43 motif number FIG. 32: further variations of ODN-X4

LITERATURE REFERENCES

Babiuk L. A., Gomis S., Hecker R., 2003. Molecular approaches to disease control. *Poult. Sci.* 82, 870-875.

Brownlie, R., Zhu J., Allan B., Mutwiri G. K., Babiuk L. A., Potter A., Griebel P., 2009. Chicken TLR21 acts as a functional homologue to mammalian TLR9 in the recognition of CpG oligodeoxynucleotides. *Mol. Immunol.* 46, 3163-3170

Carrington A. C., Secombes C. J., 2006. A review of CpGs and their relevance to aquaculture. *Vet. Immunol. Immunopathol.* 112, 87-101.

Daubenberger C. A., 2007. TLR9 agonists as adjuvants for prophylactic and therapeutic vaccines. *Curr. Opin. Mol. Ther.* 9, 45-52.

Dorn A., Kippenberger S., 2008. Clinical application of CpG-, non-CpG-, and antisense oligodeoxynucleotides as immunomodulators. *Curr. Opin. Mol. Ther.* 10, 10-20.

Fonseca D. E., Kline J. N., 2009. Use of CpG oligodeoxynucleotides in treatment of asthma and allergic disease. *Adv. Drug Deliv. Rev.* 61, 256-262.

Graham, F. L., Smiley, J., Russell, W. C., Nairn, R., 1977. Characteristics of a human cell line transformed by DNA from human adenovirus type 5. *J. Gen. Virol.* 36, 59-74.

Griebel P. J., Brownlie R., Manuja A., Nichani A., Mookherjee N., Popowych Y., Mutwiri G., Hecker R., Babiuk L. A., 2005. Bovine toll-like receptor 9: a comparative analysis of molecular structure, function and expression. *Vet. Immunol. Immunopathol.* 108, 11-16.

Hemmi H., Takeuchi O., Kawai T., Kaisho T., Sato S., Sanjo H., Matsumoto M., Hoshino K., Wagner H., Takeda K., Akira S., 2000. A Toll-like receptor recognizes bacterial DNA. *Nature* 408, 740-745.

Iwasaki A, Medzhitov R. Regulation of adaptive immunity by the innate immune system. 2010. *Science* 327, 291-295.

Keestra A. M., 2008. Molecular dissection of the chicken Toll-like receptor repertoire. PhD thesis (Proefschrift), University of Utrecht, The Netherlands Kline J. N., 2007. Immunotherapy of asthma using CpG oligodeoxynucleotides. *Immunol. Res.* 39, 279-286.

Kline J. N., Krieg A. M., 2008. Toll-like receptor 9 activation with CpG oligodeoxynucleotides for asthma therapy. *Drug News Perspect.* 21, 434-439.

Klinman D. M., 2004. Immunotherapeutic uses of CpG oligodeoxynucleotides. *Nat. Rev. Immunol.* 4, 249-258.

Klinman D. M, Currie D., Gursel I., Verthelyi D., 2004. Use of CpG oligodeoxynucleotides as immune adjuvants. *Immunol. Rev.* 199, 201-216.

Klinman D. M., 2006. Adjuvant activity of CpG oligodeoxynucleotides. *Int. Rev. Immunol.* 25, 135-154.

Klinman D. M., Klaschik S., Sato T., Tross D., 2009. CpG oligodeoxynucleotides as adjuvants for vaccines targeting infectious diseases. *Adv. Drug Deliv. Rev.* 61, 248-255.

Kindrachuk J., Potter J., Wilson H. L., Griebel P., Babiuk L. A., Napper S., 2008. Activation and regulation of toll-like receptor 9: CpGs and beyond. *Mini Rev. Med. Chem.* 8, 590-600.

Krieg A. M., Yi A, K., Matson S, Waldschmidt T, J., Bishop G. A., Teasdale R., Koretzky G. A., Klinman D. M., 1995. CpG motifs in bacterial DNA trigger direct B-cell activation. *Nature* 374, 546-549.

Krieg A. M., 2002. CpG motifs in bacterial DNA and their immune effects. *Annu. Rev. Immunol.* 20, 709-760.

Krieg A. M., 2003. CpG motifs: the active ingredient in bacterial extracts? *Nat. Med.* 9, 831-835.

Krieg A. M., 2006. Therapeutic potential of Toll-like receptor 9 activation. *Nat. Rev. Drug Discov.* 5, 471-484.

Krieg A. M., 2007a. Anti-infective applications of toll-like receptor 9 agonists. *Proc. Am. Thorac. Soc.* 4, 289-294.

Krieg A. M., 2007b. Development of TLR9 agonists for cancer therapy. *J. Clin. Invest.* 117, 1184-1194.

Linghua Zhang et al., 2007. Vaccination with Newcatle disease vaccine and CpG oligodeoxynucleotides induces specific immunity and protection against Newcastle disease virus in SPF chicken. *Vet. Immun. And Immunopath.* 115, 216-222.

Medzhitov R., 2001. CpG DNA: security code for host defense. *Nat. Immunol.* 2, 15-16.

Medzhitov R., Approaching the asymptote: 20 years later. 2009. *Immunity* 30, 766-775)

Mutwiri G., van Drunen Littel-van den Hurk S., Babiuk L. A., 2009. Approaches to enhancing immune responses stimulated by CpG oligodeoxynucleotides. *Adv. Drug Deliv. Rev.* 61, 226-232.

Mutwiri G., Pontarollo R., Babiuk S., Griebel P., van Drunen Littel-van den Hurk S., Mena A., Tsang C., Alcon V., Nichani A., Ioannou X., Gomis S., Townsend H., Hecker R., Potter A., Babiuk L. A., 2003. Biological activity of immunostimulatory CpG DNA motifs in domestic animals. Vet. Immunol. Immunopathol. 91, 89-103.

Schindler, U., and Baichwal, V. R., 1994. Moll. Cell. Biol. 14: 5820-5831.

Singh M., O'Hagan D. T., 2003. Recent advances in veterinary vaccine adjuvants. *Int. J. Parasitol.* 33, 469-478.

Vollmer J., 2005. Progress in drug development of immunostimulatory CpG oligodeoxynucleotide ligands for TLR9. *Expert Opin. Biol. Ther.* 5, 673-682.

Vollmer J., Krieg A. M., 2009. Immunotherapeutic applications of CpG oligodeoxynucleotide TLR9 agonists. *Adv. Drug Deliv. Rev.* 61, 195-204.

Wagner H., 2009. The immunogenicity of CpG-antigen conjugates. *Adv. Drug. Deliv. Rev.* 61, 243-247.

Weiner G. J., 2009. CpG oligodeoxynucleotide-based therapy of lymphoid malignancies. *Adv. Drug Deliv. Rev.* 61, 263-267.

Werling D., Jungi T. W., 2003. TOLL-like receptors linking innate and adaptive immune response. *Vet. Immunol. Immunopathol.* 91, 1-12.

Wilson H. L., Dar A., Napper S. K., Marianela Lopez A., Babiuk L. A., Mutwiri G. K., 2006. Immune mechanisms and therapeutic potential of CpG oligodeoxynucleotides. *Int. Rev. Immunol.* 25, 183-213.

Wilson K. D., de Jong S. D., Tam Y. K., 2009. Lipid-based delivery of CpG oligodeoxynucleotides enhances immunotherapeutic efficacy. *Adv. Drug Deliv. Rev.* 61, 233-242.

Yang, T. T., Sinai, P., Kitts, P. A., Kain, S. R., 1997. Quantification of gene expression with a secreted alkaline phosphatase reporter system. *Biotechniques* 23, 1110-1114.

The invention claimed is:

1. An immunostimulatory non-methylated oligodeoxynucleotide having the general formula

wherein
$N_1$ is G;
$N_2$ is G;
$N_3$=T;
Each $N_4$ and $N_5$ are T;
$N_6$=A, T or C;
$N_7$=G;
$N_8$=G;
x=3-10;
z=0-10;
n=3-10;
p=1-25;
q=1-25;
r=0-8;
s=0-8;
or a pharmaceutically acceptable salt thereof.

2. The oligodeoxynucleotide of claim 1, wherein $N_6$=T.

3. The oligodeoxynucleotide of claim 1, wherein $N_6$=C.

4. The oligodeoxynucleotide of claim 1, wherein x is 4-7 and r=0.

5. The oligodeoxynucleotide of claim 1, wherein x=6.

6. The oligodeoxynucleotide of claim 1, wherein z is 0-6 and s=0.

7. The oligodeoxynucleotide of claim 6, wherein z is 0-3.

8. The oligodeoxynucleotide of claim 1, wherein n is 4-10.

9. The oligodeoxynucleotide of claim 1, wherein n is 5-10.

10. The oligodeoxynucleotide of claim 1, wherein n is 5-10 and x is 4-7 and z is 0-3 and r=0, and s=0.

11. The oligodeoxynucleotide of claim 1, wherein the $N_1$'s and the $N_2$'s have a phosphorothioate binding and the other nucleotides have a phosphodiester binding.

12. The oligodeoxynucleotide of claim 1, wherein $\{N_3 [N_4]_p\ C\ G\ [N_5]_q N_6\}_n$ is a homopolymer.

13. The oligodeoxynucleotide of claim 1, wherein said oligodeoxynucleotide is coupled to a carrier or hapten.

14. A vector comprising the oligodeoxynucleotide of claim 1.

15. A vaccine for preventing or combating an infectious disease, characterised in that said vaccine comprises an immunostimulatory amount of an oligodeoxynucleotide of claim 1 or a vector comprising the oligodeoxynucleotide, an immunological amount of an antigen component or genetic information encoding an antigen component, and a pharmaceutically acceptable carrier.

16. The vaccine of claim 15, characterised in that said antigen component is, or is derived from a virus or micro-organism that in its wild-type form is pathogenic to poultry.

17. The vaccine of claim 16, characterised in that said virus or micro-organism is selected from the group consisting of Infectious Bronchitis virus, Newcastle Disease virus, Infectious Bursal Disease (Gumboro), Chicken Anaemia agent, Avian Reovirus, *Mycoplasma gallisepticum*, Turkey Rhinotracheitis virus, *Haemophilus paragallinarum* (Coryza), Chicken Poxvirus, Avian Encephalomyelitis virus, Egg Drop syndrome virus, Infectious Laryngotracheitis virus, Herpes Virus of Turkeys, *Eimeria* species, *Ornithobacterium rhinotracheale*, *Pasteurella multocida*, *Mycoplasma synoviae*, *Salmonella* species and *E. coli*.

18. A medicament comprising the immunostimulatory non-methylated oligodeoxynucleotide of claim 1 in combination with an immunological amount of an antigenic component or genetic information encoding an antigenic component.

19. A method of preventing infectious disease in poultry comprising administrating the immunostimulatory non-methylated oligodeoxynucleotide of claim 1 in combination with an immunological amount of an antigenic component or genetic information encoding an antigenic component.

* * * * *